US008759285B2

(12) United States Patent
Szkudlinski et al.

(10) Patent No.: US 8,759,285 B2
(45) Date of Patent: Jun. 24, 2014

(54) VEGF SUPERAGONISTS AND METHODS OF USE

(75) Inventors: Mariusz W. Szkudlinski, Rockville, MD (US); Bruce D. Weintraub, Rockville, MD (US)

(73) Assignee: Trophogen, Inc., Rockville, MD (US)

( * ) Notice: Subject to any disclaimer, the term of this patent is extended or adjusted under 35 U.S.C. 154(b) by 1393 days.

(21) Appl. No.: 12/089,296

(22) PCT Filed: Oct. 6, 2006

(86) PCT No.: PCT/US2006/039181

§ 371 (c)(1), (2), (4) Date: Dec. 22, 2009

(87) PCT Pub. No.: WO2007/044534

PCT Pub. Date: Apr. 19, 2007

(65) Prior Publication Data

US 2010/0216702 A1 Aug. 26, 2010

Related U.S. Application Data

(60) Provisional application No. 60/723,917, filed on Oct. 6, 2005, provisional application No. 60/808,106, filed on May 25, 2006.

(51) Int. Cl.

| | |
|---|---|
| ***A61K 38/18*** | (2006.01) |
| ***A61K 38/16*** | (2006.01) |
| ***A61K 38/17*** | (2006.01) |
| ***C07K 14/475*** | (2006.01) |

(52) U.S. Cl.
USPC .............................. 514/8.1; 514/1.1; 530/350

(58) Field of Classification Search
None
See application file for complete search history.

(56) References Cited

U.S. PATENT DOCUMENTS

| | | | | |
|---|---|---|---|---|
| 6,475,796 | B1 * | 11/2002 | Pollitt et al. | 435/455 |
| 6,485,942 | B1 * | 11/2002 | Zioncheck et al. | 435/69.4 |
| 6,750,044 | B1 * | 6/2004 | Keyt et al. | 435/69.4 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era, Trends in Biotech. 18(1):34-39.*

* cited by examiner

*Primary Examiner* — Christine J Saoud
*Assistant Examiner* — Jon M Lockard
(74) *Attorney, Agent, or Firm* — Morgan Lewis & Bockius LLP

(57) ABSTRACT

Modified VEGF proteins that inhibit VEGF-mediated activation or proliferation of endothelial cells are disclosed. The analogs may be used to inhibit VEGF-mediated activation of endothelial cells in angiogenesis-associated diseases such as cancer, inflammatory diseases, eye diseases, and skin disorders.

17 Claims, 6 Drawing Sheets

VEGF SUPERAGONISTS AND METHODS OF USE

CROSS-REFERENCE TO RELATED APPLICATIONS

This application claims priority to International Application PCT/US2006/039181, with an international filing date of Oct. 6, 2006, which, in turn, claims the benefit of U.S. Provisional Application No. 60/723,917, filed Oct. 6, 2005, and U.S. Provisional Application No. 60/808,106, filed May 25, 2006. Contents of applications PCT/US2006/039181, U.S. Ser. No. 60/723,917, and U.S. Ser. No. 60/808,106 are herein incorporated by reference in their entireties.

FIELD OF INVENTION

This application relates to the design and use of vascular endothelial growth factor (VEGF) analogs as VEGF receptor antagonists to inhibit or reduce angiogenesis for the treatment of conditions and diseases associated with angiogenesis. The application also discloses VEGF analogs that exhibit increased receptor binding affinity to native receptors such as KDR.

DESCRIPTION OF THE TEXT FILE SUBMITTED ELECTRICALLY

The contents of the text file submitted electronically herewith are incorporated herein by reference in their entirety: A computer readable format copy of the Sequence Listing (filename: TROP__005__02US_Seqlist.ST25.txt, date recorded: May 11, 2010, file size 147 kilobytes).

BACKGROUND OF INVENTION

Vascular endothelial growth factors (VEGFs) regulate blood and lymphatic vessel development. They are predominantly produced by endothelial, hematopoietic and stromal cells in response to hypoxia and stimulation with growth factors such as transforming growth factors, interleukins and platelet-derived growth factor.

In mammals, VEGFs are encoded by a family of genes and include VEGF-A, VEGF-B, VEGF-C, VEGF-D and Placenta like Growth Factor (PlGF). Highly related proteins include orf virus-encoded VEGF-like proteins referred to as VEGF-E and a series of snake venoms referred to as VEGF-F. VEGFs and VEGF-related proteins are members of the Platelet Derived Growth Factor (PDGF) supergene family of cystine knot growth factors. All members of the PDGF supergene family share a high degree of structural homology with PDGF (see U.S. patent application Ser. No. 09/813,398 which is herein incorporated by reference in its entirety).

VEGF-A, VEGF-B and PlGF are predominantly required for blood vessel formation, whereas VEGF-C and VEGF-D are essential for the formation of lymphatic vessels. Angiogenesis is the process by which new blood vessels or lymphatic vessels form by developing from pre-existing vessels. The process is initiated when VEGFs bind to receptors on endothelial cells, signaling activation of endothelial cells. Activated endothelial cells produce enzymes which dissolve tiny holes in the basement membrane surrounding existing vessels. Endothelial cells then begin to proliferate and migrate out through the dissolved holes of the existing vessel to faun new vascular tubes (Alberts et al., 1994, Molecular Biology of the Cell. Garland Publishing, Inc., New York, N.Y. 1294 pp.).

Three type III receptor tyrosine kinases are activated by VEGFs during angiogenesis: fms-like tyrosine kinase (Flt-1, also known as VEGFR1), kinase domain receptor or kinase insert domain-containing receptor (KDR, also known as VEGFR2 and Flk-1) and Flt-4 (also known as VEGFR3). KDR is the predominant receptor in angiogenic signaling, whereas Flt-1 is associated with the regulation of blood vessel morphogenesis and Flt-4 regulates lymphangiogenesis. These receptors are expressed almost exclusively on endothelial cells, with a few exceptions such as the expression of Flt-1 in monocytes where it mediates chemotaxis (Barleon et al., 1996, Blood. 87: 3336-3343).

VEGF receptors are closely related to Fms, Kit and PDGF receptors. They consist of seven extracellular immunoglobulin (Ig)-like domains, a transmembrane (TM) domain, a regulatory juxtamembrane domain, an intracellular tyrosine kinase domain interrupted by a short peptide, the kinase insert domain, followed by a sequence carrying several tyrosine residues involved in recruiting downstream signaling molecules. Mutation analysis of the extracellular domains of Flt-1 and KDR show that the second and third Ig-like domains constitute the high-affinity ligand-binding domain for VEGF with the first and fourth Ig domains apparently regulating ligand binding and receptor dimerization, respectively (Davis-Smyth et al., 1998, J. Biol. Chem. 273: 3216-3222; Fuh et al., 1998, J. Biol. Chem. 273: 11197-11204; and Shinkai et al., 1998, J. Biol. Chem. 273: 31283-31288). Receptor tyrosine kinases are activated upon ligand-mediated receptor dimerization (Hubbard, 1991, Prog. Biophys. Mol. Biol. 71: 343-358; Jiang and Hunter, 1999, Curr. Biol. 9: R568-R571; and Leminon and Schlessinger, 1998, Methods Mol. Biol. 84: 49-71). Signal specificity of VEGF receptors is further modulated upon recruitment of coreceptors, such as neuropilins, heparin sulfate, integrins or cadherins.

VEGF molecules interact with one or more tyrosine kinase receptors during angiogenesis. For instance, VEGF-A acts predominantly through KDR and Flt-1. VEGF-C and VEGF-D similarly are specific ligands for KDR and VEGFR3. PlGF and VEGF-B are believed to bind only to Flt-1. Viral VEGF-E variants activate KDR. VEGF-F variants interact with either VEGFR3 or KDR.

In addition to the two classical receptors, there are several membrane or soluble receptors modulating VEGF bioactivity and angiogenesis. For instance, neuropilin-1 and neuropilin-2 interact with both KDR and Flt-1, respectively, stimulating signaling of those receptors. Isoforms of VEGF-A, VEGF-B, PlGF-2 have been shown to bind to neuropilin-1 (Soker et al., 1998, Cell. 92: 735-745; Makinen et al., 1999, J. Biol. Chem. 274: 21217-21222; and Migdal et al., 1998, J. Biol. Chem. 273: 22272-22278). VEGF isoforms capable of interacting of interacting with neuropilin, i.e., those isoforms with exon 7 or 6 and 7, are also capable of interacting with heparin sulfate.

Although VEGF-A is the best characterized of the VEGF proteins, the molecular basis of the interaction between VEGF-A and KDR and Flt-1 is not well understood. Although VEGFR1 binds VEGF-A with a 50-fold higher affinity than KDR, KDR is considered to be the major transducer of VEGF-A angiogenic effects, i.e., mitogenicity, chemotaxis and induction of tube formation (Binetruy-Tourniere et al., supra). There is, however, growing evidence that Flt-1 has a significant role in hematopoiesis and in the recruitment of monocytes and other bone-marrow derived cells that may home in on tumor vasculature and promote angiogenesis (Hattori et al., 2002, Nature Med. 8: 841-849; Gerber et al., 2002, Nature. 417: 954-958; and Luttun et al., 2002, Nature Med. 8: 831-840). Further, in some cases Flt-1 is expressed by tumor cells and may mediate a chemotactic signal, thus potentially extending the role of this receptor in cancer growth (Wey et al., 2005, Cancer. 104: 427-438).

A single VEGF-A homodimer induces dimerization of two KDR receptors and autophosphorylation of their cytoplasmatic portions. Previous studies suggested that by analogy to glycoprotein hormones, the charged amino acid residues in the peripheral loops of VEGF-A are also critical in providing high affinity electrostatic interactions with its respective receptors (Szkudlinski et al., 1996, Nat. Biotechnol. 14(10): 1257-63; Fuh et al., supra; Muller et al., 1997, Proc. Natl. Acad. Sci. U.S.A. 94(14): 7192-7; Keyt et al., 1996, J. Biol. Chem. 271(10): 5638-46). However, it should be noted that many mutations in VEGF-A have no major effect on receptor binding affinity. Mutations in the peripheral loops of VEGF primarily have resulted in loss-of-function. Further, there appear to be no previous amino acid substitutions increasing binding affinity to KDR more than 2-fold.

Angiogenesis is responsible for beneficial biological events such as wound healing, myocardial infarction repair, and ovulation. On the other hand, angiogenesis is also responsible for causing or contributing to diseases such as growth and metastasis of solid tumors (Isayeva et al., 2004, Int. J. Oncol. 25(2):335-43; Takeda et al., 2002, Ann Surg. Oncol. 9(7):610-16); atherosclerosis; abnormal neovascularization of the eye as seen in diseases such as retinopathy of prematurity, diabetic retinopathy, retinal vein occlusion, and age-related macular degeneration (Yoshida et al., 1999, Histol Histopathol. 14(4):1287-94; Aiello, 1997, Ophthalmic Res. 29(5):354-62); chronic inflammatory conditions such as rheumatoid arthritis osteoarthritis, and septic arthritis; neurodegenerative disease (Ferrara, N., 2004, Endocr. Rev. 25: 581-611); placental insufficiency, i.e., preeclampsia (Ferrara, supra); and skin diseases such as dermatitis, psoriasis, warts, cutaneous malignancy, decubitus ulcers, stasis ulcers, pyogenic granulomas, hemangiomas, Kaposi's sarcoma, hypertrophic scars, and keloids (Arbiser, 1996, J. Am. Acad. Dermatol. 34(3):486-97). During rheumatoid arthritis, for example, endothelial cells become activated and express adhesion molecules and chemokines, leading to leukocyte migration from the blood into the tissue. Endothelial cell permeability increases, leading to edema formation and swelling of the joints (Middleton et al., 2004, Arthritis Res. Ther. 6(2):60-72).

VEGF, in particular VEGF-A, has been implicated in many of the diseases and conditions associated with increased, decreased, and/or dysregulated angiogenesis (Binetruy-Toumiere et al., 2000, EMBO J. 19(7): 1525-33). For instance, VEGF has been implicated in promoting solid tumor growth and metastasis by stimulating tumor-associated angiogenesis (Lu et al., 2003, J. Biol. Chem. 278(44): 43496-43507). VEGF is also a significant mediator of intraocular neovascularization and permeability. Overexpression of VEGF in transgenic mice results in clinical intraretinal and subretinal neovascularization, and the formation of leaky intraocular blood vessels detectable by angiography, as seen in human eye disease (Miller, 1997, Am. J. Pathol. 151(1): 13-23). Additionally, VEGF has been identified in the peritoneal fluid of women with unexplained infertility and endometriosis (Miedzybrodzki et al., 2001, Ginekol. Pol. 72(5): 427-430), and the overexpression of VEGF in testis and epididymis has been found to cause infertility in transgenic mice (Korpelainen et al., 1998, J. Cell Biol. 143(6): 1705-1712). Recently, VEGF-A has been identified in the synovial fluid and serum of patients with rheumatoid arthritis (RA), and its expression is correlated with disease severity (Clavel et al., 2003, Joint Bone Spine. 70(5): 321-6). Given the involvement of pathogenic angiogenesis in such a wide variety of disorders and diseases, inhibition of angiogenesis, and particularly of VEGF signaling, is a desirable therapeutic goal.

Inhibition of angiogenesis and tumor inhibition has been achieved by using agents that either interrupt VEGF-A and KDR interaction and/or block the KDR signal transduction pathway including: peptides that block binding of VEGF to KDR (Binetruy-Tourniere et al., 2000, EMBO J. 19(7): 1525-33); antibodies to VEGF (Kim et al., 1993, Nature 362, 841-844; Kanai et al., 1998, J. Cancer 77, 933-936; Margolin et al., 2001, J. Clin. Oncol. 19, 851-856); antibodies to KDR (Lu et al., 2003, supra; Zhu et al., 1998, Cancer Res. 58, 3209-3214; Zhu et al. 2003, Leukemia 17, 604-611; Prewett et al., 1999, Cancer Res. 59, 5209-5218); soluble receptors (Holash et al., 2002, Proc. Natl. Acad. Sci. USA 99, 11393-11398; Clavel et al. supra); tyrosine kinase inhibitors (Fong et al., 1999, Cancer Res. 59, 99-106; Wood et al., 2000, Cancer Res. 60, 2178-2189; Grosios et al., 2004, Inflamm Res. 53(4):133-42); anti-VEGF immunotoxins (Olson et al., 1997, Int. J. Cancer 73, 865-870); ribozymes (Pavco et al., 2000, Clin. Cancer Res. 6, 2094-2103); antisense mediated VEGF suppression (Forster et al., 2004, Cancer Lett. 20; 212(1):95-103); RNA interference (Takei et al., 2004, Cancer Res. 64(10):3365-70; Reich et al., 2003, Mol. Vis. 9:210-6); and undersulfated, low molecular weight glycol-split heparin (Pisano et al., 2005, Glycobiology. 15(2) 1-6). Some of these treatments, however, have resulted in undesirable side effects. For instance, Genentech's Avastin, a monoclonal antibody that targets VEGF, has been reported to cause an increase in serious arterial thromboembolic events in some colon cancer patients and serious, and in some cases even fatal, hemoptysis in non-small cell lung cancer patients (Ratner, 2004, Nature Biotechnol. 22(10):1198). More recently, Genentech has reported that gastrointestinal perforations were observed in 11% of ovarian cancer patients (5 women out of 44 in trial) treated with Avastin (Genentech Press Release dated Sep. 23, 2005). Similarly, the first VEGF-targeting drug, Pfizer's receptor tyrosine kinase inhibitor SU5416, exhibited severe toxicities that included thromboembolic events, prompting Pfizer to discontinue development (Ratner, supra). Given the wide variety of patients that stand to benefit from the development of effective anti-angiogenic treatments and the drawbacks of some known anti-angiogenesis treatments, there remains a need for novel anti-angiogenic therapeutics.

SUMMARY OF INVENTION

This invention encompasses VEGF analogs and nucleic acids encoding the same, which exhibit strong binding affinity for one or more native VEGF receptors compared to wild-type VEGF. The invention also encompasses VEGF analogs and nucleic acids encoding same, which exhibit a dissociation of receptor binding affinity and bioactivity. Specifically, the in vivo and in vitro bioactivities of the disclosed analogs are substantially decreased compared to wild-type VEGF, whereas the binding affinity to one or more native receptors is about the same or substantially increased compared to wild-type VEGF. The VEGF analogs may demonstrate at least about a three to four fold increase in receptor binding affinity to a native receptor such as KDR.

In one embodiment of the invention, the VEGF analogs are modified VEGF homodimers or heterodimers. These molecules contain at least one mutation which can be present in one or both subunits of the VEGF molecule. In one embodiment of the invention, the VEGF analog containing the one or more mutations is VEGF-A. The VEGF-A analog can be any VEGF-A isoform, for instance, an isoform of 121, 145, 148, 165, 183, 189, or 206 amino acids. In one embodiment, the VEGF-A analog of the invention is a $VEGF_{165}b$ isoform. In another embodiment, the VEGF molecule containing one or more mutations is VEGF-B, VEGF-C, VEGF-D or PlGF.

The present invention includes a VEGF fusion protein containing one or more mutations in one or more subunits. The VEGF fusion protein of the invention includes at least one VEGF subunit, i.e., subunit, fused to at least one subunit of a different protein, including, but not limited to, other cystine knot growth factors or glycoproteins. For instance, the invention includes a chimera VEGF analog in which the VEGF molecule contains a VEGF-A subunit fused to a VEGF-B, VEGF-C, VEGF-D, VEGF-E, VEGF-F, PDGF or PlGF subunit; a VEGF-B subunit fused to a VEGF-A, VEGF-C, VEGF-D, VEGF-E, VEGF-F, PDGF or PlGF subunit; a VEGF-C subunit fused to a VEGF-A, VEGF-B, VEGF-D, VEGF-E, VEGF-F, PDGF or PlGF subunit; a VEGF-D subunit fused to a VEGF-A, VEGF-B, VEGF-C, VEGF-E, VEGF-F, PDGF or PlGF subunit; or a PlGF subunit fused to a VEGF-A, VEGF-B, VEGF-C, VEGF-D, VEGF-E, VEGF-F, or PDGF subunit. The subunits may optionally be separated by a linker peptide. The invention also includes different isoforms of the same VEGF fused together, e.g., $VEGF_{165}$ subunit fused to $VEGF_{165}b$.

In one embodiment, the VEGF analog is a single chain molecule. For instance, the VEGF analog of the invention includes two VEGF subunits, i.e., monomers, linked together via a linker peptide. One or both linked subunits can contain one or more basic amino acid substitutions. Further, the linked subunits can be different VEGF protein subunits and can be different isoforms of the same subunit. For instance, the present invention includes a wild-type $VEGF_{165}$ subunit linked via a GS linker to a $VEGF_{165}$ subunit with a I83K amino acid substitution.

In another embodiment of the invention, a VEGF-A, VEGF-B, VEGF-C, VEGF-D, or PlGF subunit or dimer comprising one or more mutations is fused to a toxin. The peptide of this embodiment can be useful for the targeting and destruction of tumor cells.

The VEGF analogs of the invention include one or more basic amino acid substitutions, such as lysine or arginine, from the group of positions 44, 67, 72, 73, 83, and 87. In one embodiment of the invention, the VEGF analog contains a basic amino acid substitution at position 83 and optionally one or more basic amino acid substitutions at positions 44, 67, 72 and 73. For instance, the invention includes a VEGF analog with a I83K mutation. The invention also includes, for instance, a VEGF analog with basic amino acids at positions 72, 73 and 83.

VEGF analogs with the basic amino acid substitutions described herein may contain additional amino acid substitutions to further increase receptor binding affinity to KDR and/or decrease receptor binding affinity to neuropilin-1. For instance, the invention includes mutations at positions 146 and 160 in the which act to disrupt the neuropilin-1 binding site.

Analogs of the invention can also contain additional amino acid substitutions which confer enhanced stability and increased serum half-life. For instance, the invention includes amino acids substitutions which eliminate proteolytic cleavage sites such substitutions at positions 111 and 148.

The VEGF receptor antagonists of the present invention can exhibit increased plasma half-life as compared to wild-type VEGF. This may be accomplished by further modifying a VEGF analog by methods known in the art to increase half-life or, alternatively, increased plasma half-life may be an inherent characteristic of a VEGF analog. The VEGF receptor antagonists of the invention can also exhibit an increase in rate of absorption and/or decreased duration of action compared to wild-type VEGF.

The modified analogs of the invention act as VEGF receptor antagonists and thus provide a long awaited solution for patients suffering from a wide spectrum of diseases and conditions associated with angiogenesis. The VEGF receptor antagonists can be administered to a patient alone or in conjunction with another VEGF receptor antagonist, an anti-cancer drug, or an anti-angiogenesis drug for the treatment of disease associated with angiogenesis, including but not limited to, solid tumor cancers, hemangiomas, rheumatoid arthritis, osteoarthritis, septic arthritis, asthma, atherosclerosis, idiopathic pulmonary fibrosis, vascular restenosis, arteriovenous malformations, meningiomas, neovascular glaucoma, psoriasis, Kaposi's Syndrome, angiofibroma, hemophilic joints, hypertrophic scars, Osler-Weber syndrome, pyogenic granuloma, retrolental fibroplasias, scleroderma, trachoma, von Hippel-Lindau disease, vascular adhesion pathologies, synovitis, dermatitis, neurological degenerative diseases, preeclampsia, unexplained female infertility, endometriosis, unexplained male infertility, pterygium, wounds, sores, skin ulcers, gastric ulcers, and duodenal ulcers.

DETAILED DESCRIPTION OF THE INVENTION

Figure 1A:
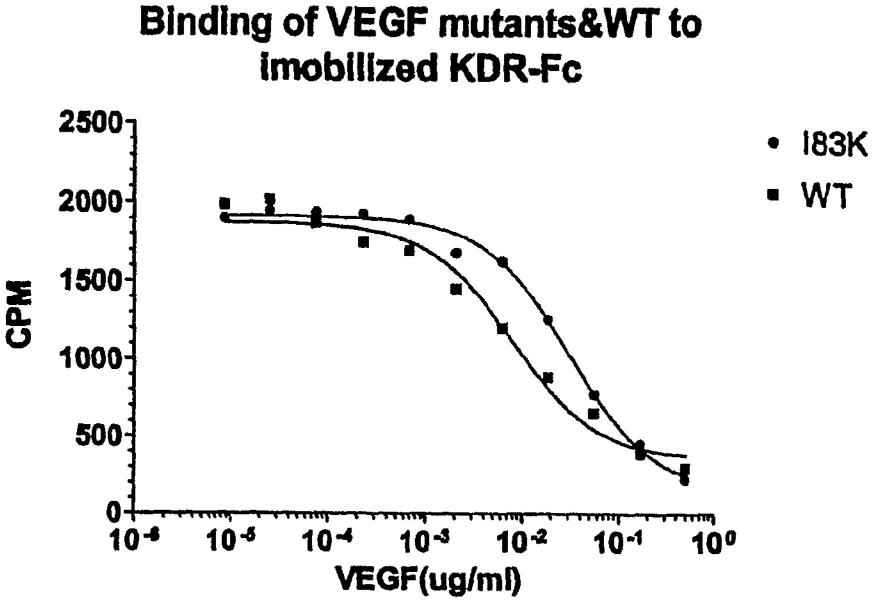
FIG. 1A is a graph comparing binding of the I83K mutant and wild-type VEGF-A to KDR.

The present invention provides modified angiogenic growth factors of the vascular endothelial growth factor (VEGF) family which exhibit surprising activity as VEGF receptor antagonists. As VEGF receptor antagonists, the compounds of the invention have "anti-angiogenic" properties. Being "modified" means that, while the protein contains an amino acid sequence which differs from a wild-type VEGF of interest, i.e., human VEGF or animal VEGF, the sequence has not been changed such that it is identical to the known VEGF sequence of other species. The terms "mutated" and "substituted" are used interchangeably herein to refer to modified amino acid residues. The terms "modified VEGF molecules", "modified VEGF proteins", "VEGF analogs", "VEGF receptor antagonists", "VEGF chimeras", "VEGF fusion proteins" and "VEGF single chain molecules" are used interchangeably herein to refer to modified VEGF-A, VEGF-B, VEGF-C, VEGF-D, and PlGF analog molecules.

"Antagonists" are used interchangeably herein to refer to molecules which act to block, inhibit or reduce the natural, biological activities of VEGF, such as the induction of angiogenesis. The term "anti-angiogenic" as used herein means that the modified VEGF molecules of the invention block, inhibit or reduce the process of angiogenesis, or the process by which new blood or lymphatic vessels form from pre-existing vessels. The activities of the VEGF analogs of the invention disrupt normal VEGF/receptor signaling which usually occurs when VEGF binds to a receptor. Accordingly, the analogs of the invention are VEGF receptor antagonists. Without wishing to be bound by a theory, it is believed that the VEGF analogs of the invention disrupt the dimerization of KDR necessary for signaling.

Inhibition of angiogenesis may be complete or partial. The VEGF receptor antagonist may inhibit angiogenesis at least about 5%, at least about 10%, at least about 20%, at least about 25%, at least about 30%, at least about 40%, at least about 50%, at least about 60%, at least about 70%, at least about 80%, at least about 90%, and at least about 100% in vitro and in vivo. Inhibition of angiogenesis can be measured by a skilled artisan by methods known in the art. The determination of inhibition of angiogenesis can include the use of negative and/or positive controls. For instance, a skilled artisan can conclude that a VEGF analog of the invention inhibits VEGF-induced angiogenesis by comparing angiogenesis in a subject treated with a VEGF analog of the invention to a similar subject not treated with a VEGF analog.

The modified VEGF molecules of the invention display increased receptor binding affinity or similar receptor binding affinity to one or more native VEGF receptors compared to that of wild-type VEGF. As used herein, a native VEGF receptor is an unmodified receptor that specifically interacts with VEGF. For instance, an endogenous VEGF receptor is a native VEGF receptor. In one embodiment of the invention, the native receptor is KDR. KDR is a receptor of VEGF-A, VEGF-C, VEGF-D, VEGF-E and VEGF-F. In another embodiment, the native receptor is Flt-1. Flt-1 is a receptor of VEGF-A, VEGF-B and PlGF.

"Receptor binding affinity" refers to the ability of a ligand to bind to a receptor in vivo or in vitro and can be assessed by methods readily available in the art including, but not limited to, competitive binding assays and direct binding assays. As used herein, receptor binding affinity refers to the ability of VEGF molecules to bind to native VEGF receptors, including, but not limited to, Flt-1 (also known as VEGF-R1), KDR (also known as VEGF-R2) and Flt-4 (also known as VEGF-R3). For instance, the modified VEGF-A molecules of the invention display increased binding receptor affinity or similar binding affinity to KDR compared to wild-type VEGF-A. In one embodiment, the increase in receptor binding affinity of the modified VEGF molecules of the invention is at least about 1.25 fold, at least about a 1.5 fold, at least about a 1.75 fold, at least about 2 fold, at least about 3 fold, at least about 4 fold, at least about 5 fold, at least about 6 fold, at least about 7 fold, at least about 8 fold, at least about 9 fold or at least about 10 fold greater than that of wild-type VEGF.

In another embodiment, the modified VEGF exhibits a receptor binding affinity to KDR and/or other receptor that is involved in angiogenesis that is similar or comparable to that of wild-type VEGF. Similar or comparable receptor binding affinity is at least about 75%, at least about 80%, at least about 85%, at least about 90%, at least about 95%, or at least about 97% or more of that of wild-type VEGF. For instance, the invention includes VEGF-A analogs exhibiting about 75% to 85%, about 85% to 95% and about 95% to 100% the receptor binding affinity exhibited by wild-type VEGF.

The present invention also includes VEGF analogs which display increased or similar receptor binding affinity to at least one native receptor but display decreased receptor binding affinity to another native receptor. For instance, VEGF-A analogs of the invention may display increased or similar receptor binding affinity to KDR compared to wild-type VEGF-A, but may display decreased receptor binding affinity to Flt-1, neuropilin-1 or neuropilin-2 compared to wild-type VEGF-A.

The VEGF analogs of the invention also display a decrease in bioactivity compared to wild-type VEGF. "Bioactivity" refers to the natural, biological activities of VEGF in vivo and in vitro, including, but not limited to, the ability of VEGF to induce cell proliferation in endothelial cells. A decrease in bioactivity results in a decrease in angiogenesis. In one embodiment of the invention, the VEGF analogs of the invention display a decrease in bioactivity compared to wild-type VEGF of the same isoform. For instance, a $VEGF_{165}$ analog of the invention can display a decrease in bioactivity compared to wild-type $VEGF_{165}$, and a $VEGF_{165}$b analog can display a decrease in bioactivity compared to wild-type $VEGF_{165}$b.

Bioactivity can be assessed by several methods known in the art, including, but not limited to, in vitro cell viability assays which assay the viability of endothelial cells such as human umbilical vein endothelial cells (HUVEC) upon exposure to VEGF. A decrease in endothelial cell viability of at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or more compared to resulting from exposure to wild-type VEGF is indicative of a decrease in bioactivity.

Bioactivity can be assessed in vivo as well. For instance, bioactivity can be assessed in vivo in a subject with a tumor by detecting a lack of increase in angiogenesis around a tumor. The detection of a lack of increase in angiogenesis can be accomplished by several methods known in the art including, but not limited to, an in vivo matrigel migration assay, a disc angiogenesis assay, an assay comprising a dorsal skinfold chamber in mice, a corneal transplant and a sponge implant model of angiogenesis. In one embodiment, angiogenesis is assessed by comparing angiogenesis of and around the tumor to that of a tumor of similar type, size and location in an untreated subject. Biopsy methods as known in the art can be used to extract tissue and analyze for vessel formation.

"Dissociation" of receptor binding affinity and bioactivity refers to the concept that receptor binding affinity and bioactivity are not correlated. In comparison, receptor binding affinity and bioactivity are correlated for wild-type VEGF proteins such as wild-type VEGF-A. An increase in receptor binding ability, for example, would be expected to result in an increase in bioactivity for wild-type VEGF-A. On the other hand, the modified VEGF molecules of the invention demonstrate a similar receptor binding affinity or an increase in receptor binding affinity as compared to wild-type VEGF but a decrease in bioactivity as compared to wild-type VEGF.

Mammalian VEGFs are produced in multiple isoforms due to alternative splicing of a family of related genes. The present invention describes VEGF analogs which correspond to VEGF isoforms involved in angiogenesis. The VEGF analogs of the present invention can be created using any VEGF isoform unless otherwise indicated.

VEGF-A can exist in isoforms including, but not limited to, 121, 145, 148, 165, 183, 189, and 206 amino acids, respectively. The three main mRNA species are $VEGF_{121}$, $VEGF_{165}$ and $VEGF_{189}$. As used herein, $VEGF_{121}$ (SEQ ID NO.: 6), $VEGF_{145}$ (SEQ ID NO.: 8), $VEGF_{148}$ (SEQ ID NO.: 10), $VEGF_{165}$ (SEQ ID NO.: 4), $VEGF_{165}$b (SEQ ID NO.: 13), $VEGF_{183}$ (SEQ ID NO.: 15), $VEGF_{189}$ (SEQ ID NO.: 17) and $VEGF_{206}$ (SEQ ID NO.: 19) are isoforms of VEGF-A capable of being modified to possess anti-angiogenic properties. The amino acid positions described herein are based on a VEGF molecule lacking a leader sequence such as the leader sequence of SEQ ID NO.: 3. The amino acid sequences of VEGF-A isoforms with leader sequence are the sequences of SEQ ID NOs.: 2, 5, 7, 9, 12, 14, 16 and 18.

The various isoforms of VEGF-A share a common amino-terminal domain consisting of 110 amino acids. VEGF-A isoforms have a receptor binding domain encoded by exons 2-5. The most notable difference between the isoforms are found in the neuropilin and heparin binding domains which are encoded by exons 6a, 6b, 7a and 7b.

The most common VEGF-A isoform is $VEGF_{165}$. The nucleic acid encoding $VEGF_{165}$ is the sequence of SEQ ID NO.: 1. Recently, an endogenous splice variant referred to as $VEGF_{165}$b was described which contains sequences encoded by exon 9, instead of exon 8, at the carboxy terminus. The nucleic acid molecule encoding this protein is the sequence of SEQ ID NO.: 11. $VEGF_{165}$b (SEQ ID NO.: 12 with leader sequence; SEQ ID NO.: 13 without leader sequence) inhibited VEGF signaling in endothelial cells when added with $VEGF_{165}$ (see Woolard et al., 2004, Cancer Research. 64: 7822-7835; see also U.S. 2005/0054036 which is herein incorporated by reference in its entirety).

In one embodiment of the invention, the VEGF analogs are VEGF-A analogs. VEGF-A analogs include "modified VEGF-A proteins", "VEGF-A receptor antagonists", "VEGF-A chimeras", "VEGF-A fusion proteins" and "VEGF-A single chain molecules." A VEGF-A analog is a VEGF-A molecule containing at least one modified VEGF-A subunit.

VEGF-B exists in two isoforms, VEGF-$B_{167}$ (SEQ ID NO.: 48) and VEGF-$B_{186}$ (SEQ ID NO.: 50) (Makinen et al., 1999, J. Biol. Chem. 274: 21217-21222). In one embodiment of the invention, the VEGF analog is a VEGF-B analog. VEGF-B analogs include "modified VEGF-B proteins", "VEGF-B analogs", "VEGF-B receptor antagonists", "VEGF-B chimeras", "VEGF-B fusion proteins" and "VEGF-B single chain molecules." A VEGF-B analog is a VEGF-B molecule containing at least one modified VEGF-B subunit.

VEGF-C is produced as a propeptide (SEQ ID NO.: 51) that is proteolytically cleaved to form a 21-kd active protein (Nicosia, 1998, Am. J. Path. 153: 11-16). In one embodiment of the invention, the VEGF analog is a VEGF-C analog. VEGF-C analogs include "modified VEGF-C proteins", "VEGF-C analogs", "VEGF-C receptor antagonists", "VEGF-C chimeras", "VEGF-C fusion proteins" and "VEGF-C single chain molecules." A VEGF-C analog is a VEGF-C molecule containing at least one modified VEGF-C subunit.

VEGF-D is also produced as a propeptide (SEQ ID NO.: 52) that is proteolytically cleaved to form an active protein. VEGF-D is 48% identical to VEGF-C (Nicosia, supra). In one embodiment of the invention, the VEGF analog is a VEGF-D analog. VEGF-D analogs include "modified VEGF-D proteins", "VEGF-D analogs", "VEGF-D receptor antagonists", "VEGF-D chimeras", "VEGF-D fusion proteins" and "VEGF-D single chain molecules." A VEGF-D analog is a VEGF-D molecule containing at least one modified VEGF-D subunit.

Placenta growth factor (PlGF) exists in three isoforms, PlGF-1 (SEQ ID NO.: 54), PlGF-2 (SEQ ID NO.: 56) and PlGF-3 (SEQ ID NO.: 58). PlGF-2 contains an exon 6 encoded peptide which bestows heparin and neuropilin-1 binding properties absent in the other two isoforms. Both PlGF-1 and PlGF-2 have been reported as being capable of inducing endothelial cell migration (Migdal et al., 1998, J. Biol. Chem. 273: 22272-22278). In one embodiment of the invention, the VEGF analog is a PlGF analog. In another embodiment, the VEGF analog is PlGF-1 or PlGF-2. PlGF analogs include "modified PlGF proteins", "PlGF analogs", "PlGF receptor antagonists", "PlGF chimeras", "PlGF fusion proteins" and "PlGF single chain molecules." PlGF analogs are PlGF molecules with at least one modified PlGF subunit.

The VEGF analogs of the invention are modified animal or human VEGF molecules. In one embodiment of the invention, the VEGF analogs are mammalian VEGF molecules. In another embodiment of the invention, the VEGF analogs are avian VEGF molecules. The VEGF analogs of the present invention include, but are not limited to, modified primate, canine, feline, bovine, equinine, porcine, ovine, murine, rat and rabbit VEGF molecules. In one embodiment, the animal VEGF analog is a VEGF-A analog. For instance, the animal VEGF-A analog of the invention can be an animal $VEGF_{165}$ or $VEGF_{165}$b analog.

The modified VEGF molecules of species other than human have substitutions at positions corresponding to those in the modified human VEGF molecules disclosed herein and may be identified using any alignment program, including but not limited to DNASIS, ALIONment, SIM and GCG programs such as Gap, BestFit, FrameAlign, and Compare. As can be appreciated by one of skill in the art, the corresponding amino acid to be replaced with a basic amino acid may not be identical to the one in human VEGF-A. For instance, a skilled artisan would appreciate that a glutamate (E) may correspond to a different acidic amino acid in an animal such as aspartate (D).

In another embodiment, the corresponding amino acid is identified as being located in the same general position within a defined structure, for instance, on an outer loop structure. The structure of a protein can be predicted using software based on the amino acids of the protein. Accordingly, one of skill in the art can use software that predicts protein folding and loop structure to identify the corresponding position in a related protein.

Design of VEGF Receptor Antagonists

The VEGF receptor antagonists encompassed by the present invention may be designed by comparing the amino acid sequences of the VEGF of interest to that of other species to identify basic residues in the proteins of VEGF of other species. For instance, a VEGF-A molecule of instance can be designed by comparing a human VEGF-A to that of another species. Such methods are disclosed in U.S. Pat. No. 6,361, 992, which is herein incorporated by reference in its entirety. Consideration may also be given to the relative biological activity of VEGF from various species as to which species to choose for comparison and amino acid substitution. Further homology modeling based on the structure of related glycoproteins is useful to identify surface-exposed amino acid residues. Homology modeling can be performed by methods generally know in the art, including, but not limited to, the use of protein modeling computer software.

The present invention also provides a modified VEGF protein, wherein the modified VEGF comprises an amino acid(s) substituted at a position(s) corresponding to the same amino acid position in a VEGF protein from another species having an increased binding affinity and/or decreased bioactivity over the wild-type VEGF. For example, snake venom VEGF-F binds to KDR with high affinity and strongly stimulates proliferation of vascular endothelial cells in vitro. One can compare human VEGF-A to snake venom VEGF, design human VEGF-A proteins with amino acid substitutions at one or more positions where the snake venom and human sequences differ, construct human VEGF-A proteins with the selected changes, and administer the modified human VEGF-A to humans. Although snake venom VEGF-F demonstrates an increase in KDR binding affinity and bioactivity, i.e., binding affinity and bioactivity are correlated, compared to human VEGF, one of skill in the art would understand that amino acid substitutions could be empirically tested to identify amino acid substitutions which increase receptor binding affinity but decrease or have no effect on bioactivity. An amino acid substitution which increases receptor binding affinity and/or decreases or has no effect on bioactivity may then be combined with one or more other amino acid substitutions known to increase receptor binding affinity and/or decrease bioactivity.

In another embodiment of the invention, the modified VEGF molecule can contain one or more amino acids substituted at a position(s) corresponding to the same amino acid position in a VEGF homolog that naturally exists in arthropods. In arthropods, a single growth factor performs the tasks performed by PDGF and VEGF in higher organisms. One of skill in the art would understand that amino acid substitutions could be empirically tested to identify amino acid substitutions which increase receptor binding affinity but decrease or have no effect on bioactivity, or, alternatively, have little effect on receptor binding affinity but decrease bioactivity.

Further, the present invention provides a modified VEGF, wherein the modified VEGF comprises a basic amino acid(s) substituted at a position(s) corresponding to the same amino acid in a different VEGF or VEGF isoform or closely related glycoprotein such as proteins in the PDGF family from the same species or different species. For example, $VEGF_{165}$ can be compared to PDGF from the same species and amino acid substitutions made to the VEGF protein based on any sequence divergence. A skilled artisan can compare two or more sequences of VEGF proteins or VEGF-related proteins using methods known in the art such as the use of alignment software, including but not limited to, DNASIS, ALIONment, SIM and GCG programs such as Gap, BestFit, FrameAlign, and Compare.

In another aspect of the invention, the amino acid substitutions described herein can be incorporated into closely related proteins such as VEGF-E (SEQ ID NO.: 60), VEGF-F (SEQ ID NO.: 62) and PDGF (SEQ ID NO.: 63 and SEQ ID NO.: 64). For instance, one or more basic amino acid substitutions selected from the group consisting of E67, E72, E73, 183 and Q87 can be compared to a PDGF isoform from the same species and amino acid substitutions made to the PDGF isoform.

The VEGF analogs of the invention may be designed to display a decreased receptor binding affinity to Flt-1 receptors compared to wild-type VEGF-A. Although these analogs display a decreased receptor binding affinity to Flt-1, they may have an increased or comparable receptor binding affinity to KDR compared to wild-type VEGF-A.

The VEGF analogs of the invention may be designed to display a decreased receptor binding affinity to co-receptors, including, but not limited to, neuropilin-1 or neuropilin-2 compared to that of wild-type VEGF. Analogs with decreased receptor binding affinity to neuropilin-1 or neuropilin-2 may have increased or similar receptor binding affinity to KDR, Flt-1 or VEGR3 compared to that of wild-type VEGF. For instance, VEGF-A analogs can be designed which exhibit decreased receptor binding affinity to neuropilin-1 and increased receptor binding affinity to KDR and/or Flt-1. In one embodiment of the invention, the VEGF-A displaying decreased receptor binding affinity to neuropilin-1 is an analog designed in the $VEGF_{165}$b splice variant. In another embodiment, $VEGF\text{-}B_{167}$ and PlGF-2 analogs can be designed which exhibit decreased receptor binding affinity to neuropilin-1 and increased binding affinity to Flt-1.

In one embodiment of the invention, VEGF analogs are designed to exhibit decreased receptor binding affinity to neuropilin-1 or neuropilin-2 compared to wild-type VEGF by disrupting the VEGF neuropilin binding site. This can be accomplished by reducing the number of cysteine amino acid residues in the neuropilin-1 receptor binding domain. For instance, $VEGF_{165}$ analogs can be designed to disrupt the neuropilin 1 binding site in $VEGF_{165}$ by substituting the cysteine residues at positions 146 and/or 160 of SEQ ID NO.: 4 with amino acids such as serine which cause a disruption of the disulfide bridge. The substitution of cysteine residues at positions 146 and 160 of SEQ ID NO.: 4 disrupts neuropilin-1 binding but does not disrupt heparin binding. Mutations at positions 146 and/or 160 can be coupled with one or more mutations to increase, maintain or restore receptor binding affinity to KDR, Flt-1 and/or VEGFR3 as described herein.

Similarly, the present invention includes VEGF analogs which exhibit decreased receptor binding affinity to neuropilin-2 compared to wild-type VEGF. For instance, the invention includes VEGF-C and VEGF-D analogs which exhibit reduced binding affinity to neuropilin-2 but increased or similar binding affinity to KDR and/or VEGFR3 compared to wild-type VEGF-C or VEGF-D, respectively.

The invention also includes VEGF analogs which exhibit enhanced stability and resistance to proteases. In one embodiment, amino acids substitutions at positions A111 and A148 of SEQ ID NO.: 4 are incorporated in a VEGF-A analog to improve resistance to proteases. The invention also includes VEGF-C and VEGF-D analogs which contain mutations preventing the cleavage of the VEGF-C propeptide or VEGF-D propeptide, respectively. For instance, the present invention includes VEGF-C and VEGF-D analogs that contain one or more mutations which induce resistance to serine protease plasmin and/or other members of the plasminogen family.

In another embodiment of the invention, VEGF analogs which exhibit increased receptor binding affinity to one or more VEGF receptors, preferably KDR, can be created in a naturally occurring VEGF molecule which exhibits antagonistic properties. For instance, $VEGF_{165}$b, an isoform isolated from kidney tissue, can be modified to incorporate the amino acid substitutions associated with an increase in receptor binding ability and decrease in bioactivity of the protein. Similarly, a skilled artisan could incorporate the amino acid substitutions of the present invention in synthetic or new isoforms of VEGF which contain the properties of $VEGF_{165}$b. In particular, the mutations of the invention can be used with other VEGF proteins which contain the amino acids SLTRKD (SEQ ID NO.: 70), i.e., the amino acids coded for by what has been termed exon 9, in addition to or in place of the amino acids coded for by exon 8 (CDKPRR; SEQ ID NO.: 71).

Amino Acid Substitutions

The VEGF analogs of the present invention contain one or more basic amino acid substitutions which confer enhanced receptor binding affinity and decreased bioactivity. In one embodiment of the invention, the VEGF analogs are VEGF receptor antagonists, including but not limited to VEGF-A antagonists.

A modified VEGF molecule of the invention may have a basic amino acid substitution in one or more subunits, i.e., monomers, of VEGF. Basic amino acids comprise the amino acids lysine (K), arginine (R) and histidine (H), and any other basic amino acids which may be a modification of any of these three amino acids, synthetic basic amino acids not normally found in nature, or any other amino acids which are positively charged at a neutral pH. Preferred amino acids, among others, are selected from the group consisting of lysine and arginine.

In one embodiment, a modified VEGF molecule of the invention comprises at least one modified subunit, wherein the modified subunit comprises a basic amino acid substitution at position I83 of wild-type human $VEGF_{165}$ (SEQ ID NO.: 4), $VEGF_{121}$ (SEQ ID NO.: 6), $VEGF_{145}$ (SEQ ID NO.: 8), $VEGF_{148}$ (SEQ ID NO.: 10), $VEGF_{165}$b (SEQ ID NO.: 13), $VEGF_{183}$ (SEQ ID NO.: 15), $VEGF_{189}$ (SEQ ID NO.: 17) or $VEGF_{206}$ (SEQ ID NO.: 19). For instance, the invention includes an I83K amino acid substitution in SEQ ID NOs.: 4, 6, 8, 10, 13, 15, 17 or 19 corresponding to the amino acid sequences of VEGF-A isoforms.

The invention also includes a basic amino acid substitution in the position corresponding to position 83 in other VEGF molecules, i.e., VEGF-B, VEGF-C, VEGF-D and PlGF, such as position I83 of VEGF-$B_{167}$ (SEQ ID NO.: 48) or VEGF-$B_{186}$ (SEQ ID NO.: 50) and position I91 of PlGF-1 (SEQ ID NO.: 54), PlGF-2 (SEQ ID NO.: 56) or PlGF-3 (SEQ ID NO.: 58).

The invention includes modified VEGF molecules in animals other than humans, wherein the VEGF molecule contains, in one or more subunits, a basic amino acid substitution in the position corresponding to position 83 in human VEGF-A. In one embodiment, the modified animal VEGF is a modified VEGF-A molecule. For instance, the present invention includes a basic amino acid substitution at position I83 in primate (SEQ ID NO.: 22), position I82 in bovine (SEQ ID NO.: 25), position I82 in canine (SEQ ID NO.: 28), position I83 in chicken (SEQ ID NO.: 31), position I82 in equine (SEQ ID NO.: I82), position I82 in murine (SEQ ID NO.: 37), position I82 in porcine (SEQ ID NO.: 40), position I82 of rat (SEQ ID NO.: 43) and position I82 in ovine (SEQ ID NO.: 46).

The invention also envisions a modified VEGF-related protein, including, but not limited to VEGF-E, VEGF-F and PDGF, containing an amino acid substitution corresponding to position I83 of SEQ ID NO.: 4. For instance, VEGF-F (SEQ ID NO.: 62) can be modified to include an I83 amino acid substitution.

The modified VEGF molecule of the invention can contain basic amino acid substitutions which further increase the binding affinity or decrease bioactivity of VEGF compared to wild-type VEGF such as wild-type VEGF-A. VEGF molecules with basic amino acid substitutions at one or more of positions 44, 67, 72, 73 and/or 87 of $VEGF_{165}$ (SEQ ID NO.: 4), $VEGF_{121}$ (SEQ ID NO.: 6), $VEGF_{145}$ (SEQ ID NO.: 8), $VEGF_{148}$ (SEQ ID NO.: 10), $VEGF_{165}$b (SEQ ID NO.: 13), $VEGF_{183}$ (SEQ ID NO.: 15), $VEGF_{189}$ (SEQ ID NO.: 17) and $VEGF_{206}$ (SEQ ID NO.: 19) can increase binding affinity for KDR compared to wild-type VEGF. For instance, the invention includes the basic amino acid modifications E44R, E44K, E72R, E72K, E73R, E73K, Q87R, Q87K and E67K.

In one embodiment of the invention, basic amino substitutions corresponding to positions 44, 67, 72, 73 and/or 87 of SEQ ID NO.: 4 are coupled with the basic amino acid substitution corresponding to position 83 of SEQ ID NO.: 4 to produce a VEGF receptor antagonists. For instance, the modified amino acids of the present invention include basic amino acid substitutions at positions 72+73+83, 44+83, 72+83, 73+83, 44+72+83, 44+73+83, 44+72+73+83, 44+83+87, 83+87, 67+72+73+83; 44+67+83, 67+72+83, 67+73+83, 44+67+72+83, 44+67+73+83, 44+67+72+73+83, 44+67+83+87 and 67+83+87.

In another embodiment of the invention, the analog is a $VEGF_{165}$b molecule containing one or more basic amino acids at positions E44, E67, E72, E73 and Q87 and optionally a basic amino acid substitution at position I83. When the VEGF-A isoform is VEGF165b, it is possible to generate a VEGF analog of the invention with increased binding affinity and decreased bioactivity compared to wild-type VEGF-A, including $VEGF_{165}$, by incorporating a single amino acid modification that would otherwise only result in an increase in receptor binding affinity in other $VEGF_{165}$.

As can be appreciated by a skilled artisan, the invention includes VEGF proteins and VEGF-related proteins other that VEGF-A that contain basic amino acid modifications corresponding to those of positions E44, E67, E72, E73 and/or Q87 of VEGF-A (SEQ ID NO.: 4). For instance, the invention includes a modified VEGF-B analog (SEQ ID NOs.: 48 and 50) containing one or more basic amino acid substitutions at positions A44, E67, G72, Q73 and S87 and a modified VEGF-F analog (SEQ ID NO.: 62) containing one or more basic amino acid substitutions at positions E44, E67, E72, E73 and Q87.

A modified animal, i.e., non-human, VEGF-A molecule of the invention can likewise contain additional amino acid modifications to increase binding affinity or decrease bioactivity of the modified animal VEGF molecule compared to wild-type animal VEGF. The invention includes the use of these modifications in conjunction with an amino acid substitution that corresponds to I83 of SEQ ID NO.: 4 as described above. For instance, the present invention includes one or more basic amino acid substitutions selected from the group of positions E44, E67, E72, E73, I83 and I87 of primate (long-tailed macaque) VEGF-A (SEQ ID NO.: 22); one or more basic amino acid substitutions selected from the group of positions E43, E66, E71, E72, I82 and Q86 of bovine VEGF-A (SEQ ID NO.: 25); one or more basic amino acid substitutions selected from the group of positions E43, E66, E71, E72, I82 and Q86 of canine VEGF-A (SEQ ID NO.: 28); one or more basic amino acid substitutions selected from the group of positions E44, E67, D72, V73, I83 and Q87 of avian (chicken) VEGF-A (SEQ ID NO.: 31); one or more basic amino acid substitutions selected from the group of positions E43, E66, A71, E72, I82 and Q86 of equine VEGF-A (SEQ ID NO.: 34); one or more basic amino acid substitutions selected from the group of positions E43, E66, S71, E72, I82 and Q86 of murine VEGF-A (SEQ ID NO.: 37); one or more basic amino acid substitutions selected from the group of positions E43, E66, E71, E72, I82 and Q86 of porcine VEGF-A (SEQ ID No.: 40); one or more basic amino acid substitutions selected from the group of positions E43, E66, S71, E72, I82 and Q86 of rat VEGF-A (SEQ ID NO.: 43); and one or more basic amino acid substitutions selected from the group of positions E43, E66, E71, E72, I82 and Q86 of ovine VEGF-A (SEQ ID NO.: 46).

VEGF analogs containing one or more basic amino acid substitutions can also be combined with amino acid substitutions designed to disrupt a co-receptor binding site. In one embodiment, the VEGF analogs of the invention contain a disrupted neuropilin-1 binding site. The neuropilin-1 binding site comprises amino acids 111 to 165 of $VEGF_{165}$ (SEQ ID NO.: 04). This domain overlaps the heparin binding domain encoded by exons 6 and 7. The invention includes any amino acid modifications in or near (i.e., within about 5 amino acids)

that disrupt the neuropilin-1 binding site domain but which do not disrupt the ability of the heparin binding domain to bind heparin sulfate. Such amino acid modifications can be determined empirically by a skilled artisan.

In one embodiment of the invention, the neuropilin-1 binding domain is disrupted by reducing the number of cysteine amino acid residues in the domain, i.e., by reducing the number of cysteine amino acid residues between amino acids 111 to 165 of VEGF-A. For instance, $VEGF_{165}$ analogs can be designed to disrupt the neuropilin 1 binding site by substituting the cysteine residues at positions 146 and/or 160 of SEQ ID NO.: 4 with amino acids such as serine which cause a disruption of the disulfide bridge. The substitution of cysteine residues at positions 146 and 160 of SEQ ID NO.: 4 disrupts neuropilin-1 binding but does not disrupt heparin binding. The neuropilin-1 binding site can also be disrupted by ending the amino acid peptide at position 146 or 160.

The invention can also included modifications of amino acids surrounding amino acids at positions 146 and 160 of SEQ ID NO.: 4 such that the cysteine residues of positions 146 and 160 are unable to form a disulfide bridge. For instance, the invention includes, but is not limited to, one or more amino acid substitutions at positions 136 through 165 which are capable of disrupting the formation of a disulfide bridge.

A modified VEGF analog of the invention containing one or more of the basic amino acid substitutions corresponding to E44, E67, E72, E73, I83 and Q87 of SEQ ID NO.: 4 described herein. For instance, the invention includes VEGF analogs with amino acid substitutions at positions E44B+C146X, E44B+C160X, E44B+C146X+C160X, E67B+C146X, E67B+C160X, E67B+C146X+C160X, E44B+E67B+C146X, E44B+E67B+C160X, E44B+E67B+C146X+C160X, E72B+C146X, E72B+C160X, E72B+C146X+C160X, E73B+C146X, E73B+C160X, E73B+C146X+C160X, E72B+E73B+C146X, E72B+E73B+C160X, E72B+E73B+C146X+C160X, I83B+C146X, I83B+C160X, I83B+C146X+C160X, Q87B+C146X, Q87B+C160X, Q87B+C146X+C160X, E44B+E67B+E72B+C146X, E44B+E67B+E72B+C160X, E44B+E67B+E72+C146X+C160X, E44B+E67B+E73B+C146X, E44B+E67B+E73B+C160X, E44B+E67B+E73B+C146X+C160X, E44B+E67B+E72B+E73B+C146X, E44B+E67B+E72B+E73B+C160X, E44B+E67B+E72B+E73B+C146X+C160X, E67B+E72B+E73B+C146X, E67B+E72B+E73B+C160X, E67B+E72B+E73B+C146X+C160X, E44B+E72B+E73B+C146X, E44B+E72B+E73B+C160X, E44B+E72B+E73B+C146X+C160X, E44B+I83B+C146X, E44B+I83B+C160X, E44B+I83B+C146X+C160X, E67B+I83B+C146X, E67B+I83B+C160X, E67B+I83B+C146X+C160X, E44B+E67B+I83B+C146X, E44B+E67B+I83B+C160X, E44B+E67B+I83B+C146X+C160X, E72B+I83B+C146X, E72B+I83B+C160X, E72B+I83B+C146X+C160X, E73B+I83B+C146X, E73B+I83B+C160X, E73B+I83B+C146X+C160X, E72B+E73B+I83B+C146X, E72B+E73B+I83B+C160X, E72B+E73B+I83B+C146X+C160X, I83B+Q87B+C146X, I83B+Q87B+C160X, I83B+Q87B+C146X+C160X, E44B+E67B+E72B+I83B+C146X, E44B+E67B+E72B+I83B+C160X, E44B+E67B+E72+183B+C146X+C160X, E44B+E67B+E73B+I83B+C146X, E44B+E67B+E73B+I83B+C160X, E44B+E67B+E73B+I83B+C146X+C160X, E44B+E67B+E72B+E73B+I83B+C146X, E44B+E67B+E72B+E73B+I83B+C160X, E44B+E67B+E72B+E73B+I83B+C146X+C160X, E67B+E72B+E73B+I83B+C146X, E67B+E72B+E73B+I83B+C160X, E67B+E72B+E73B+I83B+C146X+C160X, E44B+E72B+E73B+I83B+C146X, E44B+E72B+E73B+I83B+C160X and E44B+E72B+E73B+I83B+C146X+C160X, wherein B is a basic amino acid and X is any amino acid other than cysteine. In one embodiment, X is serine.

The modified proteins of the invention may also contain further substitutions, particularly conservative substitutions that do not alter the enhanced properties of the protein. Typically, however, such modified proteins will contain less than five substitutions at positions other than those listed above, and may exhibit complete amino acid sequence identity with the corresponding wild-type VEGF subunits in positions other that the positions listed above.

As can be appreciated by a skilled artisan, all amino acid substitutions and peptide modifications disclosed in the present invention can be incorporated in any VEGF protein or related protein, regardless of species, because of the high degree of homology between VEGF proteins and related proteins. A skilled artisan can correlate the amino acid substitutions described herein using methods known in the art, including, but not limited to, the use of amino acid sequence alignment software.

VEGF Analogs with Increased Serum Half-Life

The VEGF analogs of the invention may have an increased plasma half-life as compared to wild-type VEGF. In one embodiment, the modification(s) which increases or maintains receptor binding affinity and decreases bioactivity as compared to wild-type VEGF also increases the plasma half-life of the VEGF as compared to wild-type VEGF. In another embodiment, the modified VEGF proteins of the invention are further modified such that the plasma half-life is increased as compared to wild type VEGF.

There are many modifications known in the art that can be used to increase the half-life of proteins, in particular glycoproteins. For instance, the modified VEGF proteins of the invention may further comprise at least one sequence with a potential glycosylation site including sequences comprising N-glycosylation and/or O-glycosylation sites on either the alpha or beta chain. Sequences providing potential glycosylation recognition sites may be either an N-terminal or C-terminal extension on either subunit. Exemplary modified proteins contain an N-terminal extension on a subunit that is selected from the group consisting of ANITV (SEQ ID NO.: 72) and ANITVNITV (SEQ ID NO.: 73).

Increased half-life may also be provided by the use of a peptide extensions such as a carboxyl terminal extension peptide of hCG. See U.S. Ser. No. 09/519,728 which is herein incorporated by reference in its entirety. A subunit of a VEGF analog may be covalently bound by any method known in the art to a CTEP, e.g., by a peptide bond or by a heterobifunctional reagent able to form a covalent bond between the amino terminus and carboxyl terminus of a protein, including but not limited to a peptide linker.

In another embodiment of the invention, the basic amino acid substitutions of the invention are coupled with one or more amino acid substitutions that enhance stability and increase serum half-life by eliminating one or more proteolytic cleavage sites. In one embodiment, the additional amino acid substitutions reduce proteolytic cleavage. In another embodiment, the additional amino acid substitutions prevent proteolytic cleavage. The invention includes VEGF analogs that contain one or more mutations which induce resistance to plasmin and other members of the plasminogen family. In one embodiment of the invention, at least one subunit of a VEGF molecule contains an amino acid substitution corresponding to amino acid positions A111 and/or A148 such as A111P and/or A148P of $VEGF_{165}$ (SEQ ID NO.: 4) or VEGF165b (SEQ ID NO.: 13). For instance, the invention includes $VEGF_{121}$, $VEGF_{145}$, $VEGF_{148}$, $VEGF_{183}$, $VEGF_{189}$ and $VEGF_{206}$ containing an amino acid substitution at position A111. The invention includes one or more mutations in VEGF-B, VEGF-C, VEGF-D and PlGF which inhibit or reduce protease cleavage. For instance, the invention includes amino acid substitutions which prevent the cleavage of VEGF-C and VEGF-D necessary for bioactivity.

In another embodiment, half-life can be increased by linking VEGF monomers and by constructing fusion proteins. Increasing the size of a VEGF analog without interfering with binding sites can increase the half-life of the molecule.

Increased half-life may be provided by crosslinking, including but not limited to pegylation or conjugation of other appropriate chemical groups. Such methods are known in the art, for instance as described in U.S. Pat. No. 5,612,034, U.S. Pat. No. 6,225,449, and U.S. Pat. No. 6,555,660, each of which is incorporated by reference in its entirety. Half-life may also be increased by increasing the number of negatively charged residues within the molecule, for instance, the number of glutamate and/or aspartate residues. Such alteration may be accomplished by site directed mutagenesis or by an insertion of an amino acid sequence containing one or more negatively charged residues into said modified VEGF, including insertions selected from the group consisting of GEFT and GEFTT, among others.

The half-life of a protein is a measurement of protein stability and indicates the time necessary for a one-half reduction in the concentration of the protein. The serum half-life of the modified VEGF molecules described herein may be determined by any method suitable for measuring VEGF levels in samples from a subject over time, for example, but not limited to, immunoassays using anti-VEGF antibodies to measure VEGF levels in serum samples taken over a period of time after administration of the modified VEGF, or by detection of labeled VEGF molecules, i.e., radiolabeled molecules, in samples taken from a subject after administration of the labeled VEGF.

The rate of absorption of a VEGF analog of the present invention may result in increased or decreased duration of action. A VEGF analog with an increased rate of absorption and decreased duration of action may be beneficial for patients receiving a VEGF analog pharmaceutical composition by way of subcutaneous administration or other route of administration generally associated with a slow rate of absorption and/or increased duration of action by counteracting the absorption qualities associated with the route of administration.

Linker

The VEGF analog of the invention can contain two or more monomers separated by a linker peptide. A linker peptide can be used to form a VEGF analog in a single chain conformation. A skilled artisan can appreciate that various types of linkers can be used in the present invention to form a VEGF single chain molecule that is capable of binding a VEGF receptor and which acts as a VEGF receptor antagonist. A linker peptide should not hinder the ability of the single chain molecule to bind a VEGF receptor.

The linker peptide can range from about 2 to about 50 or more amino acids in length. For instance, the linker can consist of about 2 amino acids, about 3 amino acids, about 4 amino acids, about 5 amino acids, about 6 amino acids, about 7 amino acids, about 8 amino acids, about 9 amino acids, about 10 amino acids, about 10-15 amino acids, or about 15-20 amino acids. In one embodiment of the invention, the linker is Gly-Ser or contains Gly-Ser. In another embodiment, the linker is a glycine-rich polypeptide chain.

VEGF molecules containing a linker can be constructed using the methods described herein. A skilled artisan would be able to appreciate that VEGF analog molecules of the invention containing linker peptides can include any of the mutations described herein, in one or more monomers. Further, a VEGF analog containing one or more linker peptides can link more than one type of VEGF protein or isoform. For instance, the present invention includes, but is not limited to, a modified VEGF single chain molecule with a wild-type $VEGF_{165}$ monomer linked to a modified $VEGF_{165}$ monomer containing an I83B substitution; a wild-type $VEGF_{165}$ monomer linked to a modified $VEGF_{165}$b containing an I83B substitution; and a modified $VEGF_{165}$ monomer fused to a modified VEGF-F monomer.

VEGF Fusion Proteins

The present invention also includes fusion proteins, i.e., chimeras, containing one or more modified VEGF proteins or fragments. "Fusion protein" and "chimera" are used interchangeably herein. As used herein, a VEGF moiety is a VEGF protein or protein fragment containing one or more of the basic amino acid substitutions of the invention. A VEGF fusion protein can have one or more VEGF moieties.

Such a fusion protein may be made by ligating the appropriate nucleic acid sequences encoding the desired amino acid sequences to each other by methods known in the art, in the proper coding frame, and expressing the fusion protein by any of the means described herein. Alternatively, such a fusion protein may be made by protein synthesis techniques, for example, using a peptide synthesizer.

The fusion protein of the invention contains at least one VEGF protein or protein fragment containing one or more basic amino acid substitutions described herein. In one embodiment the fusion protein contains a basic amino acid substitution at position I83 of $VEGF_{165}$ (SEQ ID NO. 4), $VEGF_{165}$b (SEQ ID NO. 13), $VEGF_{121}$ (SEQ ID NO.: 6), $VEGF_{145}$ (SEQ ID NO.: 8), $VEGF_{148}$ (SEQ ID NO.: 10), $VEGF_{183}$ (SEQ ID NO.: 15), $VEGF_{189}$ (SEQ ID NO.: 17) or $VEGF_{206}$ (SEQ ID NO.: 19). In another embodiment, the fusion protein contains at least one basic amino acid substitution at a position corresponding to I83K of SEQ ID NO.: 4 in another VEGF protein, for instance, an isoform of VEGF-B, VEGF-C, VEGF-D or PlGF. As can be appreciated by a skilled artisan, human or animal VEGF proteins or fragments thereof may be used for the fusion proteins of the invention.

In one embodiment of the invention, two different VEGF protein subunits or fragments thereof are fused. For instance, the invention includes a VEGF-A subunit or fragment thereof fused to a VEGF-B subunit or fragment thereof, a VEGF-C subunit or fragment thereof, a VEGF-D subunit or fragment thereof, or a PlGF subunit or fragment thereof; a VEGF-B subunit or fragment thereof fused to a VEGF-A subunit or fragment thereof, a VEGF-C subunit or fragment thereof, a VEGF-D subunit or fragment thereof, or a PlGF subunit or fragment thereof; a VEGF-C subunit or fragment thereof fused to a VEGF-A subunit or fragment thereof, a VEGF-B subunit or fragment thereof, a VEGF-D subunit or fragment thereof, or a PlGF subunit or fragment thereof; a VEGF-D subunit or fragment thereof fused to a VEGF-A subunit or fragment thereof, a VEGF-B subunit or fragment thereof, a VEGF-C subunit or fragment thereof, or a PlGF subunit or fragment thereof; and a PlGF subunit or fragment thereof fused to a VEGF-A subunit or fragment thereof, a VEGF-B subunit or fragment thereof, a VEGF-C subunit or fragment thereof, or a VEGF-D subunit or fragment thereof.

The invention includes fusion proteins comprised of two or more different isoforms of the same VEGF protein or fragments thereof. For instance, the invention includes a fusion protein comprised of a $VEGF_{165}$ subunit or fragment thereof fused to a $VEGF_{121}$ subunit or fragment thereof, a $VEGF_{145}$ subunit or fragment thereof, a $VEGF_{148}$ subunit or fragment or subunit thereof, a $VEGF_{165}$b subunit or fragment thereof, a $VEGF_{183}$ subunit or fragment thereof, a $VEGF_{189}$ subunit or fragment thereof, or a $VEGF_{206}$ subunit or fragment thereof. The invention also includes a $VEGF_{165}$b subunit or fragment thereof fused to a $VEGF_{121}$ subunit or fragment thereof, a $VEGF_{145}$ subunit or fragment thereof, a $VEGF_{148}$ subunit or fragment or subunit thereof, a $VEGF_{165}$ subunit or fragment thereof, a $VEGF_{183}$ subunit or fragment thereof, a $VEGF_{189}$ subunit or fragment thereof, or a $VEGF_{206}$ subunit or fragment thereof.

The basic amino acid substitutions of the invention may be present in one or more subunits of the protein. For example, a fusion protein containing a $VEGF_{165}$ subunit and $VEGF_{165}$b subunit may only contain an amino acid substitution in the $VEGF_{165}$ subunit. The invention includes a wild-type $VEGF_{165}$ subunit fused by way of a GS linker to a $VEGF_{165}$ containing an I83K amino acid substitution. As can be appreciated by one of skill in the art, the fusion proteins of the present invention containing one mutated subunit can be created in both orientations, i.e., the subunit containing the mutation can be at either the N- or C-terminus of the fusion protein.

In another embodiment of the invention, a VEGF subunit or fragment thereof is fused to a related protein subunit or fragment thereof. For instance, a VEGF subunit or fragment thereof can be fused to a PDGF subunit or other glycoprotein subunit or fragment thereof.

As can be appreciated by one of ordinary skill in the art, the fusion proteins described herein can be constructed using human or animal VEGF sequences. Further, a fusion protein can be constructed using a human VEGF subunit fused to an animal VEGF subunit.

A VEGF fusion protein should be understood to be a VEGF analog. All modifications disclosed herein, for instance, modifications to further increase receptor binding affinity, modifications to increase half-life and stability, modifications to reduce or inhibit protease cleavage, and modifications to disrupt a co-receptor binding site such as a neuropilin-1 binding site can be incorporated in one or more subunits of the VEGF fusion protein.

The fusion proteins of the invention can also contain a linker separating the two or more VEGF subunits or VEGF-related protein subunits. The linker can be covalently linked to and between the peptides of the fusion protein.

VEGF and Toxin Fusion Proteins

The present invention provides fusion proteins comprising a toxin and one or more modified VEGF subunits, i.e., monomers, containing one or more of the basic amino acid substitutions described herein. For instance, the VEGF monomer, i.e., subunit, of a VEGF-toxin fusion protein can contain a basic amino acid at one or more amino acid positions corresponding to the amino acid positions from the group consisting of 44, 67, 72, 73, 83 and 87 (SEQ ID NO.: 4 or SEQ ID NO.: 13). The VEGF and toxin fusion proteins of the invention may optionally contain a linker sequence separating the toxin and one or more VEGF subunits.

As used herein, the term “toxin” refers to a poisonous substance of biological origin. The toxin of the invention may be a soluble toxin as known in the art. The fusion proteins comprising a soluble toxin may be used to target tumors. Such fusion proteins may also be used for diagnostic purposes.

Examples of toxins include, but are not limited to, *Pseudomonas* exotoxins (PE), *Diphtheria* toxins (DT), ricin toxin, abrin toxin, anthrax toxins, shiga toxin, botulism toxin, tetanus toxin, cholera toxin, maitotoxin, palytoxin, ciguatoxin, textilotoxin, batrachotoxin, alpha conotoxin, taipoxin, tetrodotoxin, alpha tityustoxin, saxitoxin, anatoxin, microcystin, aconitine, exfoliatin toxins A and B, enterotoxins, toxic shock syndrome toxin (TSST-1), *Y. pestis* toxin, gas gangrene toxin, and others.

In one embodiment, the present invention provides a pharmaceutical composition comprising a soluble toxin fused to a modified VEGF and a pharmaceutically acceptable carrier. In another embodiment, the present invention provides the use of a modified VEGF fusion protein comprising a soluble toxin for the manufacture of a medicament for the treatment or prevention of diseases or conditions associated with angiogenesis.

Without wishing to be bound by a theory, it is believed that the VEGF-toxin fusion protein of the invention prevents or reduces angiogenesis, the growth of tumors and/or the spread of cancer by targeting and killing the VEGF receptor and surrounding endothelial and tumor cells.

Expression and/or Synthesis of VEGF Receptor Antagonists

The present invention includes nucleic acids encoding the modified VEGF proteins of the invention, as well as vectors and host cells for expressing the nucleic acids.

As used herein, the terms “nucleic acid” or “polynucleotide” refer to deoxyribonucleotides or ribonucleotides and polymers thereof in either single or double stranded form. The invention includes a nucleic acid molecule which codes for a modified VEGF molecule of the invention. For instance, the invention includes a nucleic acid molecule that codes for a modified $VEGF_{165}$ molecule. The nucleic acid molecule of SEQ ID NO.: 1 which codes for wild-type $VEGF_{165}$ can be mutated by methods known in the art such that the mutated $VEGF_{165}$ nucleic acid molecule codes for the modified protein. Similarly, the nucleic acid molecule of SEQ ID NO.: 11 which codes for wild-type $VEGF_{165}$b can be mutated by methods known in the art such that it codes for a $VEGF_{165}$b molecule of the invention.

Once a nucleic acid encoding a particular modified VEGF of interest, or a region of that nucleic acid encoding a portion of the protein containing a basic amino acid substitution, is constructed, modified, or isolated, that nucleic acid can then be cloned into an appropriate vector, which can direct the in vivo or in vitro synthesis of the modified VEGF protein. Alternatively, the nucleic acid encoding a VEGF analog of the invention may be cloned or modified directly in the expression vector of interest. The vector is contemplated to have the necessary functional elements that direct and regulate transcription of the inserted gene, or hybrid gene. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al., Molecular Cloning: A Laboratory Manual, 2nd ed. (1989)). Appropriate promoters for the expression of nucleic acids in different host cells are well known in the art, and are readily interchanged depending on the vector-host system used for expression. Exemplary vectors and host cells are described in U.S. Pat. No. 6,361,992, which is herein incorporated by reference in its entirety.

There are numerous *E. coli* (*Escherichia coli*) expression vectors known to one of ordinary skill in the art which are useful for the expression of the nucleic acid insert. Other vectors suitable for use include expression vectors from bacilli, such as *Bacillus subtilis*, and other enterobacteriaceae, such as *Salmonella, Serratia*, and various *Pseudomonas* species. These expression vectors will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Additionally, yeast expression systems can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, et al., “varies-Factor-Directed Synthesis and Secretion of Mature Foreign Proteins in *Saccharomyces cerevisiae*.” Proc. Nat. Acad. Sci., 81:4642-4646 (1984)). The leader region of pre-pro-alpha-factor contains a signal peptide and a pro-segment which includes a recognition sequence for a yeast protease encoded by the KEX2 gene. This enzyme cleaves the precursor protein on the carboxyl side of a Lys-Arg dipeptide cleavage signal sequence. The VEGF coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or beta-galactosidase, which may be used to facilitate purification of the fusion protein by affinity chromatography. The insertion of protease cleavage sites to separate the components of the fusion protein is applicable to constructs used for expression in yeast. Efficient post-translational glycosolation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral or other promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Exemplary expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Expression of the gene or hybrid gene can be either in vivo or in vitro. In vivo synthesis comprises transforming prokaryotic or eukaryotic cells that can serve as host cells for the vector. For instance, techniques for transforming fungi are well known in the literature, and have been described, for instance, by Beggs (ibid.), Hinnen et al. (Proc. Natl. Acad. Sci. USA 75: 1929-1933, 1978), Yelton et al., (Proc. Natl. Acad. Sci. USA 81: 1740-1747, 1984), and Russell (Nature 301: 167-169, 1983). Other techniques for introducing cloned DNA sequences into fungal cells, such as electroporation (Becker and Guarente, Methods in Enzymol. 194: 182-187, 1991) may be used. The genotype of the host cell will generally contain a genetic defect that is complemented by the selectable marker present on the expression vector. Choice of a particular host and selectable marker is well within the level of ordinary skill in the art.

Cloned DNA sequences comprising modified VEGF and VEGF fusion proteins of the invention may be introduced into cultured mammalian cells by, for example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973.) Other techniques for introducing cloned DNA sequences into mammalian cells, such as electroporation (Neumann et al., EMBO J. 1: 841-845, 1982), or lipofection may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. A particularly preferred amplifiable marker is the $DHFR^r$ (see U.S. Pat. No. 6,291,212) cDNA (Simonsen and Levinson, Proc. Natl. Acad. Sci. USA 80: 2495-2499, 1983). Selectable markers are reviewed by Thilly (Mammalian Cell Technology, Butterworth Publishers, Stoneham, Mass.) and the choice of selectable markers is well within the level of ordinary skill in the art.

Alternatively, expression of the gene can occur in an in vitro expression system. For example, in vitro transcription systems are commercially available which are routinely used to synthesize relatively large amounts of mRNA. In such in vitro transcription systems, the nucleic acid encoding the modified VEGF would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired VEGF analog (Stratagene Cloning Systems, La Jolla, Calif.).

Another method of producing a VEGF receptor antagonist is to link two peptides or polypeptides together by protein chemistry techniques. Peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to a hybrid VEGF protein can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a hybrid peptide. (Grant, G. A., "Synthetic Peptides: A User Guide," W. H. Freeman and Co., N.Y. (1992) and Bodansky, M. and Trost, B., Ed., "Principles of Peptide Synthesis," Springer-Verlag Inc., N.Y. (1993)). Alternatively, the peptide or polypeptide can by independently synthesized in vivo as described above. Once isolated, these independent peptides or polypeptides may be linked to form a VEGF via similar peptide condensation reactions. For example, enzymatic or chemical ligation of cloned or synthetic peptide segments can allow relatively short peptide fragments to be joined to produce larger peptide fragments, polypeptides or whole protein domains (Abrahmsen, L., et al., Biochemistry, 30:4151 (1991); Dawson, et al., "Synthesis of Proteins by Native Chemical Ligation," Science, 266:776-779 (1994)).

The invention also provides fragments of modified VEGF which have antagonist activity. The polypeptide fragments of the present invention can be recombinant proteins obtained by cloning nucleic acids encoding the peptides in an expression system capable of producing the peptides. For example, amino or carboxy-terminal amino acids can be sequentially removed from either the native or the VEGF protein and the respective activity tested in one of many available assays described above. In another example, the modified proteins of the invention may have a portion of either amino terminal or carboxy terminal amino acids, or even an internal region of the protein, replaced with a polypeptide fragment or other moiety, such as biotin, which can facilitate in the purification of the modified VEGF. For example, a modified VEGF can be fused to a maltose binding protein, through either peptide chemistry of cloning the respective nucleic acids encoding the two polypeptide fragments into an expression vector such that the expression of the coding region results in a hybrid polypeptide. The hybrid polypeptide can be affinity purified by passing it over an amylose affinity column, and the modified VEGF can then be separated from the maltose binding region by cleaving the hybrid polypeptide with the specific protease factor Xa. (See, for example, New England Biolabs Product Catalog, 1996, pg. 164).

The VEGF analog of the invention can be a heterodimer or a homodimer. In one embodiment, the VEGF analog is a fusion protein containing one or more VEGF subunits. The VEGF fusion protein of the invention can be a single chain protein containing two or more VEGF subunits separated by linking peptides. In another embodiment, the VEGF analog of the invention is a fusion protein containing one or more VEGF subunits fused to a toxin. The VEGF analog and VEGF analog fusion protein of the invention can be isolated and purified by means known in the art.

All of the VEGF analogs of the invention contain at least one basic amino acid substitution in at least one VEGF subunit. In one embodiment of the invention, the VEGF analogs of the invention contain at least two basic amino acid substitutions, at least 3 basic amino acid substitutions, at least 4 basic amino acid substitutions or at least 5 basic amino acid substitutions in at least one or at least two VEGF subunits.

The invention includes VEGF analogs containing VEGF active fragments, i.e., peptides that are not full length proteins. Active fragments of the modified VEGF of the invention can also be synthesized directly or obtained by chemical or mechanical disruption of larger modified VEGF protein. An active fragment is defined as an amino acid sequence of at least about 5 consecutive amino acids, at least 10 consecutive amino acids, at least 20 consecutive amino acids, at least 30 consecutive amino acids, at least 40 consecutive amino acids, at least 50 consecutive amino acids, at least 60 consecutive amino acids, at least 70 consecutive amino acids, at least 80 consecutive amino acids, at least 90 consecutive amino acids, at least 100 consecutive amino acids, at least 110 consecutive amino acids, at least 120 consecutive amino acids, at least 130 consecutive amino acids, at least 140 consecutive amino acids, at least 150 consecutive amino acids, or at least 160 consecutive amino acids derived from the natural amino acid sequence, which has the relevant activity, e.g., binding or regulatory activity. The fragments, whether attached to other sequences or not, can also include insertions, deletions, substitutions, or other selected modifications of particular regions or specific amino acids residues, provided the activity of the peptide is not significantly altered or impaired compared to the modified VEGF. These modifications can provide for some additional property, such as to remove/add amino acids capable of disulfide bonding, to increase its biolongevity and/or bioactivity, etcetera. In any case, the peptide must possess a bioactive property, such as binding activity, regulation of binding at the binding domain, etcetera. Functional or active regions of the VEGF may be identified by mutagenesis of a specific region of the hormone, followed by expression and testing of the expressed polypeptide. Such methods are readily apparent to a skilled practitioner in the art and can include site-specific mutagenesis of the nucleic acid encoding the receptor (Zoller, M. J. et al.).

Methods of Use

The invention encompasses methods for reducing VEGF-mediated angiogenesis, comprising contacting a cell expressing kinase domain receptor (KDR) with the VEGF analogs, including VEGF-$A_{165}$ and VEGF-$A_{165}$b analogs, described herein such that VEGF-mediated angiogenesis is reduced. KDR-expressing cells to be targeted by the methods of the invention can include either or both prokaryotic and eukaryotic cells. Such cells may be maintained in vitro, or they may be present in vivo, for instance in a patient or subject diagnosed with cancer or another angiogenesis-related disease.

The present invention includes methods of treating a patient diagnosed with an angiogenesis-related disease or condition with a therapeutically effective amount of any of the VEGF receptor antagonists described herein, comprising administering said VEGF analog or fusion protein to said patient such that said angiogenesis-related disease or condition is reduced or inhibited. In order to measure the reduction of angiogenesis, the patient's results may be compared to that of a patient administered a placebo. Exemplary angiogenesis-related diseases are described throughout this application, and include but are not limited to diseases selected from the group consisting of tumors and neoplasias, hemangiomas, rheumatoid arthritis, osteoarthritis, septic arthritis, asthma, atherosclerosis, idiopathic pulmonary fibrosis, vascular restenosis, arteriovenous malformations, meningioma, neovascular glaucoma, psoriasis, Kaposi's Syndrome, angiofibroma, hemophilic joints, hypertrophic scars, Osler-Weber syndrome, pyogenic granuloma, retrolental fibroplasias, scleroderma, trachoma, von Hippel-Lindau disease, vascular adhesion pathologies, synovitis, dermatitis, endometriosis, pterygium, diabetic retinopathy, neovascularization associated with corneal injury or grafts, wounds, sores, and ulcers (skin, gastric and duodenal).

A patient suffering from a disease caused by or exacerbated by an increase in angiogenesis, a decrease in angiogenesis, or otherwise dysregulated angiogenesis can be treated with a VEGF analog alone or in combination with a known VEGF receptor antagonist, an anti-angiogenesis therapy, an anti-cancer therapy, or other therapy known to treat the disease or condition. As used herein, "therapy" includes but is not limited to a known drug. Known VEGF receptor antagonists or anti-angiogenesis therapies include but are not limited to agents that either interrupt VEGF/KDR interaction and/or block the KDR signal transduction pathway such as peptides that block binding of VEGF to KDR, antibodies to VEGF, antibodies to KDR, soluble receptors, tyrosine kinase inhibitors, anti-VEGF immunotoxins, ribozymes, antisense mediated VEGF suppression, and undersulfated, low molecular weight glycol-split heparin.

If a VEGF analog of the invention is used in combination with another therapy, the coupling of the therapies results in a synergistic effect. In addition, a VEGF analog of the present invention can be combined with a drug associated with an undesirable side effect. By coupling a VEGF analog with such a drug, the effective dosage of the drug with the side effect can be lowered to reduce the probability of the side effect from occurring.

The invention includes methods of treating a patient diagnosed with cancer with a therapeutically effective amount of any of the VEGF receptor antagonists described herein, comprising administering said antagonist to said patient such that the spread of said cancer is reduced or inhibited, i.e., metastasis is reduced or inhibited. The invention includes methods of treating a patient diagnosed with cancer with a therapeutically effective amount of any of the VEGF receptor antagonists described herein, comprising administering said antagonist to said patient such that the growth of a tumor is reduced or inhibited. In one embodiment, the VEGF analog functions by inhibiting angiogenesis by reducing or preventing VEGF-induced angiogenesis. In another embodiment, the VEGF analog is a VEGF-toxin fusion protein that prevents or reduces angiogenesis by targeting or killing tumor cells, vascular cells such as endothelial cells and/or VEGF receptors.

Cancers treatable by the methods of the present invention include all solid tumor and metastatic cancers, including but not limited to those selected from the group consisting of bladder, breast, liver, bone, kidney, colon, ovarian, prostate, pancreatic, lung, brain and skin cancers. The invention includes but is not limited to treatment of cancer with a VEGF analog of the present invention, alone, in combination with chemotherapy, or in combination with radiation therapy by methods known in the art (see U.S. Pat. No. 6,596,712). For instance, a VEGF analog may be used with cesium, iridium, iodine, or cobalt radiation.

The present invention includes methods of treating a patient diagnosed with infertility with a therapeutically effective amount of any of the VEGF receptor antagonists described herein, comprising administering said antagonist to said patient such that infertility is deemed treated by one of skill in the art. Infertility can be measured by quantitative and qualitative parameters known in the art such as quantity of oocytes, fertilization rate, blastocyst formation rate, and embryo formation rate. Such infertility diseases include any disease associated with the expression of VEGF that compromises a patient's fertility including but not limited to unexplained female infertility, endometriosis, and unexplained male infertility. The invention includes but is not limited to treatment of infertility by administration of a VEGF analog alone or in combination with other anti-VEGF treatments, anti-angiogenesis treatments, and/or infertility treatments.

The present invention also includes methods of treating a patient diagnosed with an angiogenesis-associated eye disease with a therapeutically effective amount of any of the VEGF receptor antagonists described herein, comprising administering said antagonist to said patient such that said eye disease is reduced or inhibited. Such eye diseases include any eye disease associated with abnormal intraocular neovascularization, including but not limited to retinopathy of prematurity, diabetic retinopathy, retinal vein occlusion, and age-related macular degeneration. The invention includes but is not limited to treatment of angiogenesis-related eye diseases by administration of a VEGF analog alone or in combination with other anti-VEGF treatments, anti-angiogenesis treatments, and/or other eye disease treatments. For example, a VEGF analog of the present invention could be administered to a patient in conjunction with Pfizer's Macugen (pegaptanib) which is a pegylated anti-VEGF aptamer which acts by binding to and inhibiting the activity of VEGF for the treatment of diabetic macular edema, retinal vein occlusion, and age-related macular degeneration.

The present invention also includes methods of treating a patient diagnosed with an angiogenesis-associated inflammatory condition or autoimmune disease with a therapeutically effective amount of any of the VEGF receptor antagonists described herein, comprising administering said antagonist to said patient such that said inflammatory condition is reduced or inhibited. Such inflammatory conditions or diseases include any inflammatory disorder associated with expression of VEGF and activation of cells by VEGF, including but not limited to all types of arthritis and particularly rheumatoid arthritis and osteoarthritis, asthma, pulmonary fibrosis and dermatitis. The invention includes but is not limited to treatment of angiogenesis-related inflammatory conditions or autoimmune disease by administration of a VEGF analog alone or in combination with other anti-VEGF treatments, anti-angiogenesis treatments, inflammation therapeutics, and/or autoimmune disease therapeutics.

In another embodiment of the present invention, the modified VEGF protein of the invention is used as a diagnostic. The VEGF analogs of the invention or VEGF receptors can displayed on a synthetic surface, such as in a protein or peptide array. Such an array is well known in the art and can be used to screen for VEGF analogs which bind to KDR and other receptors known to be involved in angiogenesis. The VEGF analogs disclosed herein can be used as positive controls to assess the ability of putative VEGF analogs to bind to KDR and other receptors known to be involved in angiogenesis. The invention also includes an array comprising the VEGF analogs of the present invention to screen for putative VEGF receptors which may be involved in angiogenesis.

Assays suitable for characterizing the analogs described herein are described in PCT/US/99/05908, which is herein incorporated by reference in its entirety. For instance, various immunoassays may be used including but not limited to competitive binding assays and non-competitive assay systems using techniques such as radioimmunoassays, ELISA, sandwich immunoassays, immunoradiometric assays, gel diffusion precipitin reactions, immunodiffusion assays, in situ immunoassays, western blots, precipitation reactions, agglutination assays, complement fixation assays, immunofluorescence assays, Protein A assays, and immunoelectrophoresis assays, etcetera.

Pharmaceutical Formulations

The invention provides methods of diagnosis and treatment by administration to a subject of an effective amount of a therapeutic of the invention. The subject may be an animal, including but not limited to animals such as cows, pigs, horses, chickens, cats, dogs, etc., and is preferably a mammal, and most preferably human. In a specific embodiment, a non-human mammal is the subject.

The pharmaceutical compositions of the invention comprise an effective amount of one or more modified VEGF proteins of the present invention in combination with the pharmaceutically acceptable carrier. The compositions may further comprise other known drugs suitable for the treatment of the particular disease being targeted. An effective amount of the VEGF receptor antagonist of the present invention is that amount that blocks, inhibits or reduces VEGF stimulation of endothelial cells compared to that which would occur in the absence of the compound; in other words, an amount that decreases the angiogenic activity of the endothelium, compared to that which would occur in the absence of the compound. The effective amount (and the manner of administration) will be determined on an individual basis and will be based on the specific therapeutic VEGF receptor antagonist being used and a consideration of the subject (size, age, general health), the condition being treated (cancer, arthritis, eye disease, etc.), the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the compounds described herein can be determined using in vitro tests, animal models or other dose-response studies, as are known in the art. The VEGF proteins of the present invention can be used alone or in conjunction with other therapies. The therapeutically effective amount may be reduced when a VEGF analog is used in conjunction with another therapy.

The pharmaceutical compositions of the invention may be prepared, packaged, or sold in formulations suitable for intradermal, intravenous, subcutaneous, oral, rectal, vaginal, parenteral, intraperitoneal, topical, pulmonary, intranasal, buccal, ophthalmic, intrathecal, epidural or another route of administration. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For example, the pharmaceutical compositions of the invention can be administered locally to a tumor via microinfusion. Further, administration may be by a single dose or a series of doses.

For pharmaceutical uses, the VEGF analogs of the present invention may be used in combination with a pharmaceutically acceptable carrier, and can optionally include a pharmaceutically acceptable diluent or excipient. Further, the VEGF analogs of the present invention may be used in combination with other known therapies, including but not limited to anti-VEGF therapies, anti-angiogenesis therapies, anti-cancer therapies, infertility therapies, autoimmune disease therapies, inflammation therapies, ocular disease therapies, and skin disease therapies.

The present invention thus also provides pharmaceutical compositions suitable for administration to a subject. The carrier can be a liquid, so that the composition is adapted for parenteral administration, or can be solid, i.e., a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. Active compounds can alternatively be formulated or encapsulated in liposomes, using known methods. Other contemplated formulations include projected nanoparticles and immunologically based formulations.

Liposomes are completely closed lipid bilayer membranes which contain entrapped aqueous volume. Liposomes are vesicles which may be unilamellar (single membrane) or multilamellar (onion-like structures characterized by multiple membrane bilayers, each separated from the next by an aqueous layer). The bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase.

The liposomes of the present invention may be formed by any of the methods known in the art. Several methods may be used to form the liposomes of the present invention. For example, multilamellar vesicles (MLVs), stable plurilamellar vesicles (SPLVs), small unilamellar vesicles (SUV), or reverse phase evaporation vesicles (REVs) may be used. Preferably, however, MLVs are extruded through filters forming large unilamellar vesicles (LUVs) of sizes dependent upon the filter size utilized. In general, polycarbonate filters of 30, 50, 60, 100, 200 or 800 nm pores may be used. In this method, disclosed in Cullis et al., U.S. Pat. No. 5,008,050, relevant portions of which are incorporated by reference herein, the liposome suspension may be repeatedly passed through the extrusion device resulting in a population of liposomes of homogeneous size distribution.

For example, the filtering may be performed through a straight-through membrane filter (a Nuclepore polycarbonate filter) or a tortuous path filter (e.g. a Nuclepore Membrafil filter (mixed cellulose esters) of 0.1 μm size), or by alternative size reduction techniques such as homogenization. The size of the liposomes may vary from about 0.03 to above about 2 microns in diameter; preferably about 0.05 to 0.3 microns and most preferably about 0.1 to about 0.2 microns. The size range includes liposomes that are MLVs, SPLVs, or LUVs.

Lipids which can be used in the liposome formulations of the present invention include synthetic or natural phospholipids and may include phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM) and cardiolipin, among others, either alone or in combination, and also in combination with cholesterol. The phospholipids useful in the present invention may also include dimyristoylphosphatidylcholine (DMPC) and dimyristoylphosphatidylglycerol (DMPG). In other embodiments, distearoylphosphatidylcholine (DSPC), dipalmitoylphosphatidylcholine (DPPC), or hydrogenated soy phosphatidylcholine (HSPC) may also be used. Dimyristoylphosphatidylcholine (DMPC) and diarachidonoylphosphatidylcholine (DAPC) may similarly be used.

During preparation of the liposomes, organic solvents may also be used to suspend the lipids. Suitable organic solvents for use in the present invention include those with a variety of polarities and dielectric properties, which solubilize the lipids, for example, chloroform, methanol, ethanol, dimethylsulfoxide (DMSO), methylene chloride, and solvent mixtures such as benzene:methanol (70:30), among others. As a result, solutions (mixtures in which the lipids and other components are uniformly distributed throughout) containing the lipids are formed. Solvents are generally chosen on the basis of their biocompatability, low toxicity, and solubilization abilities.

To encapsulate the VEGF receptor antagonist(s) of the inventions into the liposomes, the methods described in U.S. Pat. No. 5,380,531, relevant portions of which are incorporated by reference herein, may be used with the analog(s) of the present invention.

Liposomes containing the VEGF analog(s) of the present invention may be used therapeutically in mammals, especially humans, in the treatment of a number of disease states or pharmacological conditions which require sustained release formulations as well as repeated administration. The mode of administration of the liposomes containing the agents of the present invention may determine the sites and cells in the organism to which the VEGF analog may be delivered.

The liposomes of the present invention may be administered alone but will generally be administered in admixture with a pharmaceutical carrier selected with regard to the intended route of administration and standard pharmaceutical practice. The preparations may be injected parenterally, for example, intravenously. For parenteral administration, they can be used, for example, in the form of a sterile aqueous solution which may contain other solutes, for example, enough salts or glucose to make the solution isotonic, should isotonicity be necessary or desired. The liposomes of the present invention may also be employed subcutaneously or intramuscularly. Other uses, depending upon the particular properties of the preparation, may be envisioned by those skilled in the art.

For the oral mode of administration, the liposomal formulations of the present invention can be used in the form of tablets, capsules, lozenges, troches, powders, syrups, elixirs, aqueous solutions and suspensions, and the like. In the case of tablets, carriers which can be used include lactose, sodium citrate and salts of phosphoric acid. Various disintegrants such as starch, lubricating agents, and talc are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added.

For the topical mode of administration, the pharmaceutical formulations of the present invention may be incorporated into dosage forms such as a solution, suspension, gel, oil, ointment or salve, and the like. Preparation of such topical formulations are described in the art of pharmaceutical formulations as exemplified, for example, by Gennaro et al. (1995) Remington's Pharmaceutical Sciences, Mack Publishing. For topical application, the compositions could also be administered as a powder or spray, particularly in aerosol form. For administration to humans in the treatment of disease states or pharmacological conditions, the prescribing physician will ultimately determine the appropriate dosage of the agent for a given human subject, and this can be expected to vary according to the age, weight and response of the individual as well as the pharmacokinetics of the agent used.

The pharmaceutical compositions of the invention further comprise a depot formulation of biopolymers such as biodegradable microspheres. Biodegradable microspheres are used to control drug release rates and to target drugs to specific sites in the body, thereby optimizing their therapeutic response, decreasing toxic side effects, and eliminating the inconvenience of repeated injections. Biodegradable microspheres have the advantage over large polymer implants in that they do not require surgical procedures for implantation and removal.

The biodegradable microspheres used in the context of the invention are formed with a polymer which delays the release of the proteins and maintains, at the site of action, a therapeutically effective concentration for a prolonged period of time. The polymer can be chosen from ethylcellulose, polystyrene, poly(ϵ-caprolactone), poly(lactic acid) and poly(lactic acid-co-glycolic acid) (PLGA). PLGA copolymer is one of the synthetic biodegradable and biocompatible polymers that has reproducible and slow-release characteristics. An advantage of PLGA copolymers is that their degradation rate ranges from months to years and is a function of the polymer molecular weight and the ratio of polylactic acid to polyglycolic acid residues. Several products using PLGA for parenteral applications are currently on the market, including Lupron Depot and Zoladex in the United States and Enantone Depot, Decapeptil, and Pariodel LA in Europe (see Yonsei, Med J. 2000 December; 41(6):720-34 for review).

The pharmaceutical compositions of the invention may further be prepared, packaged, or sold in a formulation suitable for nasal administration as increased permeability has been shown through the tight junction of the nasal epithelium (Pietro and Woolley, The Science behind Nastech's intranasal drug delivery technology. Manufacturing Chemist, August, 2003). Such formulations may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Pharmaceutical compositions of the invention formulated for nasal delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nose.

Formulations suitable for nasal administration may, for example, comprise from about as little as 0.1% (w/w) and as much as 100% (w/w) of the active ingredient, and may further comprise one or more of the additional ingredients described herein.

In some embodiments, the compositions of the invention may be administered by inhalation. For inhalation therapy, the active ingredients may be in a solution useful for administration by metered dose inhalers or in a form suitable for a dry powder inhaler. In another embodiment, the compositions are suitable for administration by bronchial lavage.

Suitable formulations for oral administration include hard or soft gelatin capsules, pills, tablets, including coated tablets, elixirs, suspensions, syrups or inhalations and controlled release forms thereof.

The VEGF receptor antagonists of the present invention can be administered acutely (i.e., during the onset or shortly after events leading to inflammation), or can be administered during the course of a degenerative disease to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art. A typical daily regime can be from about 0.01 μg/kg body weight per day, from about 1 mg/kg body weight per day, from about 10 mg/kg body weight per day, from about 100 mg/kg body weight per day, and from about 1 g/kg body weight per day.

The VEGF receptor antagonists of the invention may be administered intravenously, orally, intranasally, intraocularly, intramuscularly, intrathecally, or by any suitable route in view of the VEGF protein, the protein formulation and the disease to be treated. Modified VEGF for the treatment of inflammatory arthritis can be injected directly into the synovial fluid. Modified VEGF for the treatment of solid tumors may be injected directly into the tumor. Modified VEGF for the treatment of skin diseases may be applied topically, for instance in the form of a lotion or spray. Intrathecal administration, i.e. for the treatment of brain tumors, can comprise injection directly into the brain. Alternatively, modified VEGF may be coupled or conjugated to a second molecule (a "carrier"), which is a peptide or non-proteinaceous moiety selected for its ability to penetrate the blood-brain barrier and transport the active agent across the blood-brain barrier. Examples of suitable carriers are disclosed in U.S. Pat. Nos. 4,902,505; 5,604,198; and 5,017,566, which are herein incorporated by reference in their entirety.

An alternative method of administering the VEGF receptor antagonists of the present invention is carried out by administering to the subject a vector carrying a nucleic acid sequence encoding the modified VEGF protein, where the vector is capable of directing expression and secretion of the protein. Suitable vectors are typically viral vectors, including DNA viruses, RNA viruses, and retroviruses. Techniques for utilizing vector delivery systems and carrying out gene therapy are known in the art (see Lundstrom, 2003, Trends Biotechnol. 21(3):117-22, for a recent review).

Transgenic Animals

The production of transgenic non-human animals that contain a modified VEGF construct with increased receptor binding affinity and optionally antagonistic properties is contemplated in one embodiment of the present invention.

The successful production of transgenic, non-human animals has been described in a number of patents and publications, such as, for example U.S. Pat. No. 6,291,740 (issued Sep. 18, 2001); U.S. Pat. No. 6,281,408 (issued Aug. 28, 2001); and U.S. Pat. No. 6,271,436 (issued Aug. 7, 2001) the contents of which are hereby incorporated by reference in their entireties.

The ability to alter the genetic make-up of animals, such as domesticated mammals including cows, pigs, goats, horses, cattle, and sheep, allows a number of commercial applications. These applications include the production of animals which express large quantities of exogenous proteins in an easily harvested form (e.g., expression into the milk or blood), the production of animals with increased weight gain, feed efficiency, carcass composition, milk production or content, disease resistance and resistance to infection by specific microorganisms and the production of animals having enhanced growth rates or reproductive performance. Animals which contain exogenous DNA sequences in their genome are referred to as transgenic animals.

The most widely used method for the production of transgenic animals is the microinjection of DNA into the pronuclei of fertilized embryos (Wall et al., J. Cell. Biochem. 49:113 [1992]). Other methods for the production of transgenic animals include the infection of embryos with retroviruses or with retroviral vectors. Infection of both pre- and post-implantation mouse embryos with either wild-type or recombinant retroviruses has been reported (Janenich, Proc. Natl. Acad. Sci. USA 73:1260 [1976]; Janenich et al., Cell 24:519 [1981]; Stuhlmann et al., Proc. Natl. Acad. Sci. USA 81:7151 [1984]; Jahner et al., Proc. Natl. Acad. Sci. USA 82:6927 [1985]; Van der Putten et al., Proc. Natl. Acad. Sci. USA 82:6148-6152 [1985]; Stewart et al., EMBO J. 6:383-388 [1987]).

An alternative means for infecting embryos with retroviruses is the injection of virus or virus-producing cells into the blastocoele of mouse embryos (Jahner, D. et al., Nature 298: 623 [1982]). The introduction of transgenes into the germline of mice has been reported using intrauterine retroviral infection of the midgestation mouse embryo (Jahner et al., supra [1982]). Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Application WO 90/08832 [1990]; and Haskell and Bowen, Mol. Reprod. Dev., 40:386 [1995]. PCT International Application WO 90/08832 describes the injection of wild-type feline leukemia virus B into the perivitelline space of sheep embryos at the 2 to 8 cell stage. Fetuses derived from injected embryos were shown to contain multiple sites of integration.

U.S. Pat. No. 6,291,740 (issued Sep. 18, 2001) describes the production of transgenic animals by the introduction of exogenous DNA into pre-maturation oocytes and mature, unfertilized oocytes (i.e., pre-fertilization oocytes) using retroviral vectors which transduce dividing cells (e.g., vectors derived from murine leukemia virus [MLV]). This patent also describes methods and compositions for cytomegalovirus promoter-driven, as well as mouse mammary tumor LTR expression of various recombinant proteins.

U.S. Pat. No. 6,281,408 (issued Aug. 28, 2001) describes methods for producing transgenic animals using embryonic stem cells. Briefly, the embryonic stem cells are used in a mixed cell co-culture with a morula to generate transgenic animals. Foreign genetic material is introduced into the embryonic stem cells prior to co-culturing by, for example, electroporation, microinjection or retroviral delivery. ES cells transfected in this manner are selected for integrations of the gene via a selection marker such as neomycin.

U.S. Pat. No. 6,271,436 (issued Aug. 7, 2001) describes the production of transgenic animals using methods including isolation of primordial germ cells, culturing these cells to produce primordial germ cell-derived cell lines, transforming both the primordial germ cells and the cultured cell lines, and using these transformed cells and cell lines to generate transgenic animals. The efficiency at which transgenic animals are generated is greatly increased, thereby allowing the use of homologous recombination in producing transgenic non-rodent animal species.

Kits Containing Modified VEGF Proteins

In a further embodiment, the present invention provides kits containing a VEGF analog and/or VEGF analog fusion proteins, which can be used, for instance, for therapeutic or non-therapeutic applications. The kit comprises a container with a label. Suitable containers include, for example, bottles, vials, and test tubes. The containers may be formed from a variety of materials such as glass or plastic. The container holds a composition which includes a VEGF analog or VEGF fusion protein that is effective for therapeutic or non-therapeutic applications, such as described above. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use. The kit of the invention may also include a control consisting of wild-type VEGF such as wild-type $VEGF_{165}$ or $VEGF_{165}$b.

The following examples are provided to describe and illustrate the present invention. As such, they should not be construed to limit the scope of the invention. Those in the art will appreciate that many other embodiments also fall within the scope of the invention, as it is described herein above and in the claims.

EXAMPLES

Example 1

Design of VEGF Receptor Antagonists

VEGF-A antagonists of the present invention were designed to increase receptor binding affinity and decrease bioactivity as compared to wild-type VEGF-A. One method by which this was done was by adding a positive charge to the loops of VEGF-A. This approach to design super-antagonists involves a combination of different methods known in the art including but not limited to homology modeling, sequence comparisons, charge scanning mutagenesis, and linking monomers and introduction of mutations in the context of linked monomers.

Figure 3A:
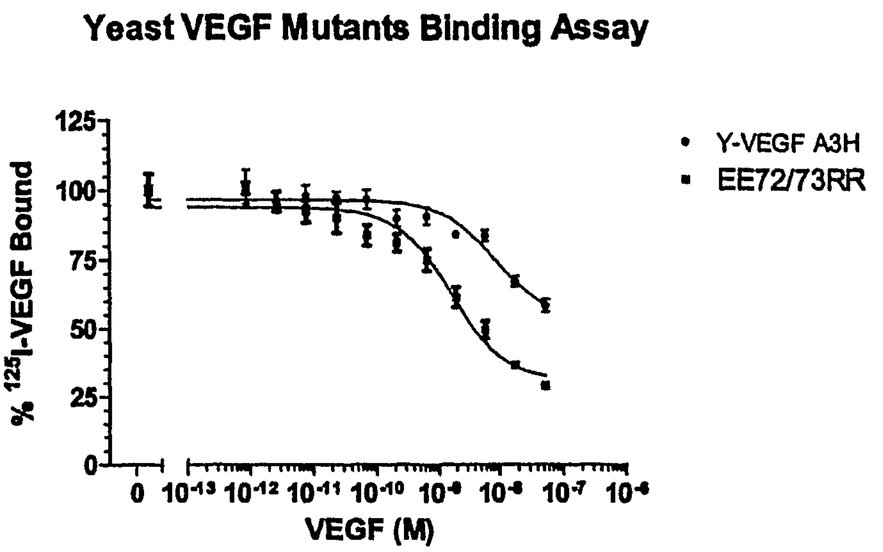
FIG. 3A is a graph comparing binding of the E72R+E73R VEGF mutant and wild-type VEGF-A to KDR.

Vammin, or snake venom VEGF, has been shown to bind to KDR-IgG with high affinity and strongly stimulate proliferation of vascular endothelial cells in vitro (see Yamazaki et al., 2003, J. Biol. Chem. 278, 51985-51988, which is herein incorporated by reference in its entirety). VEGF-A receptor antagonists were designed based on $VEGF_{165}$ homology to vammin. $VEGF_{165}$ has glutamate residues at positions 72 and 73, whereas vammin contains a glycine and lysine residue at these positions, respectively. By modifying VEGF-A to contain two basic amino acid residues at positions 72 and 73, the modified VEGF-A demonstrated a significant increase in receptor binding affinity compared to wild-type VEGF-A (FIG. 3A).

Example 2

Characterization of VEGF Receptor Antagonists

VEGF analogs I83K, E44R, E72RE73R, E67K and Q87K were created and assayed for their ability to bind to KDR and to decrease cell proliferation compared to wild-type VEGF.

Methods

VEGF analogs expressed by yeast cells were incubated with immobilized KDR-Fc and the ability of the analogs to bind to KDR-Fc was assayed. The binding assay was performed as follows:

1. Nunc MaxiSorp™ 96 microwell plates were coated with 150 ng/well KDR-Fc (R & D System, Inc.) and 100 μl 50 mM sodium bicarbonate buffer (15 mM $Na_2CO_3$+35 mM $NaHCO_3$) at pH 9.6. A separate plate was used for each VEGF analog and wild-type VEGF tested.
2. The plates were incubated at 4° C. overnight.
3. The next day, the wells were washed three times in washing buffer (0.05% tween in PBS).
4. The wells were blocked with PBS with 3% BSA, 0.03% tween for 1 hour at room temperature.
5. After blocking, the wells were washed three times in washing buffer (0.05% tween in PBS).
6. VEGF-A (wild-type or mutant) were added at different concentrations to the wells in 50 μl binding buffer (1% BSA and 0.03% tween in PBS).
7. $^{125}$I-labeled VEGF-A (wild-type or mutant) at 70,000 cpm/well (PerkinElmer) was added to each well in 50 μl binding buffer (1% BSA and 0.03% tween in PBS).
8. The contents of the wells were mixed and incubated for 2 hours at room temperature with slow shaking.
9. The wells were washed three times with washing buffer (0.05% tween in PBS).
10. To each well, 120 μl of lysis buffer (0.2 M NaOH+0.5% SDS) was added. Plate was shaken vigorously for 20 minutes at room temperature.
11. The lysis buffer from each well was transferred to an individual tube. The wells were washed with lysis buffer two times additional times and combined with the lysis solution buffer in the corresponding tube.
12. The measure of binding for wild-type VEGF-A and various VEGF-A mutants was determined by counting with a gamma counter.

The ability of HUVEC endothelial cells to proliferate in the presence of the VEGF analogs was assayed as follows:

1. HUVEC endothelial cells (passage 6) were seeded into 96 well plates at 3,000 cells/well using Media-200 with growth factors and incubated overnight.
2. After overnight incubation, the media was removed and Media 199 (Invitrogen) with 2% dialysis FBS (Invitrogen) was added.
3. Cells were incubated for 20 hours.
4. Wild-type VEGF-A and VEGF-A analogs were serial diluted in Media 199 with 2% dialysis FBS in the 96-well plates, starting at 200 ng/well.
5. The media was removed from each well and replaced with 200 μl/well diluted VEGF media.
6. Cells were incubated at 37° C. for 72 hours.

7. Cell proliferation was analyzed using Promega's CellTiter-Glo® Luminescent Cell Viability Assay. Briefly, CellTiter buffer was thawed, transferred into CellTiter-Glo substrate, and mixed well to make substrate mixture. 100 μl growth media was removed from each well into a new 96 well plate and mixed well with 100 μl substrate mixture. The plates were shaken for 2 minutes and incubated at room temperature for an additional ten minutes.

8. Plates were read for luminescent signal using a plate reader with integration time set at 250 mS (Tecan).

Analysis

Figure 1B:
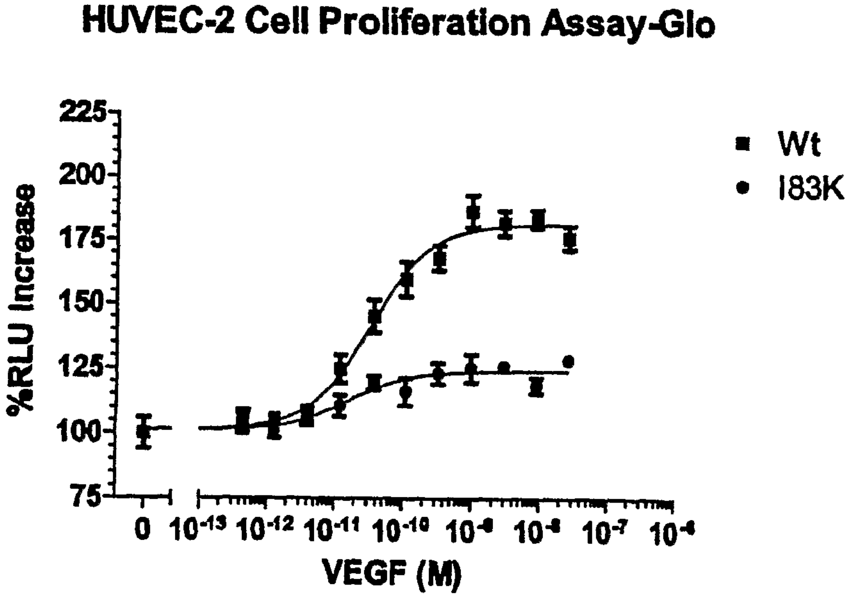
FIG. 1B is a graph showing a decrease in proliferation of HUVEC-2 endothelial cells in the presence of the I83K VEGF-A mutant compared to wild-type VEGF-A.
Figure 2A:
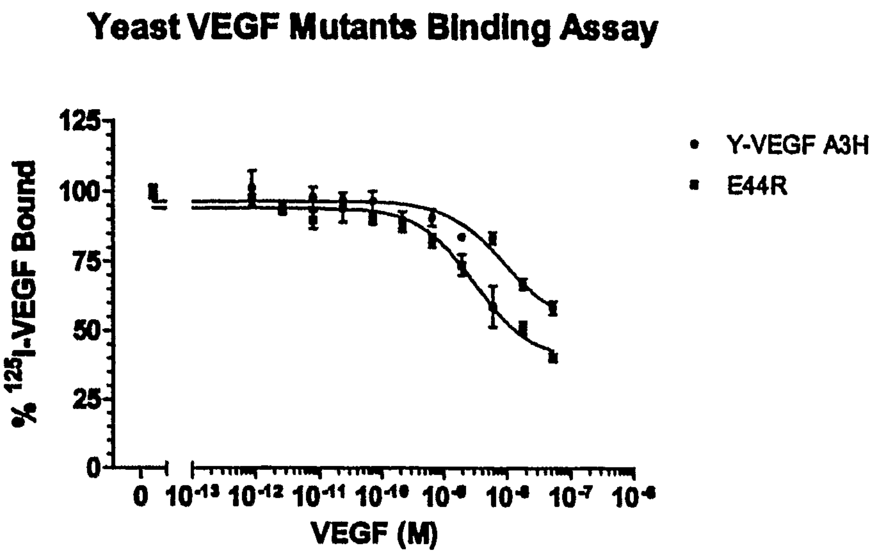
FIG. 2A is a graph comparing binding of the E44R analog and wild-type VEGF-A to KDR.
Figure 2B:
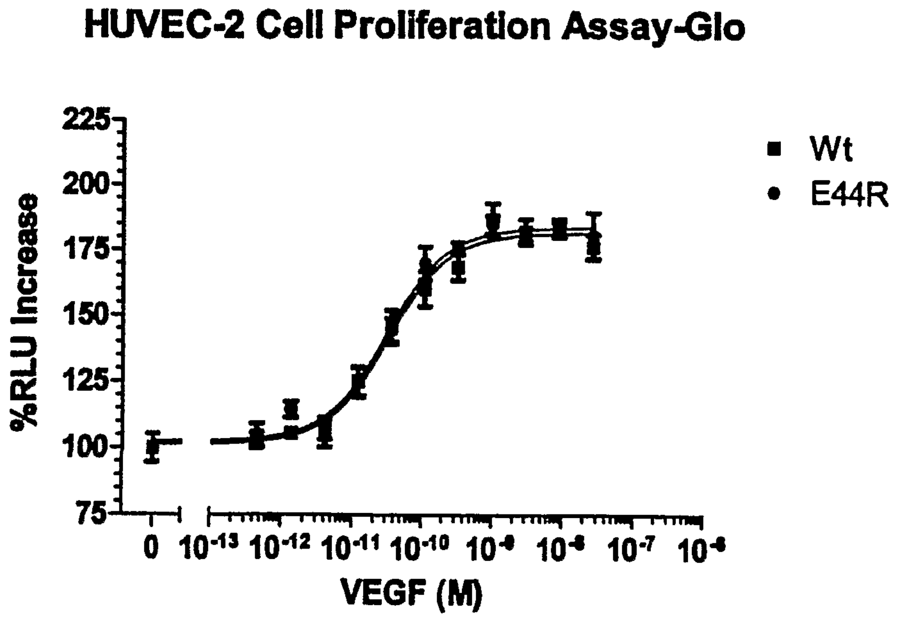
FIG. 2B is a graph comparing HUVEC-2 cell proliferation in the presence of the E44R VEGF-A analog versus wild-type VEGF-A.
Figure 3B:
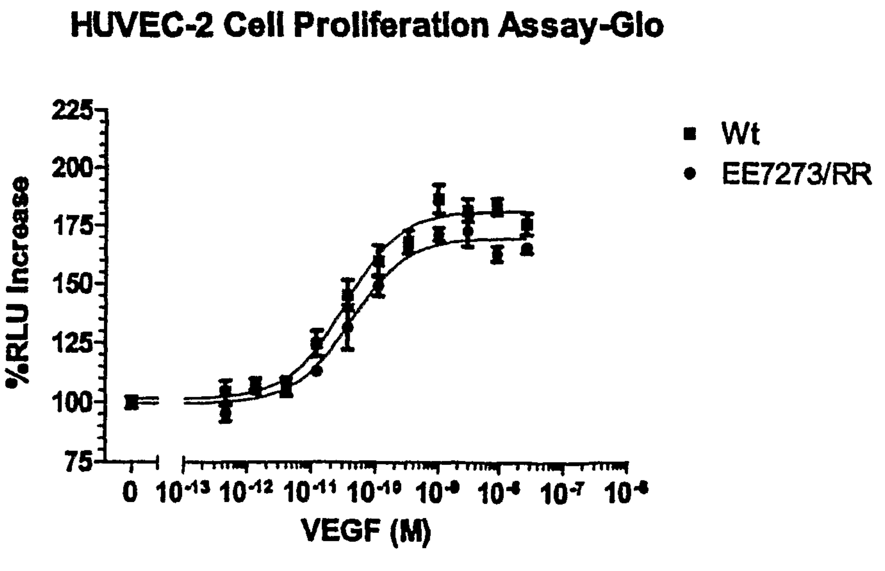
FIG. 3B is a graph comparing HUVEC-2 cell proliferation in the presence of the E72R+E73R VEGF mutant versus wild-type VEGF-A.
Figure 4:
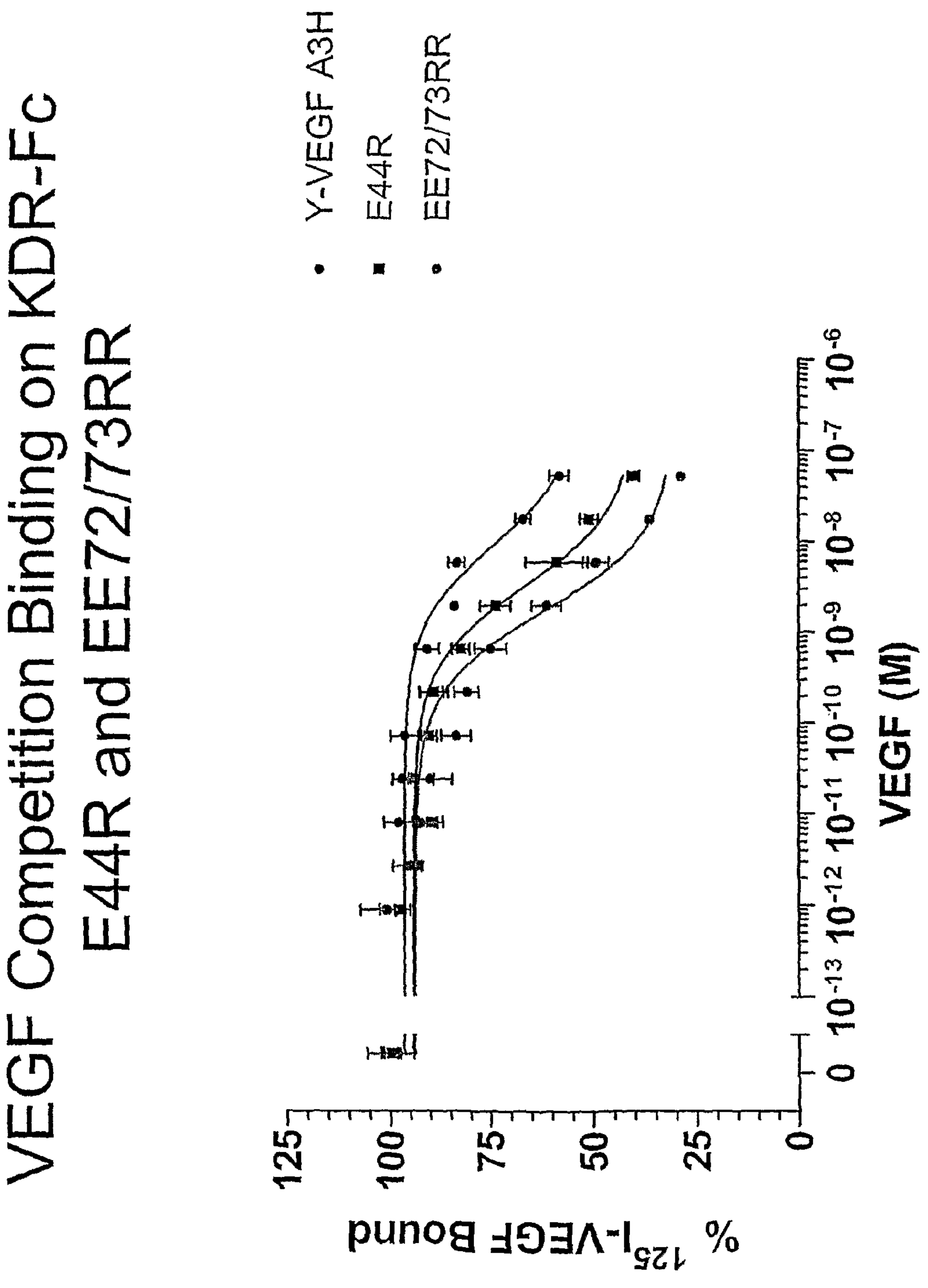
FIG. 4 is a graph comparing binding of E44R and EE72/73RR mutants to wild-type VEGF-A.
Figure 5:
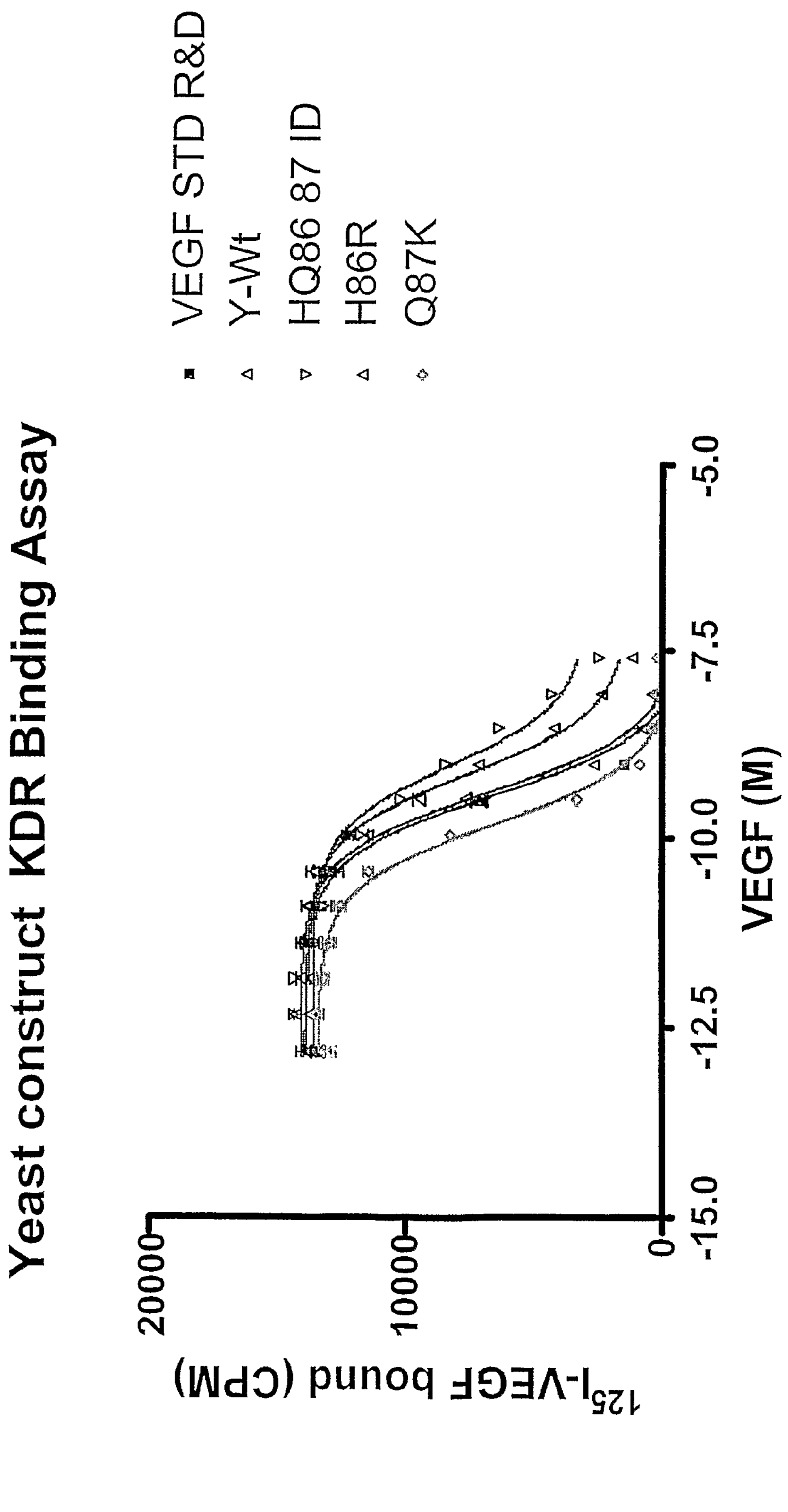
FIG. 5 is a graph comparing binding of Q87K mutant to wild-type VEGF-A.
Figure 6:
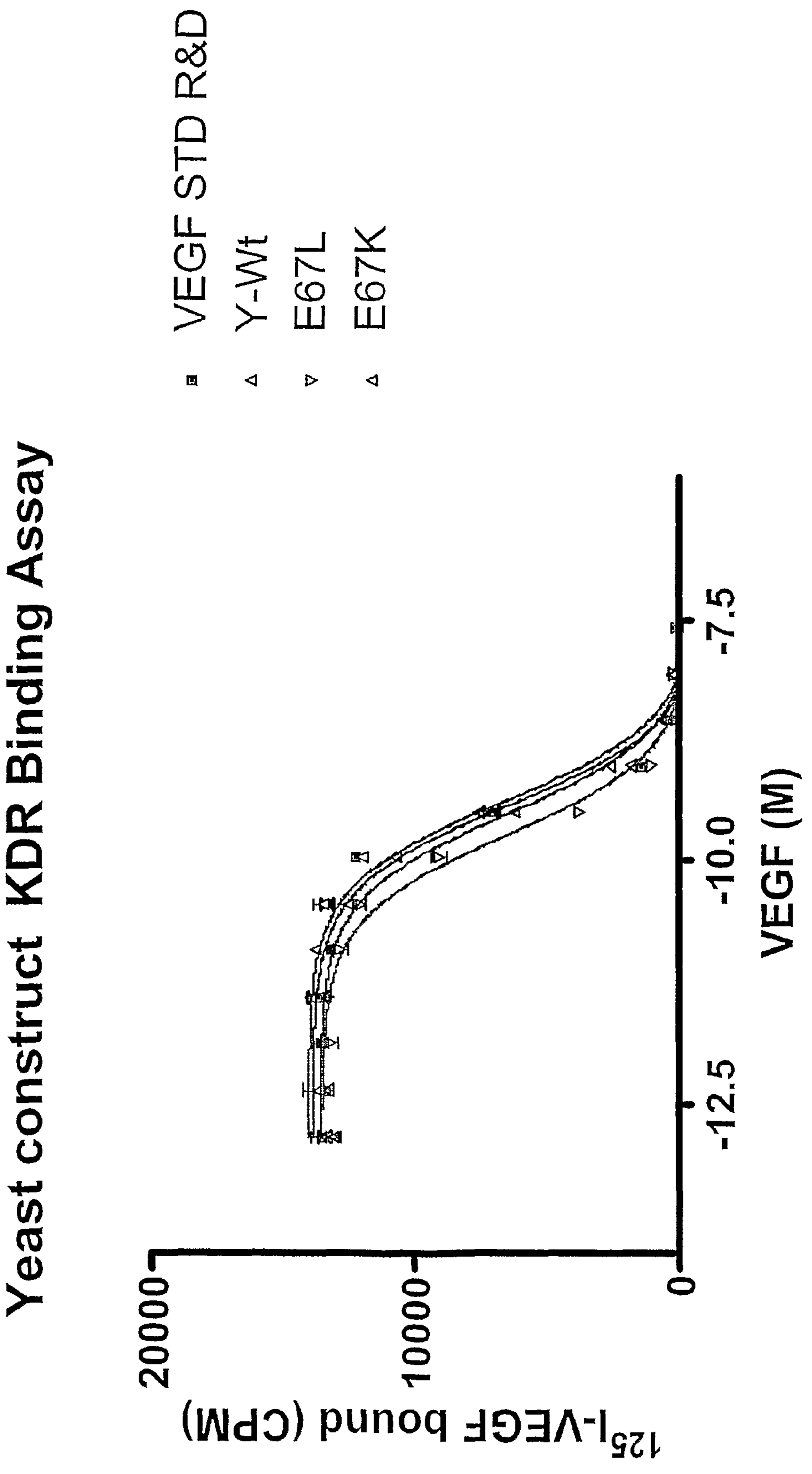
FIG. 6 is a graph comparing binding of E67K mutant to wild-type VEGF-A.

The receptor binding affinity of the I83K analog to KDR-Fc was slightly less than that of wild-type VEGF-A (FIG. 1A). However, the I83K analog demonstrated a significant decrease in endothelial cell proliferation compared to wild-type VEGF-A (FIG. 1B). VEGF-A analogs E44R, EE72/73RR, E67K and Q87K all demonstrated an increase in receptor cell binding affinity compared to wild-type VEGF-A (FIGS. 2A, 3A, 4, 5 and 6). However, analogs E44R and EE72/73RR demonstrated little to no change in endothelial cell proliferation (FIGS. 2B and 3B). These results show that $VEGF_{165}$ analogs comprising I83K can effectively function as a VEGF-A receptor antagonist. Further, although VEGF-A analogs E44R and EE72/73RR were unable to decrease endothelial cell proliferation alone, when added to I83K, these modifications have the potential of further increasing receptor binding affinity.

All publications, patents and patent applications discussed in this application are incorporated herein by reference. While in the foregoing specification this invention has been described in relation to certain preferred embodiments, thereof, and may details have been set forth for purposes of illustration, it will be apparent to those skilled in the art that the invention is susceptible to additional embodiments and that certain of the details described herein may be varied considerably without departing from the basic principles of the invention.

What is claimed:

1. A modified vascular endothelial growth factor (VEGF) protein comprising substitutions at amino acid residues E44, E72, and E73 of SEQ ID NO: 4 or SEQ ID NO: 13 with a positively charged amino acid, wherein the modified VEGF has an increased receptor binding affinity when compared to wild-type VEGF.

2. The modified VEGF-of claim 1, wherein the substitutions are in SEQ ID NO: 4.

3. The modified VEGF of claim 1, wherein the substitutions are in SEQ ID NO: 13.

4. The modified VEGF of claim 1, wherein the positive amino acid is lysine, arginine or histidine.

5. The modified VEGF of claim 1, wherein the modified VEGF is expressed as a homodimer or heterodimer.

6. The modified VEGF of claim 1, further comprising a substitution at C146.

7. The modified VEGF of claim 1, further comprising a substitution at C160.

8. The modified VEGF of claim 1, further comprising substitutions at C146 and C160.

9. The modified VEGF of claim 1, further comprising a substitution at A111.

10. The modified VEGF of claim 1, further comprising a substitution at A148.

11. The modified VEGF of claim 1, further comprising substitutions at A111 and A148.

12. The modified VEGF of claim 1, further comprising a substitution at Q87.

13. The modified VEGF of claim 1, further comprising a substitution at E67.

14. A pharmaceutical composition comprising the modified VEGF of claim 1.

15. The modified VEGF of claim 1, further comprising a N-terminal or C-terminal extension.

16. The modified VEGF of claim 1, wherein at least one of the positive amino acid substitutions at E44, E72 and E73 is arginine.

17. The modified VEGF of claim 1, wherein the amino acid substitutions at E44, E72 and E73 are arginine.

* * * * *

SEQUENCE LISTING

```
<160> NUMBER OF SEQ ID NOS: 73

<210> SEQ ID NO 1
<211> LENGTH: 576
<212> TYPE: DNA
<213> ORGANISM: Homo sapiens

<400> SEQUENCE: 1

atgaactttc tgctgtcttg ggtgcattgg agccttgcct tgctgctcta cctccaccat      60

gccaagtggt cccaggctgc acccatggca gaaggaggag ggcagaatca tcacgaagtg     120

gtgaagttca tggatgtcta tcagcgcagc tactgccatc caatcgagac cctggtggac     180

atcttccagg agtaccctga tgagatcgag tacatcttca agccatcctg tgtgcccctg     240

atgcgatgcg ggggctgctg caatgacgag ggcctggagt gtgtgcccac tgaggagtcc     300

aacatcacca tgcagattat gcggatcaaa cctcaccaag gccagcacat aggagagatg     360

agcttcctac agcacaacaa atgtgaatgc agaccaaaga aagatagagc aagacaagaa     420

aatccctgtg ggccttgctc agagcggaga aagcatttgt ttgtacaaga tccgcagacg     480

tgtaaatgtt cctgcaaaaa cacagactcg cgttgcaagg cgaggcagct tgagttaaac     540

gaacgtactt gcagatgtga caagccgagg cggtga                               576


<210> SEQ ID NO 2
<211> LENGTH: 191
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95
```

```
Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190


<210> SEQ ID NO 3
<211> LENGTH: 26
<212> TYPE: PRT
<213> ORGANISM: Homo sapiens

<400> SEQUENCE: 3

Met Asn Phe Leu Leu Ser Trp Val His Trp Ser Leu Ala Leu Leu Leu
1               5                   10                  15

Tyr Leu His His Ala Lys Trp Ser Gln Ala
            20                  25


<210> SEQ ID NO 4
<211> LENGTH: 165
<212> TYPE: PRT
<213> ORGANISM: Homo sapiens

<400> SEQUENCE: 4

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165


<210> SEQ ID NO 5
<211> LENGTH: 147
<212> TYPE: PRT
<213> ORGANISM: Homo sapiens
```

<400> SEQUENCE: 5

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Cys Asp Lys
    130                 135                 140

Pro Arg Arg
145

<210> SEQ ID NO 6
<211> LENGTH: 121
<212> TYPE: PRT
<213> ORGANISM: Homo sapiens

<400> SEQUENCE: 6

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Cys Asp Lys Pro Arg Arg
        115                 120

<210> SEQ ID NO 7
<211> LENGTH: 171
<212> TYPE: PRT
<213> ORGANISM: Homo sapiens

<400> SEQUENCE: 7

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

-continued

```
Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Cys Asp Lys Pro Arg Arg
                165                 170


<210> SEQ ID NO 8
<211> LENGTH: 145
<212> TYPE: PRT
<213> ORGANISM: Homo sapiens

<400> SEQUENCE: 8

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Cys Asp Lys Pro Arg
    130                 135                 140

Arg
145


<210> SEQ ID NO 9
<211> LENGTH: 174
<212> TYPE: PRT
<213> ORGANISM: Homo sapiens

<400> SEQUENCE: 9

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30
```

-continued

Gly Gly Gln Asn His His Glu Val Val Lys Phe Met Asp Val Tyr Gln
35 40 45

Arg Ser Tyr Cys His Pro Ile Glu Thr Leu Val Asp Ile Phe Gln Glu
50 55 60

Tyr Pro Asp Glu Ile Glu Tyr Ile Phe Lys Pro Ser Cys Val Pro Leu
65 70 75 80

Met Arg Cys Gly Gly Cys Cys Asn Asp Glu Gly Leu Glu Cys Val Pro
85 90 95

Thr Glu Glu Ser Asn Ile Thr Met Gln Ile Met Arg Ile Lys Pro His
100 105 110

Gln Gly Gln His Ile Gly Glu Met Ser Phe Leu Gln His Asn Lys Cys
115 120 125

Glu Cys Arg Pro Lys Lys Asp Arg Ala Arg Gln Glu Asn Pro Cys Gly
130 135 140

Pro Cys Ser Glu Arg Arg Lys His Leu Phe Val Gln Asp Pro Gln Thr
145 150 155 160

Cys Lys Cys Ser Cys Lys Asn Thr Asp Ser Arg Cys Lys Met
165 170

<210> SEQ ID NO 10
<211> LENGTH: 148
<212> TYPE: PRT
<213> ORGANISM: Homo sapiens

<400> SEQUENCE: 10

Ala Pro Met Ala Glu Gly Gly Gly Gln Asn His His Glu Val Val Lys
1 5 10 15

Phe Met Asp Val Tyr Gln Arg Ser Tyr Cys His Pro Ile Glu Thr Leu
20 25 30

Val Asp Ile Phe Gln Glu Tyr Pro Asp Glu Ile Glu Tyr Ile Phe Lys
35 40 45

Pro Ser Cys Val Pro Leu Met Arg Cys Gly Gly Cys Cys Asn Asp Glu
50 55 60

Gly Leu Glu Cys Val Pro Thr Glu Glu Ser Asn Ile Thr Met Gln Ile
65 70 75 80

Met Arg Ile Lys Pro His Gln Gly Gln His Ile Gly Glu Met Ser Phe
85 90 95

Leu Gln His Asn Lys Cys Glu Cys Arg Pro Lys Lys Asp Arg Ala Arg
100 105 110

Gln Glu Asn Pro Cys Gly Pro Cys Ser Glu Arg Arg Lys His Leu Phe
115 120 125

Val Gln Asp Pro Gln Thr Cys Lys Cys Ser Cys Lys Asn Thr Asp Ser
130 135 140

Arg Cys Lys Met
145

<210> SEQ ID NO 11
<211> LENGTH: 606
<212> TYPE: DNA
<213> ORGANISM: Homo sapiens

<400> SEQUENCE: 11
atgaactttc tgctgtcttg ggtgcattgg agccttgcct tgctgctcta cctccaccat 60
gccaagtggt cccaggctgc acccatggca gaaggaggag ggcagaatca tcacgaagtg 120
gtgaagttca tggatgtcta tcagcgcagc tactgccatc caatcgagac cctggtggac 180

-continued

```
atcttccagg agtaccctga tgagatcgag tacatcttca agccatcctg tgtgcccctg    240

atgcgatgcg ggggctgctg caatgacgag ggcctggagt gtgtgcccac tgaggagtcc    300

aacatcacca tgcagattat gcggatcaaa cctcaccaag gccagcacat aggagagatg    360

agcttcctac agcacaacaa atgtgaatgc agaccaaaga aagatagagc aagacaagaa    420

aatccctgtg ggccttgctc agagcggaga aagcatttgt ttgtacaaga tccgcagacg    480

tgtaaatgtt cctgcaaaaa cacagactcg cgttgcaagg cgaggcagct tgagttaaac    540

gaacgtactt gcagatctct caccaggaaa gactgataca gaacgatcga tacagaaacc    600

acgctg                                                               606


<210> SEQ ID NO 12
<211> LENGTH: 191
<212> TYPE: PRT
<213> ORGANISM: Homo sapiens

<400> SEQUENCE: 12

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Ser Leu Thr Arg Lys Asp
            180                 185                 190


<210> SEQ ID NO 13
<211> LENGTH: 165
<212> TYPE: PRT
<213> ORGANISM: Homo sapiens

<400> SEQUENCE: 13

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60
```

```
Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Ser
145                 150                 155                 160

Leu Thr Arg Lys Asp
                165


<210> SEQ ID NO 14
<211> LENGTH: 209
<212> TYPE: PRT
<213> ORGANISM: Homo sapiens

<400> SEQUENCE: 14

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Pro
145                 150                 155                 160

Cys Gly Pro Cys Ser Glu Arg Arg Lys His Leu Phe Val Gln Asp Pro
                165                 170                 175

Gln Thr Cys Lys Cys Ser Cys Lys Asn Thr Asp Ser Arg Cys Lys Ala
            180                 185                 190

Arg Gln Leu Glu Leu Asn Glu Arg Thr Cys Arg Cys Asp Lys Pro Arg
        195                 200                 205

Arg


<210> SEQ ID NO 15
<211> LENGTH: 183
<212> TYPE: PRT
<213> ORGANISM: Homo sapiens

<400> SEQUENCE: 15
```

-continued

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Pro Cys Gly Pro Cys Ser Glu Arg Arg Lys His
    130                 135                 140

Leu Phe Val Gln Asp Pro Gln Thr Cys Lys Cys Ser Cys Lys Asn Thr
145                 150                 155                 160

Asp Ser Arg Cys Lys Ala Arg Gln Leu Glu Leu Asn Glu Arg Thr Cys
                165                 170                 175

Arg Cys Asp Lys Pro Arg Arg
            180


<210> SEQ ID NO 16
<211> LENGTH: 215
<212> TYPE: PRT
<213> ORGANISM: Homo sapiens

<400> SEQUENCE: 16

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190
```

```
Asp Ser Arg Cys Lys Ala Arg Gln Leu Glu Leu Asn Glu Arg Thr Cys
        195                 200                 205

Arg Cys Asp Lys Pro Arg Arg
    210                 215


<210> SEQ ID NO 17
<211> LENGTH: 189
<212> TYPE: PRT
<213> ORGANISM: Homo sapiens

<400> SEQUENCE: 17

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Pro Cys Gly Pro Cys
    130                 135                 140

Ser Glu Arg Arg Lys His Leu Phe Val Gln Asp Pro Gln Thr Cys Lys
145                 150                 155                 160

Cys Ser Cys Lys Asn Thr Asp Ser Arg Cys Lys Ala Arg Gln Leu Glu
                165                 170                 175

Leu Asn Glu Arg Thr Cys Arg Cys Asp Lys Pro Arg Arg
            180                 185


<210> SEQ ID NO 18
<211> LENGTH: 232
<212> TYPE: PRT
<213> ORGANISM: Homo sapiens

<400> SEQUENCE: 18

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110
```

```
Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

<210> SEQ ID NO 19
<211> LENGTH: 206
<212> TYPE: PRT
<213> ORGANISM: Homo sapiens

<400> SEQUENCE: 19

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Tyr Val Gly Ala Arg
    130                 135                 140

Cys Cys Leu Met Pro Trp Ser Leu Pro Gly Pro His Pro Cys Gly Pro
145                 150                 155                 160

Cys Ser Glu Arg Arg Lys His Leu Phe Val Gln Asp Pro Gln Thr Cys
                165                 170                 175

Lys Cys Ser Cys Lys Asn Thr Asp Ser Arg Cys Lys Ala Arg Gln Leu
            180                 185                 190

Glu Leu Asn Glu Arg Thr Cys Arg Cys Asp Lys Pro Arg Arg
        195                 200                 205
```

<210> SEQ ID NO 20
<211> LENGTH: 576
<212> TYPE: DNA
<213> ORGANISM: Macaca fascicularis

<400> SEQUENCE: 20

-continued

```
atgaactttc tgctgtcttg ggtgcattgg agccttgcct tgctgctgta cctccaccat      60

gccaagtggt cccaggctgc acccatggca gaaggaggag ggcagaatca tcacgaagtg     120

gtgaagttca tggatgtcta tcagcgcagc tactgccatc caatcgagac cctggtggac     180

atcttccagg agtaccctga tgagattgag tacatcttca agccatcctg tgtgcccctg     240

atgcgatgtg gggggctgctg caatgacgag ggcctggagt gtgtgcccac tgaggagtcc    300

aacatcacca tgcagattat gcggatcaaa cctcaccaag gccagcacat aggagagatg     360

agcttcctac agcacaacaa atgtgaatgc agaccaaaga aagatagagc aagacaagaa     420

aatccctgtg ggccttgctc agagcggaga aagcatttgt ttgtacaaga tccgcagacg     480

tgtaaatgtt cctgcaaaaa cacagactcg cgttgcaagg cgaggcagct tgagttaaac     540

gaacgtactt gcagatgtga caagccgagg cggtga                               576

<210> SEQ ID NO 21
<211> LENGTH: 191
<212> TYPE: PRT
<213> ORGANISM: Macaca fascicularis

<400> SEQUENCE: 21

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190


<210> SEQ ID NO 22
<211> LENGTH: 165
<212> TYPE: PRT
<213> ORGANISM: Macaca fascicularis

<400> SEQUENCE: 22

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30
```

-continued

```
Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165


<210> SEQ ID NO 23
<211> LENGTH: 573
<212> TYPE: DNA
<213> ORGANISM: Bos taurus

<400> SEQUENCE: 23

atgaactttc tgctctcttg ggtacattgg agccttgcct tgctgctcta ccttcaccat      60

gccaagtggt cccaggctgc acccatggca gaaggagggc agaaacccca cgaagtggtg     120

aagttcatgg atgtctacca gcgcagcttc tgccgtccca tcgagaccct ggtggacatc     180

ttccaggagt acccagatga gattgagttc attttcaagc cgtcctgtgt gcccctgatg     240

cggtgcgggg gctgctgtaa tgacgaaagt ctggagtgtg tgcccactga ggagttcaac     300

atcaccatgc agattatgcg gatcaaacct caccaaagcc agcacatagg agagatgagc     360

ttcctacagc ataacaaatg tgaatgcaga ccaaagaaag ataaagcaag gcaagaaaat     420

ccctgtgggc cttgctcaga gcggagaaag catttgtttg tacaagatcc gcagacgtgt     480

aaatgttcct gcaaaaacac agactcgcgt tgcaaggcga ggcagcttga gttaaacgaa     540

cgtacttgca gatgtgacaa gccgaggcgg tga                                  573


<210> SEQ ID NO 24
<211> LENGTH: 190
<212> TYPE: PRT
<213> ORGANISM: Bos taurus

<400> SEQUENCE: 24

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gln Lys Pro His Glu Val Val Lys Phe Met Asp Val Tyr Gln Arg
        35                  40                  45

Ser Phe Cys Arg Pro Ile Glu Thr Leu Val Asp Ile Phe Gln Glu Tyr
    50                  55                  60

Pro Asp Glu Ile Glu Phe Ile Phe Lys Pro Ser Cys Val Pro Leu Met
65                  70                  75                  80

Arg Cys Gly Gly Cys Cys Asn Asp Glu Ser Leu Glu Cys Val Pro Thr
```

```
                85                  90                  95

Glu Glu Phe Asn Ile Thr Met Gln Ile Met Arg Ile Lys Pro His Gln
            100                 105                 110

Ser Gln His Ile Gly Glu Met Ser Phe Leu Gln His Asn Lys Cys Glu
        115                 120                 125

Cys Arg Pro Lys Lys Asp Lys Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190


<210> SEQ ID NO 25
<211> LENGTH: 164
<212> TYPE: PRT
<213> ORGANISM: Bos taurus

<400> SEQUENCE: 25

Ala Pro Met Ala Glu Gly Gly Gln Lys Pro His Glu Val Val Lys Phe
1               5                   10                  15

Met Asp Val Tyr Gln Arg Ser Phe Cys Arg Pro Ile Glu Thr Leu Val
            20                  25                  30

Asp Ile Phe Gln Glu Tyr Pro Asp Glu Ile Glu Phe Ile Phe Lys Pro
        35                  40                  45

Ser Cys Val Pro Leu Met Arg Cys Gly Gly Cys Cys Asn Asp Glu Ser
    50                  55                  60

Leu Glu Cys Val Pro Thr Glu Glu Phe Asn Ile Thr Met Gln Ile Met
65                  70                  75                  80

Arg Ile Lys Pro His Gln Ser Gln His Ile Gly Glu Met Ser Phe Leu
                85                  90                  95

Gln His Asn Lys Cys Glu Cys Arg Pro Lys Lys Asp Lys Ala Arg Gln
            100                 105                 110

Glu Asn Pro Cys Gly Pro Cys Ser Glu Arg Arg Lys His Leu Phe Val
        115                 120                 125

Gln Asp Pro Gln Thr Cys Lys Cys Ser Cys Lys Asn Thr Asp Ser Arg
    130                 135                 140

Cys Lys Ala Arg Gln Leu Glu Leu Asn Glu Arg Thr Cys Arg Cys Asp
145                 150                 155                 160

Lys Pro Arg Arg


<210> SEQ ID NO 26
<211> LENGTH: 645
<212> TYPE: DNA
<213> ORGANISM: Canis familiaris

<400> SEQUENCE: 26

atgaactttc tgctctcttg ggtgcattgg agccttgcct tgctgctcta cctccaccat      60

gccaagtggt cccaggctgc gcctatggca ggaggagagc acaaacccca cgaagtggtg     120

aagttcatgg acgtctacca gcgcagctac tgccgtccca ttgagaccct ggtggacatc     180

ttccaggagt accctgacga gatcgagtac atcttcaagc catcctgcgt gcccctgatg     240

cggtgtgggg gctgctgtaa tgatgagggc ctagagtgcg tgcccactga ggagttcaac     300

atcaccatgc agattatgcg gatcaaacct catcaaggcc agcacatagg ggagatgagt     360
```

-continued

```
ttcctgcagc atagcaaatg tgaatgcaga ccaaagaaag atagagcaag gcaagaaaaa    420

aaatcaattc gaggaaaggg gaaggggcaa aaaagaaagc gcaagaaatc ccggtataaa    480

ccctggagcg ttccctgtgg gccttgctca gagcggagaa agcatttgtt tgtacaagat    540

ccgcagacgt gtaaatgttc ctgcaaaaac acagactcgc gttgcaaggc gaggcagctt    600

gagttaaacg aacgtacttg cagatgtgac aagccgaggc ggtga                    645


<210> SEQ ID NO 27
<211> LENGTH: 214
<212> TYPE: PRT
<213> ORGANISM: Canis familiaris

<400> SEQUENCE: 27

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Gly Gly
            20                  25                  30

Glu His Lys Pro His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Glu Glu Phe Asn Ile Thr Met Gln Ile Met Arg Ile Lys Pro His Gln
            100                 105                 110

Gly Gln His Ile Gly Glu Met Ser Phe Leu Gln His Ser Lys Cys Glu
        115                 120                 125

Cys Arg Pro Lys Lys Asp Arg Ala Arg Gln Glu Lys Lys Ser Ile Arg
    130                 135                 140

Gly Lys Gly Lys Gly Gln Lys Arg Lys Arg Lys Lys Ser Arg Tyr Lys
145                 150                 155                 160

Pro Trp Ser Val Pro Cys Gly Pro Cys Ser Glu Arg Arg Lys His Leu
                165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
        195                 200                 205

Cys Asp Lys Pro Arg Arg
    210


<210> SEQ ID NO 28
<211> LENGTH: 188
<212> TYPE: PRT
<213> ORGANISM: Canis familiaris

<400> SEQUENCE: 28

Ala Pro Met Ala Gly Gly Glu His Lys Pro His Glu Val Val Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Gly Gly Cys Cys Asn Asp Glu Gly
```

-continued

```
    50                  55                  60

Leu Glu Cys Val Pro Thr Glu Glu Phe Asn Ile Thr Met Gln Ile Met
65                  70                  75                  80

Arg Ile Lys Pro His Gln Gly Gln His Ile Gly Glu Met Ser Phe Leu
                85                  90                  95

Gln His Ser Lys Cys Glu Cys Arg Pro Lys Lys Asp Arg Ala Arg Gln
            100                 105                 110

Glu Lys Lys Ser Ile Arg Gly Lys Gly Lys Gly Gln Lys Arg Lys Arg
        115                 120                 125

Lys Lys Ser Arg Tyr Lys Pro Trp Ser Val Pro Cys Gly Pro Cys Ser
    130                 135                 140

Glu Arg Arg Lys His Leu Phe Val Gln Asp Pro Gln Thr Cys Lys Cys
145                 150                 155                 160

Ser Cys Lys Asn Thr Asp Ser Arg Cys Lys Ala Arg Gln Leu Glu Leu
                165                 170                 175

Asn Glu Arg Thr Cys Arg Cys Asp Lys Pro Arg Arg
            180                 185


<210> SEQ ID NO 29
<211> LENGTH: 651
<212> TYPE: DNA
<213> ORGANISM: Gallus gallus

<400> SEQUENCE: 29

atgaactttc tgctcacttg gatccactgg gggctggcgg cgctgctcta tctgcagagc      60

gcggagttgt cgaaggctgc tccggccctg ggggatgggg agcggaagcc caacgaagtt     120

atcaaattcc tggaagtcta cgaacgcagc ttctgcagga caattgagac cctggtggac     180

attttccagg agtaccctga tgaggtggag tacatattca ggccatcctg tgtgcctctg     240

atgagatgtg cgggttgctg cggcgatgag ggcctagaat gtgtccctgt ggatgtgtac     300

aacgtcacga tggagatcgc aagaattaaa ccccatcaga gtcagcacat agcgcacatg     360

agcttcttac agcacagtaa atgtgactgc agaccaaaga aagatgtcaa aaataaacaa     420

gaaaaaaaat caaagcgagg aaaggggaag ggtcaaaaga gaaagcgcaa gaaaggccgg     480

tacaaaccac ccagctttca ctgtgagcct tgctcagaga ggagaaagca cttgtttgta     540

caagatcccc agacctgtaa atgttcctgc aaattcacag actcacgttg caagtcgagg     600

cagcttgagt taaacgagcg cacttgcaga tgtgaaaaac cgagacggtg a              651


<210> SEQ ID NO 30
<211> LENGTH: 216
<212> TYPE: PRT
<213> ORGANISM: Gallus gallus

<400> SEQUENCE: 30

Met Asn Phe Leu Leu Thr Trp Ile His Trp Gly Leu Ala Ala Leu Leu
1               5                   10                  15

Tyr Leu Gln Ser Ala Glu Leu Ser Lys Ala Ala Pro Ala Leu Gly Asp
            20                  25                  30

Gly Glu Arg Lys Pro Asn Glu Val Ile Lys Phe Leu Glu Val Tyr Glu
        35                  40                  45

Arg Ser Phe Cys Arg Thr Ile Glu Thr Leu Val Asp Ile Phe Gln Glu
    50                  55                  60

Tyr Pro Asp Glu Val Glu Tyr Ile Phe Arg Pro Ser Cys Val Pro Leu
65                  70                  75                  80
```

-continued

```
Met Arg Cys Ala Gly Cys Cys Gly Asp Glu Gly Leu Glu Cys Val Pro
                85                  90                  95

Val Asp Val Tyr Asn Val Thr Met Glu Ile Ala Arg Ile Lys Pro His
            100                 105                 110

Gln Ser Gln His Ile Ala His Met Ser Phe Leu Gln His Ser Lys Cys
        115                 120                 125

Asp Cys Arg Pro Lys Lys Asp Val Lys Asn Lys Gln Glu Lys Lys Ser
    130                 135                 140

Lys Arg Gly Lys Gly Lys Gly Gln Lys Arg Lys Arg Lys Lys Gly Arg
145                 150                 155                 160

Tyr Lys Pro Pro Ser Phe His Cys Glu Pro Cys Ser Glu Arg Arg Lys
                165                 170                 175

His Leu Phe Val Gln Asp Pro Gln Thr Cys Lys Cys Ser Cys Lys Phe
            180                 185                 190

Thr Asp Ser Arg Cys Lys Ser Arg Gln Leu Glu Leu Asn Glu Arg Thr
        195                 200                 205

Cys Arg Cys Glu Lys Pro Arg Arg
    210                 215


<210> SEQ ID NO 31
<211> LENGTH: 190
<212> TYPE: PRT
<213> ORGANISM: Gallus gallus

<400> SEQUENCE: 31

Ala Pro Ala Leu Gly Asp Gly Glu Arg Lys Pro Asn Glu Val Ile Lys
1               5                   10                  15

Phe Leu Glu Val Tyr Glu Arg Ser Phe Cys Arg Thr Ile Glu Thr Leu
            20                  25                  30

Val Asp Ile Phe Gln Glu Tyr Pro Asp Glu Val Glu Tyr Ile Phe Arg
        35                  40                  45

Pro Ser Cys Val Pro Leu Met Arg Cys Ala Gly Cys Cys Gly Asp Glu
    50                  55                  60

Gly Leu Glu Cys Val Pro Val Asp Val Tyr Asn Val Thr Met Glu Ile
65                  70                  75                  80

Ala Arg Ile Lys Pro His Gln Ser Gln His Ile Ala His Met Ser Phe
                85                  90                  95

Leu Gln His Ser Lys Cys Asp Cys Arg Pro Lys Lys Asp Val Lys Asn
            100                 105                 110

Lys Gln Glu Lys Lys Ser Lys Arg Gly Lys Gly Lys Gly Gln Lys Arg
        115                 120                 125

Lys Arg Lys Lys Gly Arg Tyr Lys Pro Pro Ser Phe His Cys Glu Pro
    130                 135                 140

Cys Ser Glu Arg Arg Lys His Leu Phe Val Gln Asp Pro Gln Thr Cys
145                 150                 155                 160

Lys Cys Ser Cys Lys Phe Thr Asp Ser Arg Cys Lys Ser Arg Gln Leu
                165                 170                 175

Glu Leu Asn Glu Arg Thr Cys Arg Cys Glu Lys Pro Arg Arg
            180                 185                 190


<210> SEQ ID NO 32
<211> LENGTH: 573
<212> TYPE: DNA
<213> ORGANISM: Equus caballus

<400> SEQUENCE: 32
```

-continued

```
atgaactttc tgctctcttg ggtgcattgg agccttgcct tgctgctcta cctccaccat      60

gccaagtggt cccaggctgc acccatggca gaaggagagc ataaaaccca tgaagtggtg     120

aagttcatgg acgtctacca gcgcagctac tgccgtccaa tcgagaccct ggtggacatc     180

ttccaggagt accccgatga gatcgagtac atcttcaagc catcctgtgt gcccctgatg     240

cggtgtgggg gctgctgcaa cgacgagggc ctagagtgcg tgcccactgc ggagttcaac     300

atcaccatgc agattatgcg gatcaaacct caccaaagcc aacacatagg agagatgagt     360

ttcctacagc atagcaaatg tgaatgcaga ccaaagaaag ataaagcaag gcaagaaaat     420

ccctgtgggc cttgctcaga gcggagaaag catttgtttg tacaagatcc gcagacgtgt     480

aaatgttcct gcaaaaacac agactcgcgt tgcaaggcga ggcagcttga gttaaacgaa     540

cgtacttgca gatgtgacaa gccgaggcgg tga                                  573
```

```
<210> SEQ ID NO 33
<211> LENGTH: 190
<212> TYPE: PRT
<213> ORGANISM: Equus caballus

<400> SEQUENCE: 33

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Glu His Lys Thr His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Ala Glu Phe Asn Ile Thr Met Gln Ile Met Arg Ile Lys Pro His Gln
            100                 105                 110

Ser Gln His Ile Gly Glu Met Ser Phe Leu Gln His Ser Lys Cys Glu
        115                 120                 125

Cys Arg Pro Lys Lys Asp Lys Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190


<210> SEQ ID NO 34
<211> LENGTH: 164
<212> TYPE: PRT
<213> ORGANISM: Equus caballus

<400> SEQUENCE: 34

Ala Pro Met Ala Glu Gly Glu His Lys Thr His Glu Val Val Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
```

35 40 45

Ser Cys Val Pro Leu Met Arg Cys Gly Gly Cys Cys Asn Asp Glu Gly
50 55 60

Leu Glu Cys Val Pro Thr Ala Glu Phe Asn Ile Thr Met Gln Ile Met
65 70 75 80

Arg Ile Lys Pro His Gln Ser Gln His Ile Gly Glu Met Ser Phe Leu
85 90 95

Gln His Ser Lys Cys Glu Cys Arg Pro Lys Lys Asp Lys Ala Arg Gln
100 105 110

Glu Asn Pro Cys Gly Pro Cys Ser Glu Arg Arg Lys His Leu Phe Val
115 120 125

Gln Asp Pro Gln Thr Cys Lys Cys Ser Cys Lys Asn Thr Asp Ser Arg
130 135 140

Cys Lys Ala Arg Gln Leu Glu Leu Asn Glu Arg Thr Cys Arg Cys Asp
145 150 155 160

Lys Pro Arg Arg

<210> SEQ ID NO 35
<211> LENGTH: 573
<212> TYPE: DNA
<213> ORGANISM: Mus musculus

<400> SEQUENCE: 35
atgaactttc tgctgtcttg ggtgcactgg accctggctt tactgctgta cctccaccat 60
gccaagtggt cccaggctgc acccacgaca gaaggagagc agaagtccca tgaagtgatc 120
aagttcatgg acgtctacca gcgaagctac tgccgtccaa ttgagaccct ggtggacatc 180
ttccaggagt accccgacga gatagagtac atcttcaagc cgtcctgtgt gccgctgatg 240
cgctgtgcag gctgctgtaa cgatgaagcc ctggagtgcg tgcccacgtc agagagcaac 300
atcaccatgc agatcatgcg gatcaaacct caccaaagcc agcacatagg agagatgagc 360
ttcctacagc acagccgatg tgaatgcaga ccaaagaaag acaggacaaa gccagaaaat 420
cactgtgagc cttgttcaga gcggagaaag catttgtttg tccaagatcc gcagacgtgt 480
aaatgttcct gcaaaaacac agactcgcgt tgcaaggcga ggcagcttga gttaaacgaa 540
cgtacttgca gatgtgacaa gccgaggcgg tga 573

<210> SEQ ID NO 36
<211> LENGTH: 214
<212> TYPE: PRT
<213> ORGANISM: Mus musculus

<400> SEQUENCE: 36

Met Asn Phe Leu Leu Ser Trp Val His Trp Thr Leu Ala Leu Leu Leu
1 5 10 15

Tyr Leu His His Ala Lys Trp Ser Gln Ala Ala Pro Thr Thr Glu Gly
20 25 30

Glu Gln Lys Ser His Glu Val Ile Lys Phe Met Asp Val Tyr Gln Arg
35 40 45

Ser Tyr Cys Arg Pro Ile Glu Thr Leu Val Asp Ile Phe Gln Glu Tyr
50 55 60

Pro Asp Glu Ile Glu Tyr Ile Phe Lys Pro Ser Cys Val Pro Leu Met
65 70 75 80

Arg Cys Ala Gly Cys Cys Asn Asp Glu Ala Leu Glu Cys Val Pro Thr
85 90 95

-continued

```
Ser Glu Ser Asn Ile Thr Met Gln Ile Met Arg Ile Lys Pro His Gln
            100                 105                 110

Ser Gln His Ile Gly Glu Met Ser Phe Leu Gln His Ser Arg Cys Glu
        115                 120                 125

Cys Arg Pro Lys Lys Asp Arg Thr Lys Pro Glu Lys Lys Ser Val Arg
    130                 135                 140

Gly Lys Gly Lys Gly Gln Lys Arg Lys Arg Lys Lys Ser Arg Phe Lys
145                 150                 155                 160

Ser Trp Ser Val His Cys Glu Pro Cys Ser Glu Arg Arg Lys His Leu
                165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
        195                 200                 205

Cys Asp Lys Pro Arg Arg
    210


<210> SEQ ID NO 37
<211> LENGTH: 188
<212> TYPE: PRT
<213> ORGANISM: Mus musculus

<400> SEQUENCE: 37

Ala Pro Thr Thr Glu Gly Glu Gln Lys Ser His Glu Val Ile Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Ile Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Lys Lys Ser Val Arg Gly Lys Gly Lys Gly Gln Lys Arg Lys Arg
        115                 120                 125

Lys Lys Ser Arg Phe Lys Ser Trp Ser Val His Cys Glu Pro Cys Ser
    130                 135                 140

Glu Arg Arg Lys His Leu Phe Val Gln Asp Pro Gln Thr Cys Lys Cys
145                 150                 155                 160

Ser Cys Lys Asn Thr Asp Ser Arg Cys Lys Ala Arg Gln Leu Glu Leu
                165                 170                 175

Asn Glu Arg Thr Cys Arg Cys Asp Lys Pro Arg Arg
            180                 185


<210> SEQ ID NO 38
<211> LENGTH: 573
<212> TYPE: DNA
<213> ORGANISM: Sus scrofa

<400> SEQUENCE: 38

atgaactttc tgctgtcttg ggtgcattgg agccttgcct tgctgctcta cctccaccat      60

gccaagtggt cccaggctgc acccatggca gaaggagacc agaaacccca cgaagtggtg     120
```

aagttcatgg acgtctacca gcgcagctac tgccgtccaa tcgagaccct ggtggacatc 180
ttccaggagt accccgatga gatcgagtac atcttcaagc cgtcctgtgt gcccctgatg 240
cggtgcgggg gctgctgcaa cgacgaaggt ctggagtgtg tgcccactga ggagttcaac 300
atcaccatgc agattatgcg gatcaaacct caccaaggcc agcacatagg agagatgagc 360
ttcctacagc acaacaaatg tgaatgcaga ccaaagaaag atagagcgag gcaagaaaat 420
ccctgtgggc cttgctcaga gcggagaaag catttgtttg tacaagatcc gcagacgtgt 480
aaatgttcct gcaaaaacac agactcgcgt tgcaaggcga ggcagcttga gttaaacgaa 540
cgtacttgca gatgtgacaa gccgaggcgg tga 573

<210> SEQ ID NO 39
<211> LENGTH: 190
<212> TYPE: PRT
<213> ORGANISM: Sus scrofa

<400> SEQUENCE: 39

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Asp Gln Lys Pro His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Glu Glu Phe Asn Ile Thr Met Gln Ile Met Arg Ile Lys Pro His Gln
            100                 105                 110

Gly Gln His Ile Gly Glu Met Ser Phe Leu Gln His Asn Lys Cys Glu
        115                 120                 125

Cys Arg Pro Lys Lys Asp Arg Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190
```

<210> SEQ ID NO 40
<211> LENGTH: 164
<212> TYPE: PRT
<213> ORGANISM: Sus scrofa

<400> SEQUENCE: 40

```
Ala Pro Met Ala Glu Gly Asp Gln Lys Pro His Glu Val Val Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Gly Gly Cys Cys Asn Asp Glu Gly
```

```
    50                  55                  60

Leu Glu Cys Val Pro Thr Glu Glu Phe Asn Ile Thr Met Gln Ile Met
65                  70                  75                  80

Arg Ile Lys Pro His Gln Gly Gln His Ile Gly Glu Met Ser Phe Leu
                85                  90                  95

Gln His Asn Lys Cys Glu Cys Arg Pro Lys Lys Asp Arg Ala Arg Gln
            100                 105                 110

Glu Asn Pro Cys Gly Pro Cys Ser Glu Arg Arg Lys His Leu Phe Val
        115                 120                 125

Gln Asp Pro Gln Thr Cys Lys Cys Ser Cys Lys Asn Thr Asp Ser Arg
    130                 135                 140

Cys Lys Ala Arg Gln Leu Glu Leu Asn Glu Arg Thr Cys Arg Cys Asp
145                 150                 155                 160

Lys Pro Arg Arg
```

<210> SEQ ID NO 41
<211> LENGTH: 573
<212> TYPE: DNA
<213> ORGANISM: Rattus norvegicus

<400> SEQUENCE: 41

```
atgaactttc tgctctcttg ggtgcactgg accctggctt tactgctgta cctccaccat      60

gccaagtggt cccaggctgc acccacgaca gaaggggagc agaaagccca tgaagtggtg     120

aagttcatgg acgtctacca gcgcagctat tgccgtccga ttgagaccct ggtggacatc     180

ttccaggagt accccgatga gatagagtat atcttcaagc cgtcctgtgt gcccctaatg     240

cggtgtgcgg gctgctgcaa tgatgaagcc ctggagtgcg tgcccacgtc ggagagcaac     300

gtcactatgc agatcatgcg gatcaaacct caccaaagcc agcacatagg agagatgagc     360

ttcctgcagc atagcagatg tgaatgcaga ccaaagaaag atagaacaaa gccagaaaat     420

cactgtgagc cttgttcaga gcggagaaag catttgtttg tccaagatcc gcagacgtgt     480

aaatgttcct gcaaaaacac agactcgcgt tgcaaggcga ggcagcttga gttaaacgaa     540

cgtacttgca gatgtgacaa gccaaggcgg tga                                  573
```

<210> SEQ ID NO 42
<211> LENGTH: 214
<212> TYPE: PRT
<213> ORGANISM: Rattus norvegicus

<400> SEQUENCE: 42

```
Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
            20                  25                  30

Glu Gln Lys Ala His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Ala Gly Cys Cys Asn Asp Glu Ala Leu Glu Cys Val Pro Thr
                85                  90                  95

Ser Glu Ser Asn Val Thr Met Gln Ile Met Arg Ile Lys Pro His Gln
            100                 105                 110
```

```
Ser Gln His Ile Gly Glu Met Ser Phe Leu Gln His Ser Arg Cys Glu
        115                 120                 125

Cys Arg Pro Lys Lys Asp Arg Thr Lys Pro Glu Lys Lys Ser Val Arg
    130                 135                 140

Gly Lys Gly Lys Gly Gln Lys Arg Lys Arg Lys Lys Ser Arg Phe Lys
145                 150                 155                 160

Ser Trp Ser Val His Cys Glu Pro Cys Ser Glu Arg Arg Lys His Leu
                165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
        195                 200                 205

Cys Asp Lys Pro Arg Arg
    210


<210> SEQ ID NO 43
<211> LENGTH: 188
<212> TYPE: PRT
<213> ORGANISM: Rattus norvegicus

<400> SEQUENCE: 43

Ala Pro Thr Thr Glu Gly Glu Gln Lys Ala His Glu Val Val Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Val Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Lys Lys Ser Val Arg Gly Lys Gly Lys Gly Gln Lys Arg Lys Arg
        115                 120                 125

Lys Lys Ser Arg Phe Lys Ser Trp Ser Val His Cys Glu Pro Cys Ser
    130                 135                 140

Glu Arg Arg Lys His Leu Phe Val Gln Asp Pro Gln Thr Cys Lys Cys
145                 150                 155                 160

Ser Cys Lys Asn Thr Asp Ser Arg Cys Lys Ala Arg Gln Leu Glu Leu
                165                 170                 175

Asn Glu Arg Thr Cys Arg Cys Asp Lys Pro Arg Arg
            180                 185


<210> SEQ ID NO 44
<211> LENGTH: 441
<212> TYPE: DNA
<213> ORGANISM: Ovis aries

<400> SEQUENCE: 44

atgaactttc tgctctcttg ggtgcattgg agccttgcct tgctgctcta ccttcaccat      60

gccaagtggt cccaggctgc acccatggca gaaggagggc agaaacccca tgaagtgatg     120

aagttcatgg atgtctacca gcgcagcttc tgccgtccca ttgagaccct ggtggacatc     180
```

-continued

```
ttccaggagt acccagatga gattgagttc attttcaagc cgtcctgtgt gcccctgatg    240

cggtgcgggg gctgctgtaa tgacgaaagt ctggagtgtg tgcccactga ggagttcaac    300

atcaccatgc agattatgcg gatcaaacct caccaaagcc agcacatagg agagatgagt    360

ttcctacagc ataacaaatg tgaatgcaga ccaaagaaag ataaagcaag gcaagaaaaa    420

tgtgacaagc cgaggcggtg a                                              441


<210> SEQ ID NO 45
<211> LENGTH: 146
<212> TYPE: PRT
<213> ORGANISM: Ovis aries

<400> SEQUENCE: 45

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gln Lys Pro His Glu Val Met Lys Phe Met Asp Val Tyr Gln Arg
        35                  40                  45

Ser Phe Cys Arg Pro Ile Glu Thr Leu Val Asp Ile Phe Gln Glu Tyr
    50                  55                  60

Pro Asp Glu Ile Glu Phe Ile Phe Lys Pro Ser Cys Val Pro Leu Met
65                  70                  75                  80

Arg Cys Gly Gly Cys Cys Asn Asp Glu Ser Leu Glu Cys Val Pro Thr
                85                  90                  95

Glu Glu Phe Asn Ile Thr Met Gln Ile Met Arg Ile Lys Pro His Gln
            100                 105                 110

Ser Gln His Ile Gly Glu Met Ser Phe Leu Gln His Asn Lys Cys Glu
        115                 120                 125

Cys Arg Pro Lys Lys Asp Lys Ala Arg Gln Glu Lys Cys Asp Lys Pro
    130                 135                 140

Arg Arg
145


<210> SEQ ID NO 46
<211> LENGTH: 120
<212> TYPE: PRT
<213> ORGANISM: Ovis aries

<400> SEQUENCE: 46

Ala Pro Met Ala Glu Gly Gly Gln Lys Pro His Glu Val Met Lys Phe
1               5                   10                  15

Met Asp Val Tyr Gln Arg Ser Phe Cys Arg Pro Ile Glu Thr Leu Val
            20                  25                  30

Asp Ile Phe Gln Glu Tyr Pro Asp Glu Ile Glu Phe Ile Phe Lys Pro
        35                  40                  45

Ser Cys Val Pro Leu Met Arg Cys Gly Gly Cys Cys Asn Asp Glu Ser
    50                  55                  60

Leu Glu Cys Val Pro Thr Glu Glu Phe Asn Ile Thr Met Gln Ile Met
65                  70                  75                  80

Arg Ile Lys Pro His Gln Ser Gln His Ile Gly Glu Met Ser Phe Leu
                85                  90                  95

Gln His Asn Lys Cys Glu Cys Arg Pro Lys Lys Asp Lys Ala Arg Gln
            100                 105                 110

Glu Lys Cys Asp Lys Pro Arg Arg
        115                 120
```

<210> SEQ ID NO 47
<211> LENGTH: 188
<212> TYPE: PRT
<213> ORGANISM: Homo sapiens

<400> SEQUENCE: 47

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
    130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185
```

<210> SEQ ID NO 48
<211> LENGTH: 167
<212> TYPE: PRT
<213> ORGANISM: Homo sapiens

<400> SEQUENCE: 48

```
Pro Val Ser Gln Pro Asp Ala Pro Gly His Gln Arg Lys Val Val Ser
1               5                   10                  15

Trp Ile Asp Val Tyr Thr Arg Ala Thr Cys Gln Pro Arg Glu Val Val
            20                  25                  30

Val Pro Leu Thr Val Glu Leu Met Gly Thr Val Ala Lys Gln Leu Val
        35                  40                  45

Pro Ser Cys Val Thr Val Gln Arg Cys Gly Gly Cys Cys Pro Asp Asp
    50                  55                  60

Gly Leu Glu Cys Val Pro Thr Gly Gln His Gln Val Arg Met Gln Ile
65                  70                  75                  80

Leu Met Ile Arg Tyr Pro Ser Ser Gln Leu Gly Glu Met Ser Leu Glu
                85                  90                  95

Glu His Ser Gln Cys Glu Cys Arg Pro Lys Lys Lys Asp Ser Ala Val
            100                 105                 110

Lys Pro Asp Ser Pro Arg Pro Leu Cys Pro Arg Cys Thr Gln His His
        115                 120                 125

Gln Arg Pro Asp Pro Arg Thr Cys Arg Cys Arg Cys Arg Arg Arg Ser
    130                 135                 140
```

```
Phe Leu Arg Cys Gln Gly Arg Gly Leu Glu Leu Asn Pro Asp Thr Cys
145                 150                 155                 160

Arg Cys Arg Lys Leu Arg Arg
                165


<210> SEQ ID NO 49
<211> LENGTH: 207
<212> TYPE: PRT
<213> ORGANISM: Homo sapiens

<400> SEQUENCE: 49

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
    130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205


<210> SEQ ID NO 50
<211> LENGTH: 186
<212> TYPE: PRT
<213> ORGANISM: Homo sapiens

<400> SEQUENCE: 50

Pro Val Ser Gln Pro Asp Ala Pro Gly His Gln Arg Lys Val Val Ser
1               5                   10                  15

Trp Ile Asp Val Tyr Thr Arg Ala Thr Cys Gln Pro Arg Glu Val Val
            20                  25                  30

Val Pro Leu Thr Val Glu Leu Met Gly Thr Val Ala Lys Gln Leu Val
        35                  40                  45

Pro Ser Cys Val Thr Val Gln Arg Cys Gly Gly Cys Cys Pro Asp Asp
    50                  55                  60

Gly Leu Glu Cys Val Pro Thr Gly Gln His Gln Val Arg Met Gln Ile
65                  70                  75                  80

Leu Met Ile Arg Tyr Pro Ser Ser Gln Leu Gly Glu Met Ser Leu Glu
                85                  90                  95
```

```
Glu His Ser Gln Cys Glu Cys Arg Pro Lys Lys Lys Asp Ser Ala Val
            100                 105                 110

Lys Pro Asp Arg Ala Ala Thr Pro His His Arg Pro Gln Pro Arg Ser
        115                 120                 125

Val Pro Gly Trp Asp Ser Ala Pro Gly Ala Pro Ser Pro Ala Asp Ile
    130                 135                 140

Thr His Pro Thr Pro Ala Pro Gly Pro Ser Ala His Ala Ala Pro Ser
145                 150                 155                 160

Thr Thr Ser Ala Leu Thr Pro Gly Pro Ala Ala Ala Ala Ala Asp Ala
                165                 170                 175

Ala Ala Ser Ser Val Ala Lys Gly Gly Ala
            180                 185


<210> SEQ ID NO 51
<211> LENGTH: 419
<212> TYPE: PRT
<213> ORGANISM: Homo sapiens

<400> SEQUENCE: 51

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
```

```
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser


<210> SEQ ID NO 52
<211> LENGTH: 354
<212> TYPE: PRT
<213> ORGANISM: Homo sapiens

<400> SEQUENCE: 52

Met Tyr Arg Glu Trp Val Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
```

-continued

```
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro


<210> SEQ ID NO 53
<211> LENGTH: 149
<212> TYPE: PRT
<213> ORGANISM: Homo sapiens

<400> SEQUENCE: 53

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Cys Gly Asp
    130                 135                 140

Ala Val Pro Arg Arg
145


<210> SEQ ID NO 54
<211> LENGTH: 131
<212> TYPE: PRT
<213> ORGANISM: Homo sapiens

<400> SEQUENCE: 54

Leu Pro Ala Val Pro Pro Gln Gln Trp Ala Leu Ser Ala Gly Asn Gly
1               5                   10                  15

Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45
```

Ser Glu Val Glu His Met Phe Ser Pro Ser Cys Val Ser Leu Leu Arg
50 55 60

Cys Thr Gly Cys Cys Gly Asp Glu Asn Leu His Cys Val Pro Val Glu
65 70 75 80

Thr Ala Asn Val Thr Met Gln Leu Leu Lys Ile Arg Ser Gly Asp Arg
85 90 95

Pro Ser Tyr Val Glu Leu Thr Phe Ser Gln His Val Arg Cys Glu Cys
100 105 110

Arg Pro Leu Arg Glu Lys Met Lys Pro Glu Arg Cys Gly Asp Ala Val
115 120 125

Pro Arg Arg
130

<210> SEQ ID NO 55
<211> LENGTH: 170
<212> TYPE: PRT
<213> ORGANISM: Homo sapiens

<400> SEQUENCE: 55

Met Pro Val Met Arg Leu Phe Pro Cys Phe Leu Gln Leu Leu Ala Gly
1 5 10 15

Leu Ala Leu Pro Ala Val Pro Pro Gln Gln Trp Ala Leu Ser Ala Gly
20 25 30

Asn Gly Ser Ser Glu Val Glu Val Val Pro Phe Gln Glu Val Trp Gly
35 40 45

Arg Ser Tyr Cys Arg Ala Leu Glu Arg Leu Val Asp Val Val Ser Glu
50 55 60

Tyr Pro Ser Glu Val Glu His Met Phe Ser Pro Ser Cys Val Ser Leu
65 70 75 80

Leu Arg Cys Thr Gly Cys Cys Gly Asp Glu Asn Leu His Cys Val Pro
85 90 95

Val Glu Thr Ala Asn Val Thr Met Gln Leu Leu Lys Ile Arg Ser Gly
100 105 110

Asp Arg Pro Ser Tyr Val Glu Leu Thr Phe Ser Gln His Val Arg Cys
115 120 125

Glu Cys Arg Pro Leu Arg Glu Lys Met Lys Pro Glu Arg Arg Arg Pro
130 135 140

Lys Gly Arg Gly Lys Arg Arg Arg Glu Lys Gln Arg Pro Thr Asp Cys
145 150 155 160

His Leu Cys Gly Asp Ala Val Pro Arg Arg
165 170

<210> SEQ ID NO 56
<211> LENGTH: 152
<212> TYPE: PRT
<213> ORGANISM: Homo sapiens

<400> SEQUENCE: 56

Leu Pro Ala Val Pro Pro Gln Gln Trp Ala Leu Ser Ala Gly Asn Gly
1 5 10 15

Ser Ser Glu Val Glu Val Val Pro Phe Gln Glu Val Trp Gly Arg Ser
20 25 30

Tyr Cys Arg Ala Leu Glu Arg Leu Val Asp Val Val Ser Glu Tyr Pro
35 40 45

Ser Glu Val Glu His Met Phe Ser Pro Ser Cys Val Ser Leu Leu Arg
50 55 60

```
Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg Pro Leu Arg Glu Lys Met Lys Pro Glu Arg Arg Arg Pro Lys Gly
        115                 120                 125

Arg Gly Lys Arg Arg Arg Glu Lys Gln Arg Pro Thr Asp Cys His Leu
    130                 135                 140

Cys Gly Asp Ala Val Pro Arg Arg
145                 150


<210> SEQ ID NO 57
<211> LENGTH: 221
<212> TYPE: PRT
<213> ORGANISM: Homo sapiens

<400> SEQUENCE: 57

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg His Ser Pro Gly Arg Gln Ser Pro Asp Met Pro Gly Asp
    130                 135                 140

Phe Arg Ala Asp Ala Pro Ser Phe Leu Pro Pro Arg Arg Ser Leu Pro
145                 150                 155                 160

Met Leu Phe Arg Met Glu Trp Gly Cys Ala Leu Thr Gly Ser Gln Ser
                165                 170                 175

Ala Val Trp Pro Ser Ser Pro Val Pro Glu Glu Ile Pro Arg Met His
            180                 185                 190

Pro Gly Arg Asn Gly Lys Lys Gln Gln Arg Lys Pro Leu Arg Glu Lys
        195                 200                 205

Met Lys Pro Glu Arg Cys Gly Asp Ala Val Pro Arg Arg
    210                 215                 220


<210> SEQ ID NO 58
<211> LENGTH: 203
<212> TYPE: PRT
<213> ORGANISM: Homo sapiens

<400> SEQUENCE: 58

Leu Pro Ala Val Pro Pro Gln Gln Trp Ala Leu Ser Ala Gly Asn Gly
1               5                   10                  15
```

```
Ser Ser Glu Val Glu Val Val Pro Phe Gln Glu Val Trp Gly Arg Ser
            20                  25                  30

Tyr Cys Arg Ala Leu Glu Arg Leu Val Asp Val Val Ser Glu Tyr Pro
        35                  40                  45

Ser Glu Val Glu His Met Phe Ser Pro Ser Cys Val Ser Leu Leu Arg
    50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg His Ser Pro Gly Arg Gln Ser Pro Asp Met Pro Gly Asp Phe Arg
        115                 120                 125

Ala Asp Ala Pro Ser Phe Leu Pro Pro Arg Arg Ser Leu Pro Met Leu
    130                 135                 140

Phe Arg Met Glu Trp Gly Cys Ala Leu Thr Gly Ser Gln Ser Ala Val
145                 150                 155                 160

Trp Pro Ser Ser Pro Val Pro Glu Glu Ile Pro Arg Met His Pro Gly
                165                 170                 175

Arg Asn Gly Lys Lys Gln Gln Arg Lys Pro Leu Arg Glu Lys Met Lys
            180                 185                 190

Pro Glu Arg Cys Gly Asp Ala Val Pro Arg Arg
        195                 200


<210> SEQ ID NO 59
<211> LENGTH: 345
<212> TYPE: PRT
<213> ORGANISM: Homo sapiens

<400> SEQUENCE: 59

Met Ser Leu Phe Gly Leu Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
```

```
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345


<210> SEQ ID NO 60
<211> LENGTH: 326
<212> TYPE: PRT
<213> ORGANISM: Homo sapiens

<400> SEQUENCE: 60

Thr Gln Ala Glu Ser Asn Leu Ser Ser Lys Phe Gln Phe Ser Ser Asn
1               5                   10                  15

Lys Glu Gln Asn Gly Val Gln Asp Pro Gln His Glu Arg Ile Ile Thr
            20                  25                  30

Val Ser Thr Asn Gly Ser Ile His Ser Pro Arg Phe Pro His Thr Tyr
        35                  40                  45

Pro Arg Asn Thr Val Leu Val Trp Arg Leu Val Ala Val Glu Glu Asn
    50                  55                  60

Val Trp Ile Gln Leu Thr Phe Asp Glu Arg Phe Gly Leu Glu Asp Pro
65                  70                  75                  80

Glu Asp Asp Ile Cys Lys Tyr Asp Phe Val Glu Val Glu Glu Pro Ser
                85                  90                  95

Asp Gly Thr Ile Leu Gly Arg Trp Cys Gly Ser Gly Thr Val Pro Gly
            100                 105                 110

Lys Gln Ile Ser Lys Gly Asn Gln Ile Arg Ile Arg Phe Val Ser Asp
        115                 120                 125

Glu Tyr Phe Pro Ser Glu Pro Gly Phe Cys Ile His Tyr Asn Ile Val
    130                 135                 140

Met Pro Gln Phe Thr Glu Ala Val Ser Pro Ser Val Leu Pro Pro Ser
145                 150                 155                 160

Ala Leu Pro Leu Asp Leu Leu Asn Asn Ala Ile Thr Ala Phe Ser Thr
                165                 170                 175

Leu Glu Asp Leu Ile Arg Tyr Leu Glu Pro Glu Arg Trp Gln Leu Asp
            180                 185                 190

Leu Glu Asp Leu Tyr Arg Pro Thr Trp Gln Leu Leu Gly Lys Ala Phe
        195                 200                 205
```

-continued

Val Phe Gly Arg Lys Ser Arg Val Val Asp Leu Asn Leu Leu Thr Glu
    210                 215                 220

Glu Val Arg Leu Tyr Ser Cys Thr Pro Arg Asn Phe Ser Val Ser Ile
225                 230                 235                 240

Arg Glu Glu Leu Lys Arg Thr Asp Thr Ile Phe Trp Pro Gly Cys Leu
                245                 250                 255

Leu Val Lys Arg Cys Gly Gly Asn Cys Ala Cys Cys Leu His Asn Cys
            260                 265                 270

Asn Glu Cys Gln Cys Val Pro Ser Lys Val Thr Lys Lys Tyr His Glu
        275                 280                 285

Val Leu Gln Leu Arg Pro Lys Thr Gly Val Arg Gly Leu His Lys Ser
    290                 295                 300

Leu Thr Asp Val Ala Leu Glu His His Glu Glu Cys Asp Cys Val Cys
305                 310                 315                 320

Arg Gly Ser Thr Gly Gly
                325

<210> SEQ ID NO 61
<211> LENGTH: 147
<212> TYPE: PRT
<213> ORGANISM: Homo sapiens

<400> SEQUENCE: 61

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Cys Asp Lys
    130                 135                 140

Pro Arg Arg
145

<210> SEQ ID NO 62
<211> LENGTH: 121
<212> TYPE: PRT
<213> ORGANISM: Homo sapiens

<400> SEQUENCE: 62

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

```
Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Cys Asp Lys Pro Arg Arg
        115                 120


<210> SEQ ID NO 63
<211> LENGTH: 211
<212> TYPE: PRT
<213> ORGANISM: Homo sapiens

<400> SEQUENCE: 63

Met Arg Thr Leu Ala Cys Leu Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210


<210> SEQ ID NO 64
<211> LENGTH: 196
<212> TYPE: PRT
<213> ORGANISM: Homo sapiens

<400> SEQUENCE: 64

Met Arg Thr Leu Ala Cys Leu Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30
```

```
Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195
```

<210> SEQ ID NO 65
<211> LENGTH: 1338
<212> TYPE: PRT
<213> ORGANISM: Homo sapiens

<400> SEQUENCE: 65

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205
```

```
Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620
```

```
Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Leu Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile  Ser Tyr Ser Phe Gln  Val Ala Arg
        995                  1000                 1005

Gly Met  Glu Phe Leu Ser Ser  Arg Lys Cys Ile His  Arg Asp Leu
    1010                 1015                 1020

Ala Ala  Arg Asn Ile Leu Leu  Ser Glu Asn Asn Val  Val Lys Ile
    1025                 1030                 1035

Cys Asp  Phe Gly Leu Ala Arg  Asp Ile Tyr Lys Asn  Pro Asp Tyr
```

1040 1045 1050

Val Arg Lys Gly Asp Thr Arg Leu Pro Leu Lys Trp Met Ala Pro
1055 1060 1065

Glu Ser Ile Phe Asp Lys Ile Tyr Ser Thr Lys Ser Asp Val Trp
1070 1075 1080

Ser Tyr Gly Val Leu Leu Trp Glu Ile Phe Ser Leu Gly Gly Ser
1085 1090 1095

Pro Tyr Pro Gly Val Gln Met Asp Glu Asp Phe Cys Ser Arg Leu
1100 1105 1110

Arg Glu Gly Met Arg Met Arg Ala Pro Glu Tyr Ser Thr Pro Glu
1115 1120 1125

Ile Tyr Gln Ile Met Leu Asp Cys Trp His Arg Asp Pro Lys Glu
1130 1135 1140

Arg Pro Arg Phe Ala Glu Leu Val Glu Lys Leu Gly Asp Leu Leu
1145 1150 1155

Gln Ala Asn Val Gln Gln Asp Gly Lys Asp Tyr Ile Pro Ile Asn
1160 1165 1170

Ala Ile Leu Thr Gly Asn Ser Gly Phe Thr Tyr Ser Thr Pro Ala
1175 1180 1185

Phe Ser Glu Asp Phe Phe Lys Glu Ser Ile Ser Ala Pro Lys Phe
1190 1195 1200

Asn Ser Gly Ser Ser Asp Asp Val Arg Tyr Val Asn Ala Phe Lys
1205 1210 1215

Phe Met Ser Leu Glu Arg Ile Lys Thr Phe Glu Glu Leu Leu Pro
1220 1225 1230

Asn Ala Thr Ser Met Phe Asp Asp Tyr Gln Gly Asp Ser Ser Thr
1235 1240 1245

Leu Leu Ala Ser Pro Met Leu Lys Arg Phe Thr Trp Thr Asp Ser
1250 1255 1260

Lys Pro Lys Ala Ser Leu Lys Ile Asp Leu Arg Val Thr Ser Lys
1265 1270 1275

Ser Lys Glu Ser Gly Leu Ser Asp Val Ser Arg Pro Ser Phe Cys
1280 1285 1290

His Ser Ser Cys Gly His Val Ser Glu Gly Lys Arg Arg Phe Thr
1295 1300 1305

Tyr Asp His Ala Glu Leu Glu Arg Lys Ile Ala Cys Cys Ser Pro
1310 1315 1320

Pro Pro Asp Tyr Asn Ser Val Val Leu Tyr Ser Thr Pro Pro Ile
1325 1330 1335

<210> SEQ ID NO 66
<211> LENGTH: 1356
<212> TYPE: PRT
<213> ORGANISM: Homo sapiens

<400> SEQUENCE: 66

Met Gln Ser Lys Val Leu Leu Ala Val Ala Leu Trp Leu Cys Val Glu
1 5 10 15

Thr Arg Ala Ala Ser Val Gly Leu Pro Ser Val Ser Leu Asp Leu Pro
20 25 30

Arg Leu Ser Ile Gln Lys Asp Ile Leu Thr Ile Lys Ala Asn Thr Thr
35 40 45

Leu Gln Ile Thr Cys Arg Gly Gln Arg Asp Leu Asp Trp Leu Trp Pro
50 55 60

-continued

```
Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
```

-continued

```
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
    850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910
```

-continued

```
Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
    930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu  Thr Leu Glu His Leu  Ile Cys Tyr
        995                 1000                1005

Ser Phe  Gln Val Ala Lys Gly  Met Glu Phe Leu Ala  Ser Arg Lys
    1010                 1015                1020

Cys Ile  His Arg Asp Leu Ala  Ala Arg Asn Ile Leu  Leu Ser Glu
    1025                 1030                1035

Lys Asn  Val Val Lys Ile Cys  Asp Phe Gly Leu Ala  Arg Asp Ile
    1040                 1045                1050

Tyr Lys  Asp Pro Asp Tyr Val  Arg Lys Gly Asp Ala  Arg Leu Pro
    1055                 1060                1065

Leu Lys  Trp Met Ala Pro Glu  Thr Ile Phe Asp Arg  Val Tyr Thr
    1070                 1075                1080

Ile Gln  Ser Asp Val Trp Ser  Phe Gly Val Leu Leu  Trp Glu Ile
    1085                 1090                1095

Phe Ser  Leu Gly Ala Ser Pro  Tyr Pro Gly Val Lys  Ile Asp Glu
    1100                 1105                1110

Glu Phe  Cys Arg Arg Leu Lys  Glu Gly Thr Arg Met  Arg Ala Pro
    1115                 1120                1125

Asp Tyr  Thr Thr Pro Glu Met  Tyr Gln Thr Met Leu  Asp Cys Trp
    1130                 1135                1140

His Gly  Glu Pro Ser Gln Arg  Pro Thr Phe Ser Glu  Leu Val Glu
    1145                 1150                1155

His Leu  Gly Asn Leu Leu Gln  Ala Asn Ala Gln Gln  Asp Gly Lys
    1160                 1165                1170

Asp Tyr  Ile Val Leu Pro Ile  Ser Glu Thr Leu Ser  Met Glu Glu
    1175                 1180                1185

Asp Ser  Gly Leu Ser Leu Pro  Thr Ser Pro Val Ser  Cys Met Glu
    1190                 1195                1200

Glu Glu  Glu Val Cys Asp Pro  Lys Phe His Tyr Asp  Asn Thr Ala
    1205                 1210                1215

Gly Ile  Ser Gln Tyr Leu Gln  Asn Ser Lys Arg Lys  Ser Arg Pro
    1220                 1225                1230

Val Ser  Val Lys Thr Phe Glu  Asp Ile Pro Leu Glu  Glu Pro Glu
    1235                 1240                1245

Val Lys  Val Ile Pro Asp Asp  Asn Gln Thr Asp Ser  Gly Met Val
    1250                 1255                1260

Leu Ala  Ser Glu Glu Leu Lys  Thr Leu Glu Asp Arg  Thr Lys Leu
    1265                 1270                1275

Ser Pro  Ser Phe Gly Gly Met  Val Pro Ser Lys Ser  Arg Glu Ser
    1280                 1285                1290

Val Ala  Ser Glu Gly Ser Asn  Gln Thr Ser Gly Tyr  Gln Ser Gly
    1295                 1300                1305
```

Tyr His Ser Asp Asp Thr Asp Thr Thr Val Tyr Ser Ser Glu Glu
1310 1315 1320

Ala Glu Leu Leu Lys Leu Ile Glu Ile Gly Val Gln Thr Gly Ser
1325 1330 1335

Thr Ala Gln Ile Leu Gln Pro Asp Ser Gly Thr Thr Leu Ser Ser
1340 1345 1350

Pro Pro Val
1355

<210> SEQ ID NO 67
<211> LENGTH: 1298
<212> TYPE: PRT
<213> ORGANISM: Homo sapiens

<400> SEQUENCE: 67

Met Gln Arg Gly Ala Ala Leu Cys Leu Arg Leu Trp Leu Cys Leu Gly
1 5 10 15

Leu Leu Asp Gly Leu Val Ser Gly Tyr Ser Met Thr Pro Pro Thr Leu
20 25 30

Asn Ile Thr Glu Glu Ser His Val Ile Asp Thr Gly Asp Ser Leu Ser
35 40 45

Ile Ser Cys Arg Gly Gln His Pro Leu Glu Trp Ala Trp Pro Gly Ala
50 55 60

Gln Glu Ala Pro Ala Thr Gly Asp Lys Asp Ser Glu Asp Thr Gly Val
65 70 75 80

Val Arg Asp Cys Glu Gly Thr Asp Ala Arg Pro Tyr Cys Lys Val Leu
85 90 95

Leu Leu His Glu Val His Ala Asn Asp Thr Gly Ser Tyr Val Cys Tyr
100 105 110

Tyr Lys Tyr Ile Lys Ala Arg Ile Glu Gly Thr Thr Ala Ala Ser Ser
115 120 125

Tyr Val Phe Val Arg Asp Phe Glu Gln Pro Phe Ile Asn Lys Pro Asp
130 135 140

Thr Leu Leu Val Asn Arg Lys Asp Ala Met Trp Val Pro Cys Leu Val
145 150 155 160

Ser Ile Pro Gly Leu Asn Val Thr Leu Arg Ser Gln Ser Ser Val Leu
165 170 175

Trp Pro Asp Gly Gln Glu Val Val Trp Asp Asp Arg Arg Gly Met Leu
180 185 190

Val Ser Thr Pro Leu Leu His Asp Ala Leu Tyr Leu Gln Cys Glu Thr
195 200 205

Thr Trp Gly Asp Gln Asp Phe Leu Ser Asn Pro Phe Leu Val His Ile
210 215 220

Thr Gly Asn Glu Leu Tyr Asp Ile Gln Leu Leu Pro Arg Lys Ser Leu
225 230 235 240

Glu Leu Leu Val Gly Glu Lys Leu Val Leu Asn Cys Thr Val Trp Ala
245 250 255

Glu Phe Asn Ser Gly Val Thr Phe Asp Trp Asp Tyr Pro Gly Lys Gln
260 265 270

Ala Glu Arg Gly Lys Trp Val Pro Glu Arg Arg Ser Gln Gln Thr His
275 280 285

Thr Glu Leu Ser Ser Ile Leu Thr Ile His Asn Val Ser Gln His Asp
290 295 300

Leu Gly Ser Tyr Val Cys Lys Ala Asn Asn Gly Ile Gln Arg Phe Arg
305 310 315 320

-continued

```
Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
        355                 360                 365

Tyr Lys Asp Gly Lys Ala Leu Ser Gly Arg His Ser Pro His Ala Leu
    370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
    610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735
```

-continued

```
Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
    770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
    850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
        915                 920                 925

Phe Cys Lys Tyr Gly Asn Leu Ser Asn Phe Leu Arg Ala Lys Arg Asp
    930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
                965                 970                 975

Ser Asp Arg Val Leu Phe Ala Arg Phe Ser Lys Thr Glu Gly Gly Ala
            980                 985                 990

Arg Arg Ala Ser Pro Asp Gln Glu  Ala Glu Asp Leu Trp  Leu Ser Pro
        995                 1000                 1005

Leu Thr  Met Glu Asp Leu Val  Cys Tyr Ser Phe Gln  Val Ala Arg
    1010                 1015                 1020

Gly Met  Glu Phe Leu Ala Ser  Arg Lys Cys Ile His  Arg Asp Leu
    1025                 1030                 1035

Ala Ala  Arg Asn Ile Leu Leu  Ser Glu Ser Asp Val  Val Lys Ile
    1040                 1045                 1050

Cys Asp  Phe Gly Leu Ala Arg  Asp Ile Tyr Lys Asp  Pro Asp Tyr
    1055                 1060                 1065

Val Arg  Lys Gly Ser Ala Arg  Leu Pro Leu Lys Trp  Met Ala Pro
    1070                 1075                 1080

Glu Ser  Ile Phe Asp Lys Val  Tyr Thr Thr Gln Ser  Asp Val Trp
    1085                 1090                 1095

Ser Phe  Gly Val Leu Leu Trp  Glu Ile Phe Ser Leu  Gly Ala Ser
    1100                 1105                 1110

Pro Tyr  Pro Gly Val Gln Ile  Asn Glu Glu Phe Cys  Gln Arg Leu
    1115                 1120                 1125

Arg Asp  Gly Thr Arg Met Arg  Ala Pro Glu Leu Ala  Thr Pro Ala
    1130                 1135                 1140

Ile Arg  Arg Ile Met Leu Asn  Cys Trp Ser Gly Asp  Pro Lys Ala
```

1145 1150 1155

Arg Pro Ala Phe Ser Glu Leu Val Glu Ile Leu Gly Asp Leu Leu
1160 1165 1170

Gln Gly Arg Gly Leu Gln Glu Glu Glu Glu Val Cys Met Ala Pro
1175 1180 1185

Arg Ser Ser Gln Ser Ser Glu Glu Gly Ser Phe Ser Gln Val Ser
1190 1195 1200

Thr Met Ala Leu His Ile Ala Gln Ala Asp Ala Glu Asp Ser Pro
1205 1210 1215

Pro Ser Leu Gln Arg His Ser Leu Ala Ala Arg Tyr Tyr Asn Trp
1220 1225 1230

Val Ser Phe Pro Gly Cys Leu Ala Arg Gly Ala Glu Thr Arg Gly
1235 1240 1245

Ser Ser Arg Met Lys Thr Phe Glu Glu Phe Pro Met Thr Pro Thr
1250 1255 1260

Thr Tyr Lys Gly Ser Val Asp Asn Gln Thr Asp Ser Gly Met Val
1265 1270 1275

Leu Ala Ser Glu Glu Phe Glu Gln Ile Glu Ser Arg His Arg Gln
1280 1285 1290

Glu Ser Gly Phe Arg
1295

<210> SEQ ID NO 68
<211> LENGTH: 923
<212> TYPE: PRT
<213> ORGANISM: Homo sapiens

<400> SEQUENCE: 68

Met Glu Arg Gly Leu Pro Leu Leu Cys Ala Val Leu Ala Leu Val Leu
1 5 10 15

Ala Pro Ala Gly Ala Phe Arg Asn Asp Lys Cys Gly Asp Thr Ile Lys
20 25 30

Ile Glu Ser Pro Gly Tyr Leu Thr Ser Pro Gly Tyr Pro His Ser Tyr
35 40 45

His Pro Ser Glu Lys Cys Glu Trp Leu Ile Gln Ala Pro Asp Pro Tyr
50 55 60

Gln Arg Ile Met Ile Asn Phe Asn Pro His Phe Asp Leu Glu Asp Arg
65 70 75 80

Asp Cys Lys Tyr Asp Tyr Val Glu Val Phe Asp Gly Glu Asn Glu Asn
85 90 95

Gly His Phe Arg Gly Lys Phe Cys Gly Lys Ile Ala Pro Pro Pro Val
100 105 110

Val Ser Ser Gly Pro Phe Leu Phe Ile Lys Phe Val Ser Asp Tyr Glu
115 120 125

Thr His Gly Ala Gly Phe Ser Ile Arg Tyr Glu Ile Phe Lys Arg Gly
130 135 140

Pro Glu Cys Ser Gln Asn Tyr Thr Thr Pro Ser Gly Val Ile Lys Ser
145 150 155 160

Pro Gly Phe Pro Glu Lys Tyr Pro Asn Ser Leu Glu Cys Thr Tyr Ile
165 170 175

Val Phe Ala Pro Lys Met Ser Glu Ile Ile Leu Glu Phe Glu Ser Phe
180 185 190

Asp Leu Glu Pro Asp Ser Asn Pro Pro Gly Gly Met Phe Cys Arg Tyr
195 200 205

-continued

```
Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
    450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Asp Gln Ala
        595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Val Ile Asp Ser Thr Ile Gln
```

625 630 635 640

Ser Glu Phe Pro Thr Tyr Gly Phe Asn Cys Glu Phe Gly Trp Gly Ser
645 650 655

His Lys Thr Phe Cys His Trp Glu His Asp Asn His Val Gln Leu Lys
660 665 670

Trp Ser Val Leu Thr Ser Lys Thr Gly Pro Ile Gln Asp His Thr Gly
675 680 685

Asp Gly Asn Phe Ile Tyr Ser Gln Ala Asp Glu Asn Gln Lys Gly Lys
690 695 700

Val Ala Arg Leu Val Ser Pro Val Val Tyr Ser Gln Asn Ser Ala His
705 710 715 720

Cys Met Thr Phe Trp Tyr His Met Ser Gly Ser His Val Gly Thr Leu
725 730 735

Arg Val Lys Leu Arg Tyr Gln Lys Pro Glu Glu Tyr Asp Gln Leu Val
740 745 750

Trp Met Ala Ile Gly His Gln Gly Asp His Trp Lys Glu Gly Arg Val
755 760 765

Leu Leu His Lys Ser Leu Lys Leu Tyr Gln Val Ile Phe Glu Gly Glu
770 775 780

Ile Gly Lys Gly Asn Leu Gly Gly Ile Ala Val Asp Asp Ile Ser Ile
785 790 795 800

Asn Asn His Ile Ser Gln Glu Asp Cys Ala Lys Pro Ala Asp Leu Asp
805 810 815

Lys Lys Asn Pro Glu Ile Lys Ile Asp Glu Thr Gly Ser Thr Pro Gly
820 825 830

Tyr Glu Gly Glu Gly Glu Gly Asp Lys Asn Ile Ser Arg Lys Pro Gly
835 840 845

Asn Val Leu Lys Thr Leu Glu Pro Ile Leu Ile Thr Ile Ile Ala Met
850 855 860

Ser Ala Leu Gly Val Leu Leu Gly Ala Val Cys Gly Val Val Leu Tyr
865 870 875 880

Cys Ala Cys Trp His Asn Gly Met Ser Glu Arg Asn Leu Ser Ala Leu
885 890 895

Glu Asn Tyr Asn Phe Glu Leu Val Asp Gly Val Lys Leu Lys Lys Asp
900 905 910

Lys Leu Asn Thr Gln Ser Thr Tyr Ser Glu Ala
915 920

<210> SEQ ID NO 69
<211> LENGTH: 931
<212> TYPE: PRT
<213> ORGANISM: Homo sapiens

<400> SEQUENCE: 69

Met Asp Met Phe Pro Leu Thr Trp Val Phe Leu Ala Leu Tyr Phe Ser
1 5 10 15

Arg His Gln Val Arg Gly Gln Pro Asp Pro Pro Cys Gly Gly Arg Leu
20 25 30

Asn Ser Lys Asp Ala Gly Tyr Ile Thr Ser Pro Gly Tyr Pro Gln Asp
35 40 45

Tyr Pro Ser His Gln Asn Cys Glu Trp Ile Val Tyr Ala Pro Glu Pro
50 55 60

Asn Gln Lys Ile Val Leu Asn Phe Asn Pro His Phe Glu Ile Glu Lys
65 70 75 80

-continued

```
His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
```

-continued

```
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
    530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
        595                 600                 605

Lys Ser Glu Glu Thr Thr Thr Pro Tyr Pro Thr Glu Glu Glu Ala Thr
    610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
            660                 665                 670

Ser Ser Pro Asn Asp Arg Thr Phe Pro Asp Asp Arg Asn Phe Leu Arg
        675                 680                 685

Leu Gln Ser Asp Ser Gln Arg Glu Gly Gln Tyr Ala Arg Leu Ile Ser
    690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
                725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Gly Glu Asn Phe Lys Val Asp Ile
                805                 810                 815

Pro Glu Ile His Glu Arg Glu Gly Tyr Glu Asp Glu Ile Asp Asp Glu
            820                 825                 830

Tyr Glu Val Asp Trp Ser Asn Ser Ser Ser Ala Thr Ser Gly Ser Gly
        835                 840                 845

Ala Pro Ser Thr Asp Lys Glu Lys Ser Trp Leu Tyr Thr Leu Asp Pro
    850                 855                 860

Ile Leu Ile Thr Ile Ile Ala Met Ser Ser Leu Gly Val Leu Leu Gly
865                 870                 875                 880

Ala Thr Cys Ala Gly Leu Leu Leu Tyr Cys Thr Cys Ser Tyr Ser Gly
                885                 890                 895

Leu Ser Ser Arg Ser Cys Thr Thr Leu Glu Asn Tyr Asn Phe Glu Leu
            900                 905                 910

Tyr Asp Gly Leu Lys His Lys Val Lys Met Asn His Gln Lys Cys Cys
        915                 920                 925
```

-continued

```
Ser Glu Ala
    930


<210> SEQ ID NO 70
<211> LENGTH: 6
<212> TYPE: PRT
<213> ORGANISM: Homo sapiens

<400> SEQUENCE: 70

Ser Leu Thr Arg Lys Asp
1               5


<210> SEQ ID NO 71
<211> LENGTH: 6
<212> TYPE: PRT
<213> ORGANISM: Homo sapiens

<400> SEQUENCE: 71

Cys Asp Lys Pro Arg Arg
1               5


<210> SEQ ID NO 72
<211> LENGTH: 5
<212> TYPE: PRT
<213> ORGANISM: Homo sapiens

<400> SEQUENCE: 72

Ala Asn Ile Thr Val
1               5


<210> SEQ ID NO 73
<211> LENGTH: 9
<212> TYPE: PRT
<213> ORGANISM: Homo sapiens

<400> SEQUENCE: 73

Ala Asn Ile Thr Val Asn Ile Thr Val
1               5
```